(12) United States Patent
Baloglu et al.

(10) Patent No.: US 7,414,073 B2
(45) Date of Patent: Aug. 19, 2008

(54) CYTOTOXIC AGENTS CONTAINING NOVEL POTENT TAXANES AND THEIR THERAPEUTIC USE

(75) Inventors: Erkan Baloglu, Stoneham, MA (US); Michael Miller, Framingham, MA (US); Ravi V. J. Chari, Newton, MA (US)

(73) Assignee: Immunogen Inc., Cambridge, MA (US)

( * ) Notice: Subject to any disclaimer, the term of this patent is extended or adjusted under 35 U.S.C. 154(b) by 379 days.

(21) Appl. No.: 10/963,711

(22) Filed: Oct. 14, 2004

(65) Prior Publication Data
US 2005/0085513 A1    Apr. 21, 2005

Related U.S. Application Data

(60) Division of application No. 10/369,563, filed on Feb. 21, 2003, which is a continuation-in-part of application No. 10/210,112, filed on Aug. 2, 2002, now abandoned.

(51) Int. Cl.
*A61K 31/335* (2006.01)
*A61K 31/38* (2006.01)
*C07D 305/00* (2006.01)
*C07D 307/00* (2006.01)
*C07D 409/00* (2006.01)

(52) U.S. Cl. .................. 514/449; 514/444; 514/471; 514/232.5; 549/510; 549/511; 549/60; 549/491; 549/492; 530/351; 530/350; 424/155.1; 424/1.49

(58) Field of Classification Search ............. 549/510, 549/511, 491, 492, 60; 514/449, 232.5, 444, 514/471; 530/350, 351; 424/155.1, 1.49

See application file for complete search history.

(56) References Cited

U.S. PATENT DOCUMENTS

| 5,399,726 A | 3/1995 | Holton et al. |
| 5,416,064 A | 5/1995 | Chari et al. |
| 5,475,011 A | 12/1995 | Ojima et al. |

(Continued)

FOREIGN PATENT DOCUMENTS

EP    0624377    5/1994

(Continued)

OTHER PUBLICATIONS

Safavy et al, *J. Med. Chem.*, 42:4919-4924 (1999).

(Continued)

*Primary Examiner*—Janet L. Anders
*Assistant Examiner*—Raymond Covington
(74) *Attorney, Agent, or Firm*—Sughrue Mion, PLLC

(57) ABSTRACT

Included within the scope of the present invention are potent taxanes and taxanes containing a linking group. Also included is a cytotoxic agent comprising one or more taxanes linked to a cell binding agent. A therapeutic composition for inducing cell death in selected cell populations comprising: (A) a cytotoxic amount of one or more taxanes covalently bonded to a cell binding agent through a link, and (B) a pharmaceutically acceptable carrier, diluent or excipient is also included. A method for inducing cell death in selected cell populations comprising contacting target cells or tissue containing target cells with an effective amount of a cytotoxic agent comprising one or more taxanes linked to a cell binding agent is included as well.

57 Claims, 23 Drawing Sheets

| Compound | $R_1$ | $R_2$ | $R_3$ | $R_4$ | $R_5$ |
|---|---|---|---|---|---|
| Paclitaxel (Taxol) | -H | -COCH$_3$ | -C$_6$H$_5$ | -C$_6$H$_5$ | H |
| Docetaxel (Taxotere) | -H | -H | -C$_6$H$_5$ | -OC(CH$_3$)$_3$ | H |
| More Potent Taxanes | -F | -COCH$_2$CH$_3$ | -CH$_2$CH(CH$_3$)$_2$ | -OC(CH$_3$)$_3$ | H |
| | -F | -COCH$_2$CH$_3$ | -CH=C(CH$_3$)$_2$ | -OC(CH$_3$)$_3$ | H |
| | -Cl | -COCH$_2$CH$_3$ | -CH$_2$CH(CH$_3$)$_2$ | -OC(CH$_3$)$_3$ | H |
| | -OCH$_3$ | -COCH$_3$ | -CH$_2$CH(CH$_3$)$_2$ | -OC(CH$_3$)$_3$ | H |

U.S. PATENT DOCUMENTS

| | | | |
|---|---|---|---|
| 5,475,092 A | 12/1995 | Chari et al. | |
| 5,728,725 A | 3/1998 | Holton et al. | |
| 5,811,452 A | 9/1998 | Ojima et al. | |
| 5,824,701 A | 10/1998 | Greenwald et al. | |
| 6,028,205 A | 2/2000 | Holton et al. | |
| 6,175,023 B1 | 1/2001 | Liu | |
| 6,339,164 B1 | 1/2002 | Holton et al. | |
| 6,340,701 B1 * | 1/2002 | Chari et al. | 514/449 |
| 6,372,738 B2 | 4/2002 | Chari et al. | |
| 6,436,931 B1 | 8/2002 | Chari et al. | |
| 6,455,575 B2 * | 9/2002 | Golik et al. | 514/449 |
| 6,596,757 B1 * | 7/2003 | Chari et al. | 514/449 |
| 6,649,777 B2 | 11/2003 | Holton et al. | |
| 6,727,369 B1 | 4/2004 | Holton et al. | |
| 6,958,212 B1 * | 10/2005 | Hubbell et al. | 435/6 |
| 2002/0040155 A1 | 4/2002 | Holton et al. | |

FOREIGN PATENT DOCUMENTS

| | | |
|---|---|---|
| EP | 0 639 577 A1 | 2/1995 |
| EP | 1 022 284 A1 | 7/2000 |
| EP | 1033372 | 9/2000 |
| WO | WO 89/12624 | 12/1989 |
| WO | WO 94/17050 A1 | 8/1994 |
| WO | WO9417050 * | 8/1994 |
| WO | WO 95/07900 A | 3/1995 |
| WO | WO 96/11683 A | 4/1996 |
| WO | WO 96/23779 A | 8/1996 |
| WO | WO 97/44026 | 11/1997 |
| WO | WO 98/19705 | 5/1998 |
| WO | WO 98/52614 | 11/1998 |
| WO | WO 00/50059 | 8/2000 |
| WO | WO 01/38318 A | 5/2001 |
| WO | WO 01/56564 A | 8/2001 |
| WO | WO 01/57013 A | 8/2001 |
| WO | WO 01/57028 A | 8/2001 |
| WO | WO 01/57029 A | 8/2001 |
| WO | WO 01/57030 A | 8/2001 |
| WO | WO 01/57030 A1 | 8/2001 |
| WO | WO0157030 * | 8/2001 |
| WO | WO 03/097625 A | 11/2003 |

OTHER PUBLICATIONS

American Chemical Society Division of Medicinal Chemistry, Abstracts, 218th ACS National Meeting, New Orleans, LA, Aug. 22-26, 1999, A. Trainor, Program Chair.

Synthesis and Biological Acitivity of Advanced 2nd-Generation, Taxoids, Tao Wang et al, Dept. of Chem., State Univ. of NY, at Stony Brook, NY 11794-3400; Dept. of Exp. Therapeutics, Roswell Park Cancer Inst., Elm and Carlton Streets, Buffalo, NY 14263, pp. 1-12.

Ojima et al, *J. Med. Chem.*, 40:267-278 (1997).

Ojima et al, *Proc. Natl. Acad. Sci., USA*, 96:4256-4261 (1999).

Michael L. Miller, et al. "Synthesis of potent taxoids for tumor-specific delivery using monoclonal antibodies", *Bioorganic & Medicinal Chemistry Letters* 14 (2004) 4079-4082.

Erkan Baloglu, et al. "Synthesis and biological evaluation of novel taxoids designed for targeted delivery to tumors", *Bioorganic & Medicinal Chemistry Letters* 14 (2004) 5885-5888.

Michael L. Miller, et al. "Synthesis of Taxoids with Improved Cytotoxicity and Solubility for Use in Tumor-Specific Delivery", *J. Med. Chem.*, 2004, 47, 4802-4805.

Kingston, David G. I., et al., "Synthesis and Biological Evaluation of 2-Acyl Analogues of Paclitaxel (Taxol)," J. Med. Chem, 1998, vol. 41, No. 19, pp. 3715-3726.

Rodi, D. J. et al., "Identification of small molecule binding sites within proteins using phage display technology", Database CA [online ]XP002443942, 2001.

Shi, Bing-Xing et al., "Studies on the quantitative structure-activity relationships of paclitaxel analogs", Database CA [online] XP002443943, 2000.

Guenard, Daniel et al., "Effects of the hydrophobicity of taxoids on their interation with tublin", Database CA [online] XP002443944, 2000.

Gueritte-Voegelein, Francoise et al., "Relationships between the structure of taxol analogs and their antimitotic activity", Database CA [online]XP002443945, 1991.

Office Action Dated Sep. 6, 2005.

Office Action dated Jun. 13, 2006.

Lui, Yanbin et al., "A Systematic SAR study of C10 Modified Paclitaxel Analogues Using a Combinatorial Approach", Combinatorial Chemistry and High Throughput Screening, 5(1), 39-48 Coden:CCHSFU; ISSN: 1386-2073, Feb. 1, 2002.

Ojima, Iwao et al., "Tumor-Specific Novel Taxoid-Monoclonal Antibody Conjugates", Journal of Medicinal Chemistry, vol. 45, No. 26, pp. 5620-5623, Nov. 20, 2002.

* cited by examiner

| Compound | $R_1$ | $R_2$ | $R_3$ | $R_4$ | $R_5$ |
|---|---|---|---|---|---|
| Paclitaxel (Taxol) | -H | -COCH$_3$ | -C$_6$H$_5$ | -C$_6$H$_5$ | H |
| Docetaxel (Taxotere) | -H | -H | -C$_6$H$_5$ | -OC(CH$_3$)$_3$ | H |
| More Potent Taxanes | -F | -COCH$_2$CH$_3$ | -CH$_2$CH(CH$_3$)$_2$ | -OC(CH$_3$)$_3$ | H |
|  | -F | -COCH$_2$CH$_3$ | -CH=C(CH$_3$)$_2$ | -OC(CH$_3$)$_3$ | H |
|  | -Cl | -COCH$_2$CH$_3$ | -CH$_2$CH(CH$_3$)$_2$ | -OC(CH$_3$)$_3$ | H |
|  | -OCH$_3$ | -COCH$_3$ | -CH$_2$CH(CH$_3$)$_2$ | -OC(CH$_3$)$_3$ | H |

Figure 2

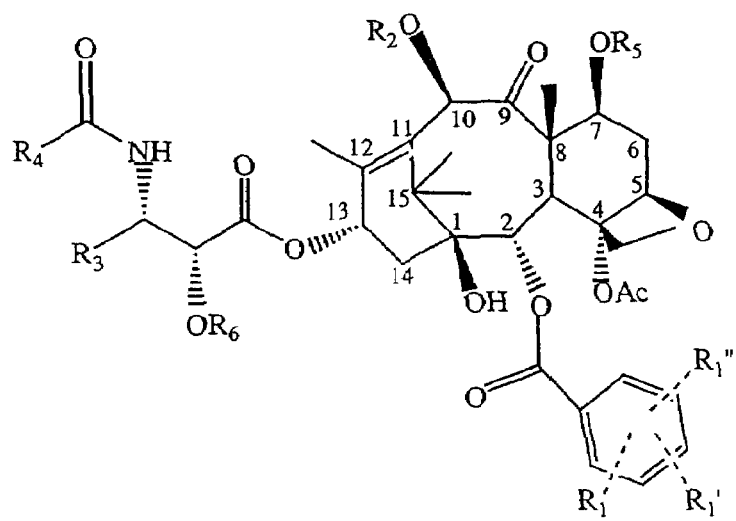

|   | R₁ | R₂ | R₃ | R₄ | R₅ | R₆ |
|---|---|---|---|---|---|---|
| 1 | -F | -H, -COCH₂CH₃ -CH₂CH₃, or -CONHCH₂CH₃ | -CH₂CH(CH₃)₂ or -C₆H₅ | -OC(CH₃)₃ or -C₆H₅ | -CH₂CH₂SH or -COCH₂CH₂SH | -H, -COCH₂CH₃, -CH₂CH₃, or CONHCH₂CH₃ |
| 2 | -F | -H, -COCH₂CH₃, -CH₂CH₃, or -CONHCH₂CH₃ | -CH=C(CH₃)₂ or -C₆H₅ | -OC(CH₃)₃ or -C₆H₅ | -CH₂CH₂SH or -COCH₂CH₂SH | -H, -COCH₂CH₃, -CH₂CH₃, or CONHCH₂CH₃ |
| 3 | -F | -COCH₂CH₂SH -CH₂CH₂SH | -CH₂CH(CH₃)₂ or -C₆H₅ | -OC(CH₃)₃ or -C₆H₅ | -H, -COCH₂CH₃, -CH₂CH₃, or -CONHCH₂CH₃ | -H, -COCH₂CH₃, -CH₂CH₃, or CONHCH₂CH₃ |
| 4 | -F | -H, -COCH₂CH₃, -CH₂CH₃, or -CONHCH₂CH₃ | -CH₂CH(CH₃)₂ or -C₆H₅ | -OC(CH₃)₃ or -C₆H₅ | -H, -COCH₂CH₃, -CH₂CH₃, or -CONHCH₂CH₃ | -H, -CH₂CH₂SH or COCH₂CH₂SH |

| Taxane | $R_1$, $R_1'$, $R_1''$ | $R_2$ | $R_3$ | $R_4$ | $R_5$ | $R_6$ |
|---|---|---|---|---|---|---|
| Paclitaxel | H | $COCH_3$ | Ph | Ph | H | H |
| Docetaxel | H | H | Ph | t-butoxy | H | H |
| 1a | H, OMe or Cl | $-(CH_2)_2SH$ $-CO(CH_2)_2SH$ $-CONH(CH_2)_2SH$ | isobutenyl | t-butoxy | H | H |
| 1b | H, OMe or Cl | | isobutenyl | t-butoxy | $-(CH_2)_2SH$ $-CO(CH_2)_2SH$ $-CONH(CH_2)_2SH$ | H |
| 1c | H, OMe or Cl | | isobutenyl | t-butoxy | | $-(CH_2)_2SH$ $-CO(CH_2)_2SH$ $-CONH(CH_2)_2SH$ |

| Taxane | $R_1, R_1', R_1''$ | $R_2$ | $R_3$ | $R_4$ | $R_5$ | $R_6$ |
|---|---|---|---|---|---|---|
| 2a | H, Cl or OMe | Ac | CH=C(Me)₂ | CH=C(Me)₂ | H | H |
| 2b | H, Cl or OMe | Ac | CH=C(Me)₂ | CH=CHCH₃ | H | H |
| 2c | H, Cl or OMe | Ac | 2-furyl | CH=CHCH₃ | H | H |
| 2d | H, Cl or OMe | Ac | 2-furyl | 2-furyl | H | H |
| 2e | H, Cl or OMe | Ac | 2-furyl | CH=C(Me)₂ | H | H |
| 2f | H, Cl or OMe | Ac | 2-furyl | Ph | H | H |
| 2g | H, Cl or OMe | Ac | 2-furyl | t-butoxy | H | H |

Figure 6

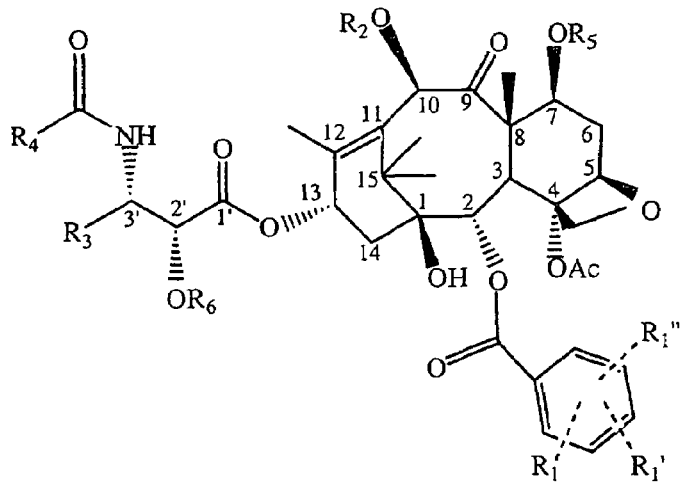

| Taxane | $R_1, R_{1'}, R_{1''}$ | $R_2, R_5, R_6$ | $R_3$ | $R_4$ |
|---|---|---|---|---|
| 3a | H, Cl or OMe | -COCH$_2$CH$_2$SSMe or H | CH=C(Me)$_2$ | CH=CHCH$_3$ |
| | | -COCH$_2$CH$_2$SSMe or H | CH=C(Me)$_2$ | CH=C(Me)$_2$ |
| | | -COCH$_2$CH$_2$SSMe or H | 2-furyl | 2-furyl |
| | | -COCH$_2$CH$_2$SSMe or H | 2-furyl | t-butoxy |
| 3b | H, Cl or OMe | -CO(CH$_2$CH$_2$O)$_4$(CH$_2$)$_2$SSMe or H | CH=C(Me)$_2$ | CH=CHCH$_3$ |
| | | -CO(CH$_2$CH$_2$O)$_4$(CH$_2$)$_2$SSMe or H | CH=C(Me)$_2$ | CH=C(Me)$_2$ |
| | | -CO(CH$_2$CH$_2$O)$_4$(CH$_2$)$_2$SSMe or H | 2-furyl | 2-furyl |
| | | -CO(CH$_2$CH$_2$O)$_4$(CH$_2$)$_2$SSMe or H | 2-furyl | t-butoxy |
| 3c | H, Cl or OMe | -COCH$_3$ or H | 2-furyl -(CH$_2$)$_n$SH | t-butoxy |
| | | -COCH$_3$ or H | 2-furyl -(CH$_2$)$_n$SH | 2-furyl |
| 3d | H, Cl or OMe | -COCH$_3$ or H | t-butoxy | 2-furyl -(CH$_2$)$_n$SH |
| | | -COCH$_3$ or H | 2-furyl | 2-furyl -(CH$_2$)$_n$SH |
| 3e | H, Cl or OMe | -COCH$_3$ or H | 2-furyl | CH=C(Me)CH$_2$CH$_2$SH |
| | | -COCH$_3$ or H | CH=C(Me)$_2$ | CH=C(Me)CH$_2$CH$_2$SH |
| 3f | H, Cl or OMe | -COCH$_3$ or H | CH=C(Me)CH$_2$CH$_2$SH | 2-furyl |
| | | | CH=C(Me)CH$_2$CH$_2$SH | t-butoxy |
| | | | CH=C(Me)CH$_2$CH$_2$SH | CH=C(Me)$_2$ |

Figure 7 Structure of 10-deacetyl Baccatin III
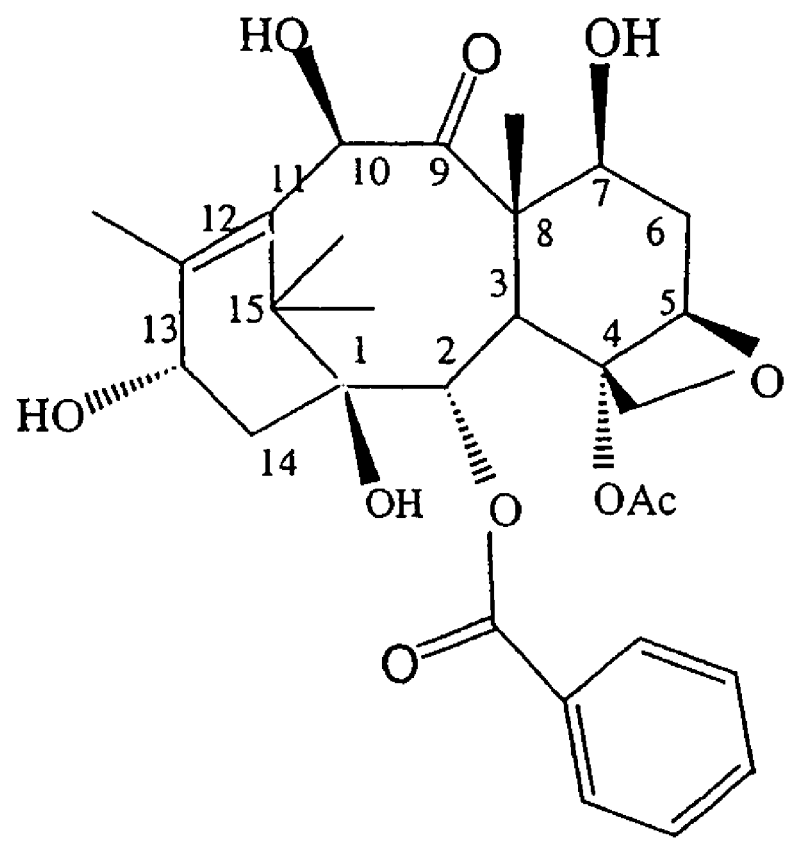

|  | IC$_{50}$, M |
|---|---|
| Taxane 1' | > 3 x 10$^{-9}$ |
| Taxane 2' | 8 x 10$^{-10}$ |

| Cell line | $IC_{50}$, M |
|---|---|
| A549 | $1.8 \times 10^{-10}$ |
| MCF-7 | $6.3 \times 10^{-11}$ |

Figure 16a Synthesis of New Taxanes
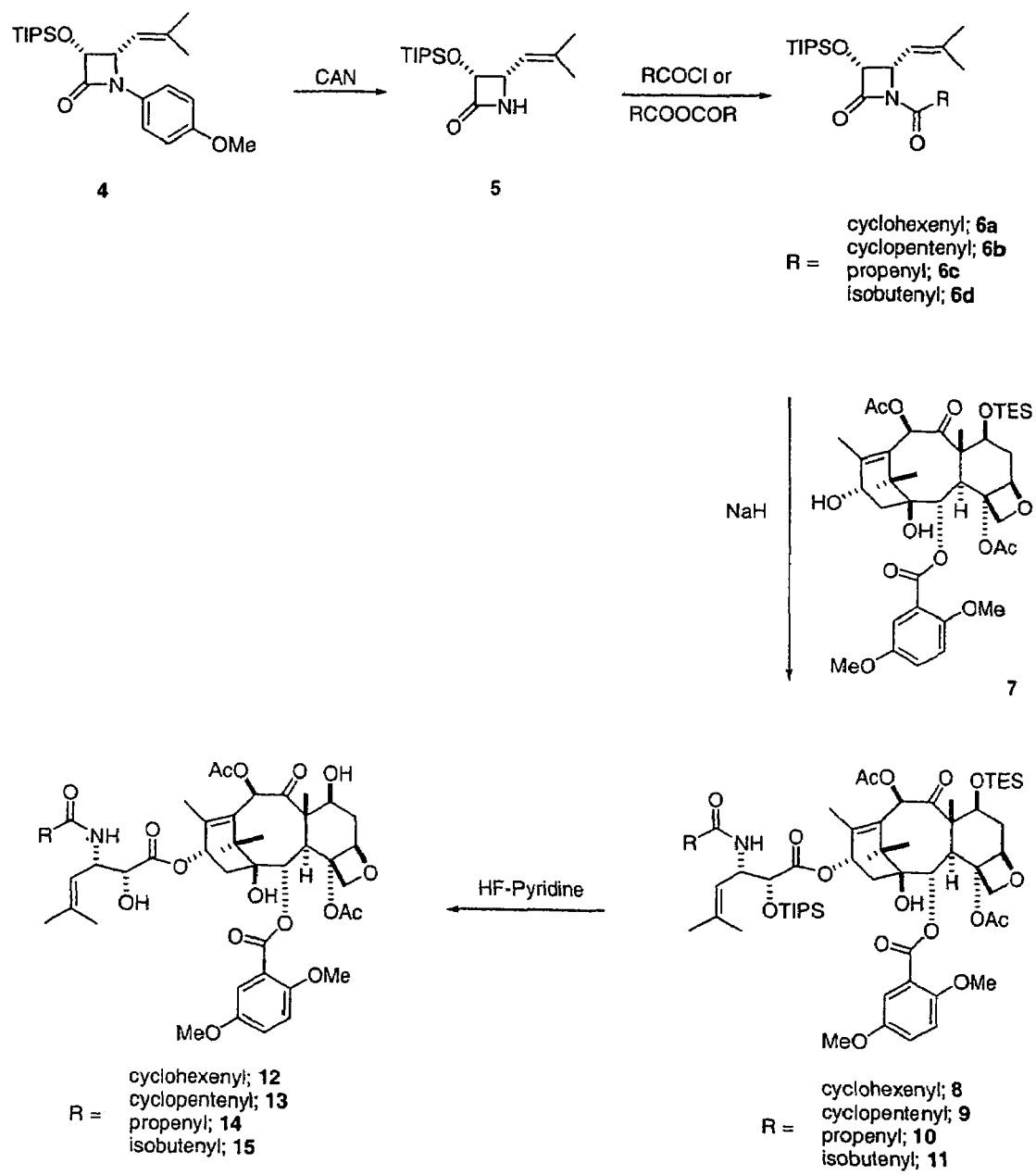

Figure 16b Synthesis of New Taxanes
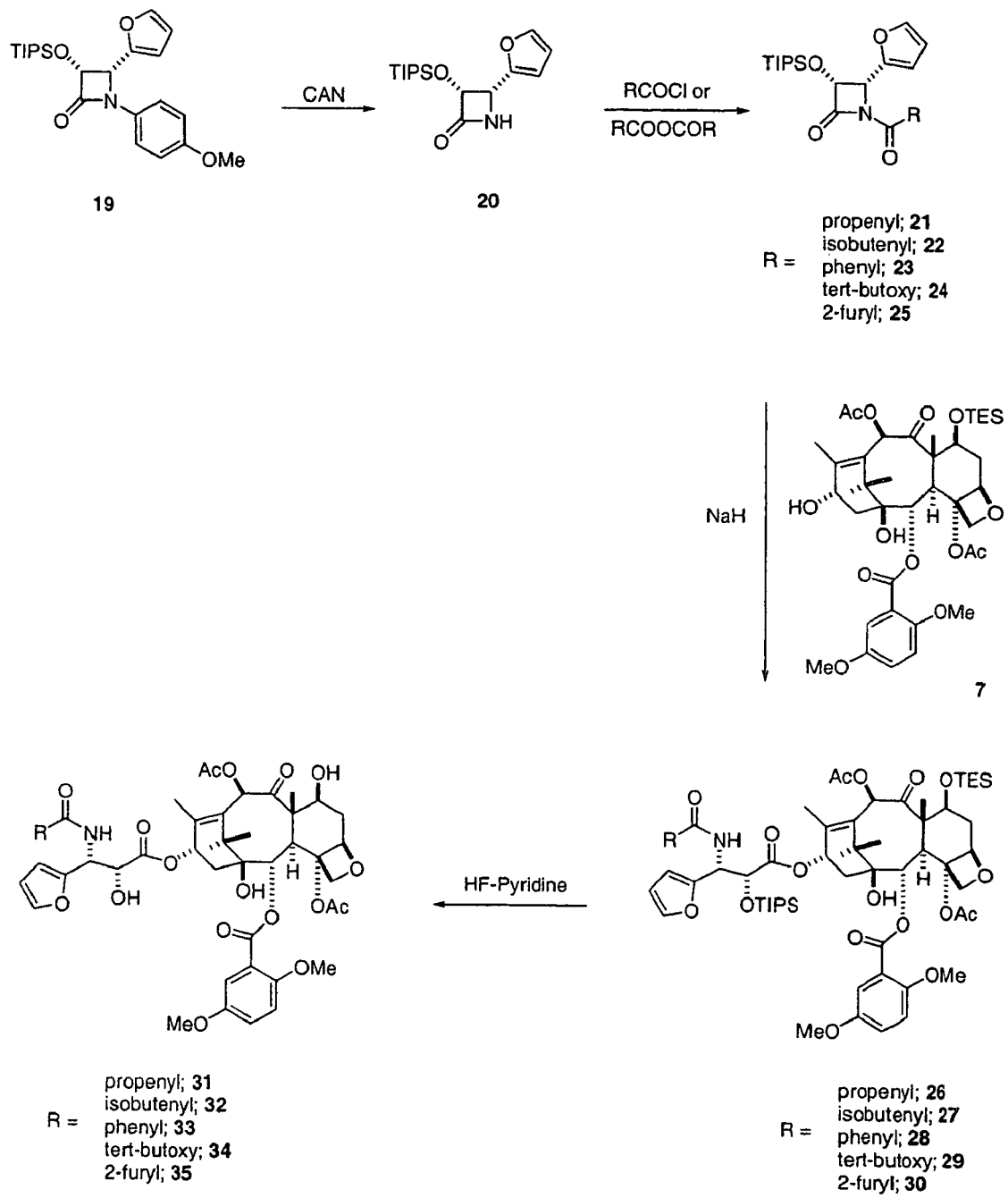

Figure 16c Synthesis of New Taxanes
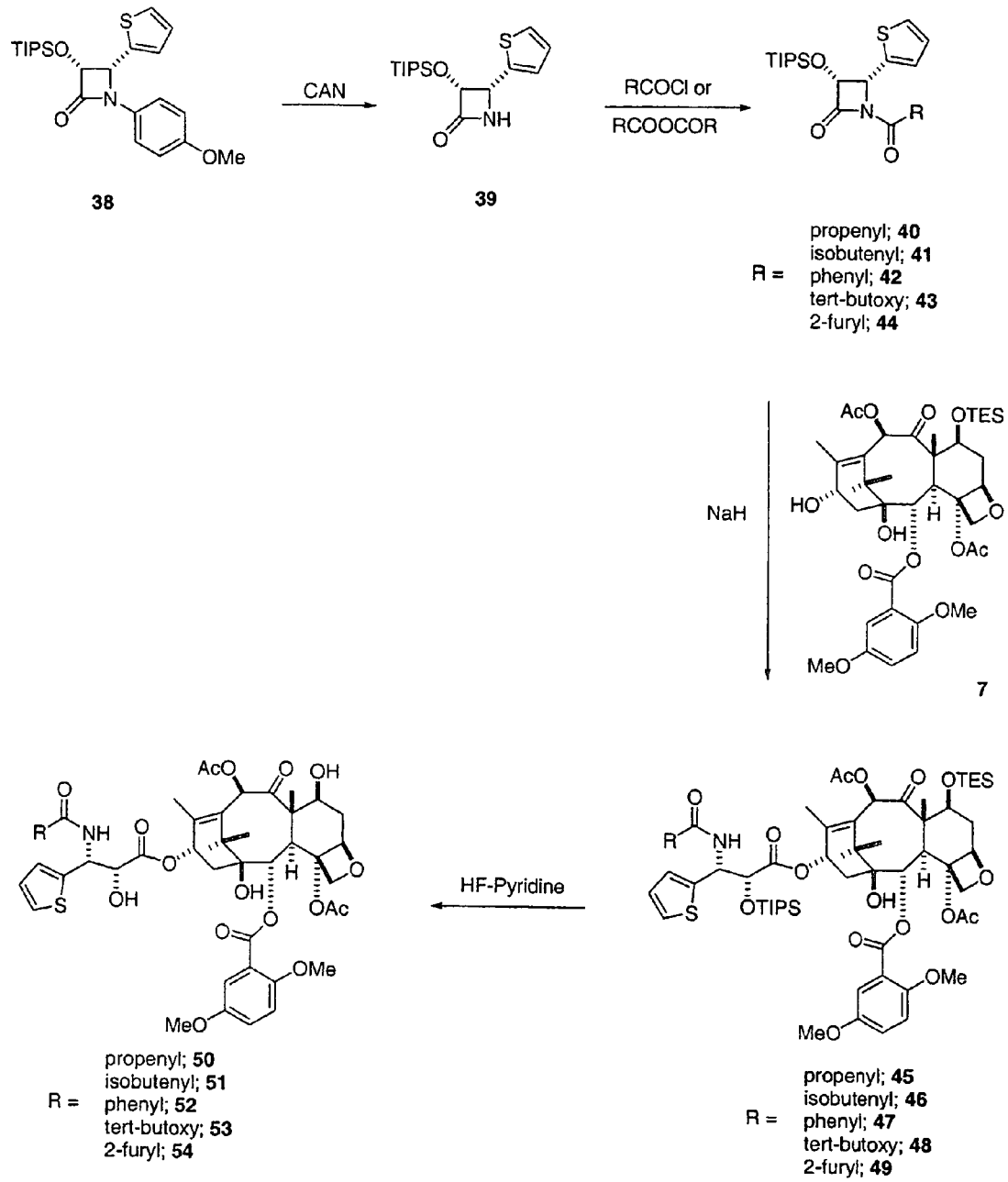

Fig. 17a Synthesis of New Disulfide containing Taxanes
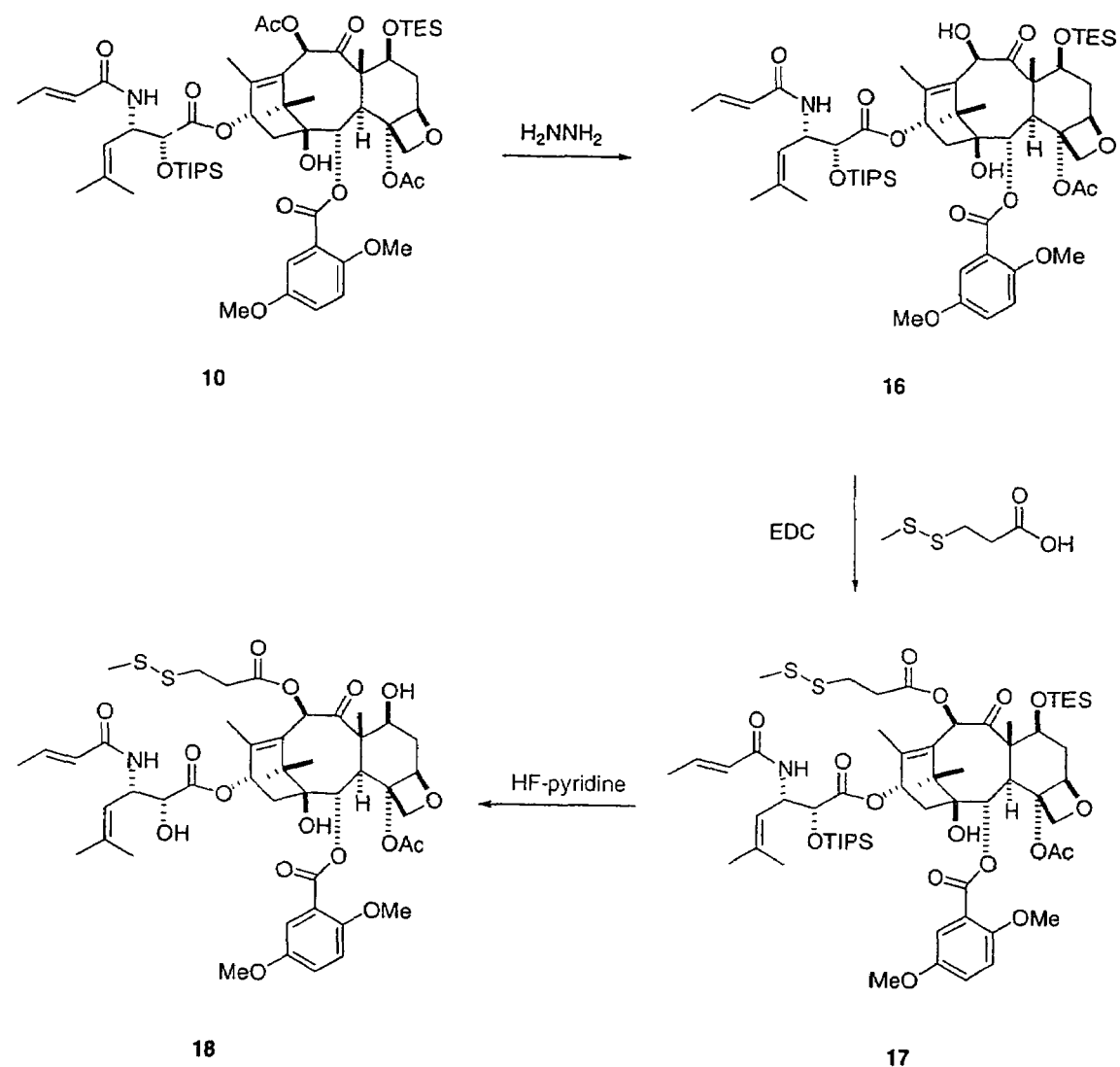

Figure 17b Synthesis of New Disulfide containing Taxane
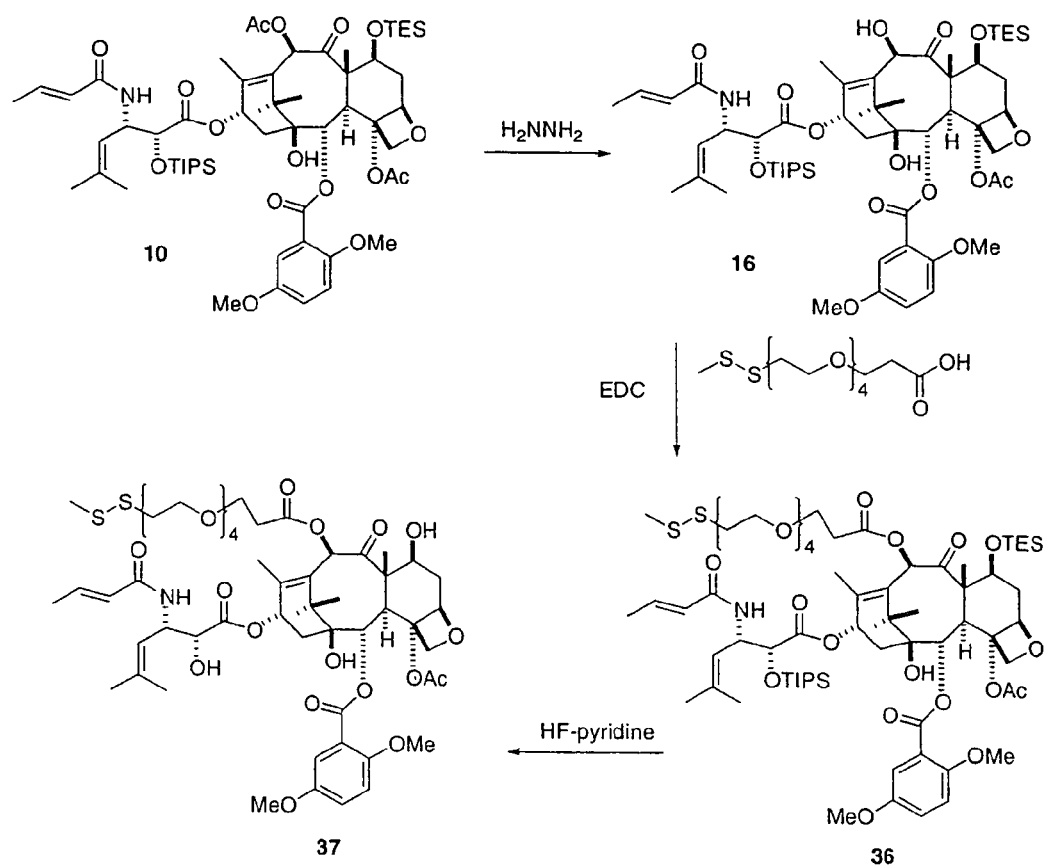

Figure 18  *In Vitro* Cytotoxicity of New Taxanes

| Taxane | IC$_{50}$ (M) | |
|---|---|---|
| | A-549 cells | MCF-7 cells |
| 14 | $3.0 \times 10^{-11}$ | $1.2 \times 10^{-11}$ |
| 15 | $4.0 \times 10^{-11}$ | $4.3 \times 10^{-11}$ |
| 31 | $1.6 \times 10^{-10}$ | $1.3 \times 10^{-10}$ |
| 32 | $3.2 \times 10^{-11}$ | $4.0 \times 10^{-11}$ |
| 33 | $2.2 \times 10^{-10}$ | $1.1 \times 10^{-10}$ |
| 34 | $3.0 \times 10^{-11}$ | $4.0 \times 10^{-11}$ |
| 35 | $9.0 \times 10^{-11}$ | $1.2 \times 10^{-10}$ |
| 50 | $1.8 \times 10^{-10}$ | $1.6 \times 10^{-10}$ |
| 51 | $4.7 \times 10^{-11}$ | $5.0 \times 10^{-11}$ |
| 52 | $3.0 \times 10^{-9}$ | $3.0 \times 10^{-9}$ |
| 53 | $4.7 \times 10^{-11}$ | $3.2 \times 10^{-11}$ |
| 54 | $5.5 \times 10^{-11}$ | $6.5 \times 10^{-11}$ |

Figure. 19 *In VItro* Cytotoxicity of Disulfide- Containing Taxanes
Figure 19a) Cytotoxicity of Taxane 18
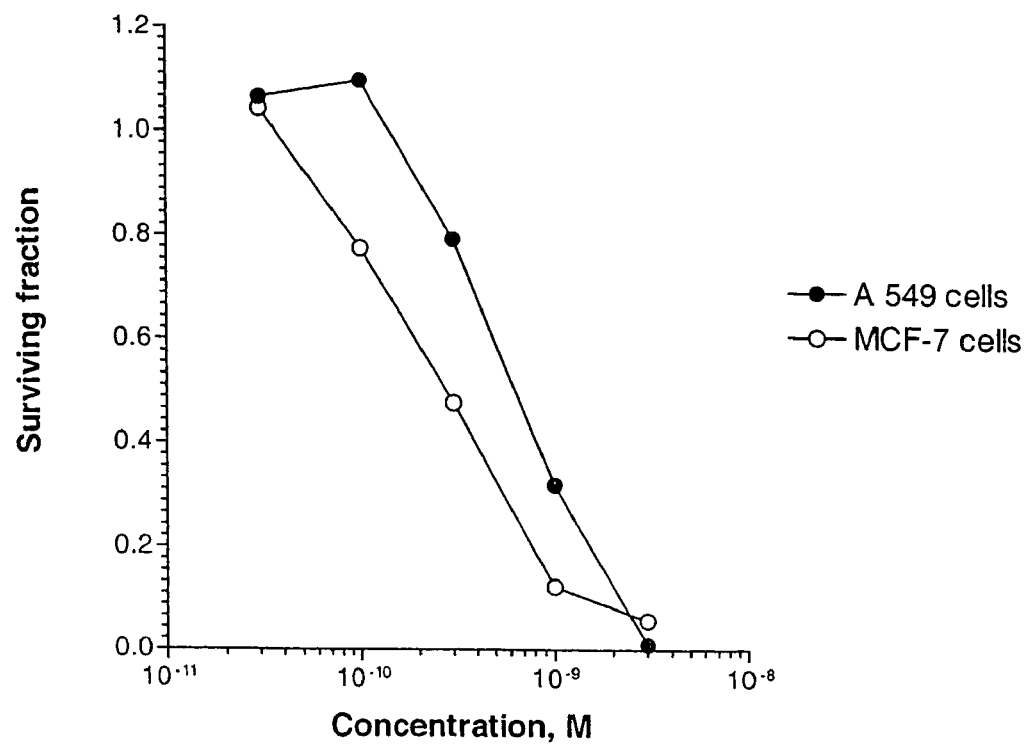

Figure 19b) In Vitro Cytotoxicity of Disulfide-Containing Taxane 37
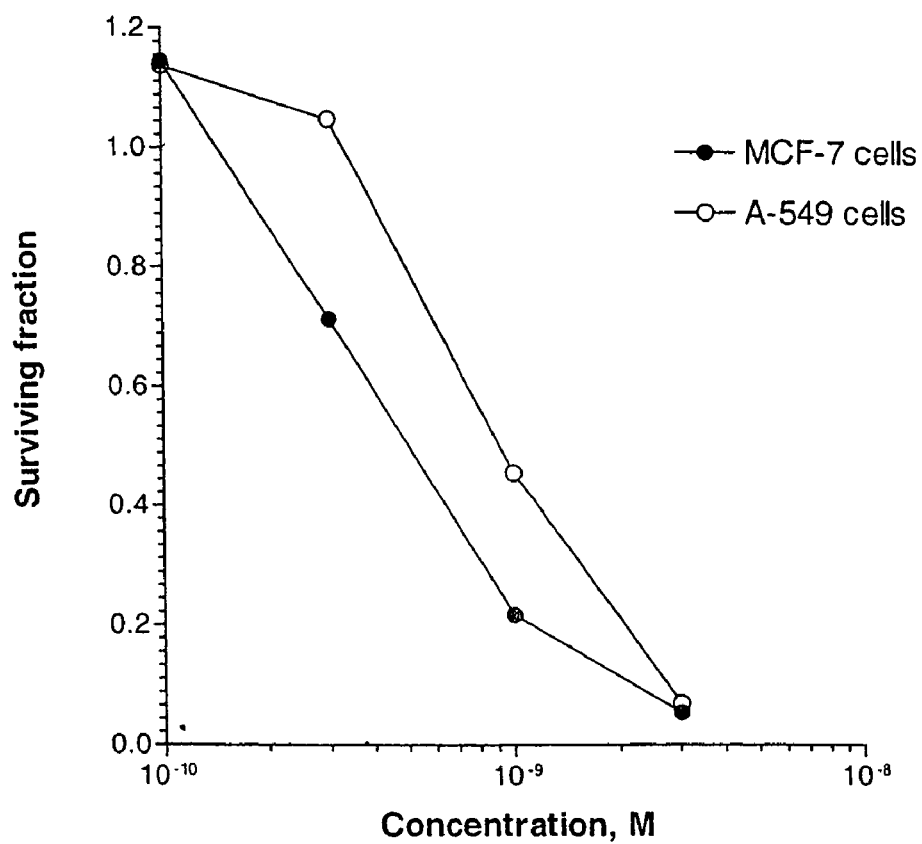

CYTOTOXIC AGENTS CONTAINING NOVEL POTENT TAXANES AND THEIR THERAPEUTIC USE

This is a divisional of U.S. application Ser. No. 10/369,563, filed Feb. 21, 2003, which is a continuation-in-part of U.S. application Ser. No. 10/210,112, filed Aug. 2, 2002 (abandoned).

FIELD OF THE INVENTION

The present invention relates to novel cytotoxic agents and their therapeutic use. More specifically, the invention relates to novel taxanes, novel cytotoxic agents comprising the novel taxanes and their therapeutic use. These novel cytotoxic agents have therapeutic use in that taxanes are delivered to a selected cell population in a targeted fashion by chemically linking the taxanes to a cell-binding agent that is able to target the selected cell population.

BACKGROUND OF THE INVENTION

The specificity of cytotoxic agents can be greatly improved by targeted delivery through linkage of the cytotoxic agents to cell-binding agents.

Many reports have appeared on the attempted specific targeting of tumor cells with monoclonal antibody-drug conjugates (Sela et al, in *Immunoconjugates* 189-216 (C. Vogel, ed. 1987); Ghose et al, in *Targeted Drugs* 1-22 (E. Goldberg, ed. 1983); Diener et al, in *Antibody mediated delivery systems* 1-23 (J. Rodwell, ed. 1988); Pietersz et al, in *Antibody mediated delivery systems* 25-53 (J. Rodwell, ed. 1988); Bumol et al, in *Antibody mediated delivery systems* 55-79 (J. Rodwell, ed. 1988)). All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, *Cancer Res*. 46: -2412 (1986); Ohkawa et al, *Cancer Immunol. Immunother*. 23: 86 (1986); Endo et al, *Cancer Res*. 47: 1076-1080 (1980)), dextran (Hurwitz et al, *Appl. Biochem*. 2: 25-35 (1980); Manabi et al, *Biochem. Pharmacol*. 34: 289-291 (1985); Dillman et al, *Cancer Res*. 46: 4886-4891 (1986); Shoval et al, *Proc. Natl. Acad. Sci*. 85: 8276-8280 (1988)), or polyglutamic acid (Tsukada et al, *J. Natl. Canc. Inst*. 73: 721-729 (1984); Kato et al, *J. Med. Chem*. 27: 1602-1607 (1984); Tsukada et al, *Br. J. Cancer* 52: 111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (*Biochem. Biophys. Res. Commun*. 102: 1048-1054 (1981)). Yang and Reisfeld used the same technique to conjugate daunorubicin to an anti-melanoma antibody (*J. Natl. Canc. Inst*. 80: 1154-1159 (1988)). Dillman et al. also used an acid-labile linker in a similar fashion to prepare conjugates of daunorubicin with an anti-T cell antibody (*Cancer Res*. 48: 6097-6102 (1988)).

An alternative approach, explored by Trouet et al, involved linking daunorubicin to an antibody via a peptide spacer arm (*Proc. Natl. Acad. Sci*. 79: 626-629 (1982)). This was done under the premise that free drug could be released from such a conjugate by the action of lysosomal peptidases. In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient.

In the area of immunotoxins, conjugates formed via disulfide bridges between monoclonal antibodies and catalytically active protein toxins were shown to be more cytotoxic than conjugates containing other linkers. See, Lambert et al, *J. Biol. Chem*. 260: 12035-12041 (1985); Lambert et al, in *Immunotoxins* 175-209 (A. Frankel, ed. 1988); Ghetie et al, *Cancer Res*. 48: 2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. (Shen et al, *J. Biol. Chem*. 260: 10905-10908 (1985)) described the conversion of methotrexate into a mercaptoethylamide derivative followed by conjugation with poly-D-lysine via a disulfide bond. Another report described the preparation of a conjugate of the trisulfide containing toxic drug calicheamycin with an antibody (Hinman et al, *Cancer Res*. 53: 3336-3342 (1993)).

One reason for the lack of disulfide linked antibody-drug conjugates is the unavailability of cytotoxic drugs possessing a sulfur atom containing moiety that can be used readily to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream.

In spite of the above-described difficulties, useful cytotoxic agents comprising cell-binding moieties and the group of cytotoxic drugs known as maytansinoids have been reported (U.S. Pat. No. 5,208,020, U.S. Pat. No. 5,416,064, and R. V. J. Chari, *Advanced Drug Delivery Reviews* 31: 89-104 (1998)). Similarly, useful cytotoxic agents comprising cell-binding moieties and analogues and derivatives of the potent antitumor antibiotic CC-1065 have also been reported (U.S. Pat. No. 5,475,092 and U.S. Pat. No. 5,585,499).

It has also been shown that the linkage of highly cytotoxic drugs to antibodies using a cleavable link, such as a disulfide bond, ensures the release of fully active drug inside cells, and such conjugates are cytotoxic in an antigen specific manner (R. V. J. Chari et al, *Cancer Res*. 52: 127-131 (1992); U.S. Pat. No. 5,475,092; and U.S. Pat. No. 5,416,064).

Taxanes are a family of compounds that includes paclitaxel (Taxol), a cytotoxic natural product, and docetaxel (Taxotere), a semi-synthetic derivative (see FIGS. 1 and 4), two compounds that are widely used in the treatment of cancer, E. Baloglu and D. G. I. Kingston, *J. Nat. Prod*. 62: 1448-1472 (1999). Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

Recently, a few new docetaxel analogs with greater potency than either docetaxel or paclitaxel have been described (I. Ojima et al, *J. Med. Chem*., 39: 3889-3896 (1996)). However, these compounds lack a suitable functionality that allows linkage via a cleavable bond to cell-binding agents (FIG. 1).

The synthesis of novel taxanes that retain high cytotoxicity and that can be effectively linked to cell-binding agents has been described recently (U.S. Pat. Nos. 6,340,701, 6,372,738 and 6,436,931, and FIGS. 2 and 4). In these disclosures, taxanes were modified with chemical moieties, ones containing thiol or disulfide groups in particular, to which appropriate cell-binding agents could be linked. As a result, these novel taxanes preserved, and in some cases even enhanced, the cytotoxic potency of known taxanes.

In the taxanes described in the aforementioned patents, the linking group was introduced at the C-10, C-7 or the C-2' position of the taxane.

In the cases where the linking group was at C-7, the C-10 position did not have a free hydroxyl substituent but was rather an ester, ether or carbamate substituent. It has been previously shown (I. Ojima et al, *J. Med Chem*., 39: 3889-3896 (1996)) that the presence of an ester or carbamate substituent at C-10 produced taxoids of high potency. However, there have been no studies on the potency of taxanes bearing a free hydroxyl group at C-10 and a linking group at C-7.

As described herein, the potency of taxanes bearing a free hydroxyl group at C-10 and a linking group at C-7 was found to meet or exceed the potency of taxanes bearing an ester, ether or carbamate substituent at C-10 and a linking group at C-7. Thus, in a first aspect, the present invention provides these novel taxanes bearing a free hydroxyl group at C-10 and a linking group at C-7 and having potent cytotoxic activity.

Further, in the taxanes described in the aforementioned patents, the linking group was introduced at the C-10, C-7 or the C-2' position of the taxane. In all taxanes, the substituents at C-3'N and C-3', were named —$NHCOR_4$ and $R_3$, respectively. Furthermore, the substituent at C-3'N, —$NHCOR_4$, was either a benzamido group ($R_4$=phenyl), like in paclitaxel, or a tert-butyloxycarbonylamino moiety (—NH-t-BOC, $R_4$=t-butoxy), like in docetaxel. Based on published data, it was assumed that altering these substituents would cause a loss in potency. The substituent at C-3' ($R_3$) was either aryl or a linear, branched or cyclic alkyl group having 1 to 10 carbon atoms. Since, based on published data, it was thought that the substituents at C-3'N and C-3' could not be altered without a loss in drug activity, the linking group was always introduced at a different position of the taxane, namely at C-7, C-10 or C-2'. Also, the inability to change the substituents at C-3' or C-3'N greatly limited the variety of disulfide-containing taxanes that could be synthesized.

In a second aspect, the present invention is also based on the unexpected finding that the substituents at both C-3' and C-3'N do not have to be limited to that present in the known taxanes. As described herein, the potency of taxanes bearing a variety of different substituents at C-3'N meets or exceeds the potency of taxanes bearing a benzamido or —NH-t-BOC substituent at this position. The new substituent at C-3' or C-3'N can also contain a linking group that allows for linkage to cell-binding agents. The present invention discloses these novel highly potent taxanes bearing a variety of different substituents at C-3' and C-3'N. The linking group can now be incorporated at any one of the five positions: C-3', C-3'N, C-10, C-7 or C-2'.

SUMMARY OF THE INVENTION

In one embodiment of the present invention, novel taxanes that are highly cytotoxic and that can still be effectively used in the treatment of many diseases are disclosed.

In a second embodiment of the present invention, novel taxanes that bear a free hydroxyl group at the C-10 position and a linking group at C-7, and that still maintain high potency, are disclosed.

In a third embodiment of the present invention, novel taxanes that bear a variety of different substituents at C-3'N or C-3', and a linking group at C-7, C-10, C-2' or C-3'N or C-3' and that still maintain high potency, are disclosed.

In a fourth embodiment of the present invention, a cytotoxic agent comprising one or more novel taxanes covalently bonded to a cell-binding agent through a link is disclosed.

In a fifth embodiment of the present invention, a therapeutic composition comprising:

(a) a therapeutically effective amount of one or more novel taxanes linked to a cell-binding agent, and (b) a pharmaceutically acceptable carrier, diluent, or excipient, is disclosed.

In a sixth embodiment of the present invention, a method of inducing cell death in selected cell populations comprising contacting target cells or tissue containing target cells, with an effective amount of a cytotoxic agent comprising one or more novel taxanes linked to a cell-binding agent is disclosed.

BRIEF DESCRIPTION OF THE DRAWINGS

FIG. 1 is a chemical formula that represents structures of various taxanes, including some of the more potent taxanes described by Ojima et al., supra.

FIG. 2 is a chemical formula that represents structures of some of the disulfide-containing taxanes according to the present invention that bear a free hydroxyl group at the C-10 position and a linking group at C-7.

FIG. 3 shows the structure of three taxanes. Taxane 1 bears an ester group at C-10 and a linking group at C-7. Both taxane 2' and taxane 3' bear a free hydroxy group at C-10 and a linking group at C-7.

FIG. 4 is a chemical formula that represents structures of various taxanes, including some of the more potent taxanes described in U.S. Pat. Nos. 6,340,701, 6,372,738 and 6,436,931.

FIG. 5 is a chemical formula that represents structures of some of the new taxanes according to the present invention that have a substituent at $R_3$ and/or $R_4$ not previously described.

FIG. 6 is a chemical formula that represents structures of some of the new disulfide-containing taxanes according to the present invention that have a substituent at $R_3$ and/or $R_4$ not previously described.

FIG. 7 shows the structure of 10-deacetylbaccatin III, which is the starting material for preparing taxanes.

FIG. 8 shows the synthetic steps in the production of taxane 2'.

FIG. 9 shows the synthetic steps in the production of taxane 3'.

FIGS. 16a, 16b and 16c show the synthetic steps in the production of new taxanes according to the second aspect of the present invention.

FIGS. 17a and 17b show the synthetic steps in the production of new disulfide-containing taxanes according to the second aspect of the present invention.

FIG. 18 shows the in vitro cytotoxicity of new taxanes according to the second aspect of the present invention FIGS. 19a and 19b show the in vitro cytotoxicity of disulfide-containing taxanes according to the second aspect of the present invention.

DETAILED DESCRIPTION OF THE INVENTION

Figure 1:
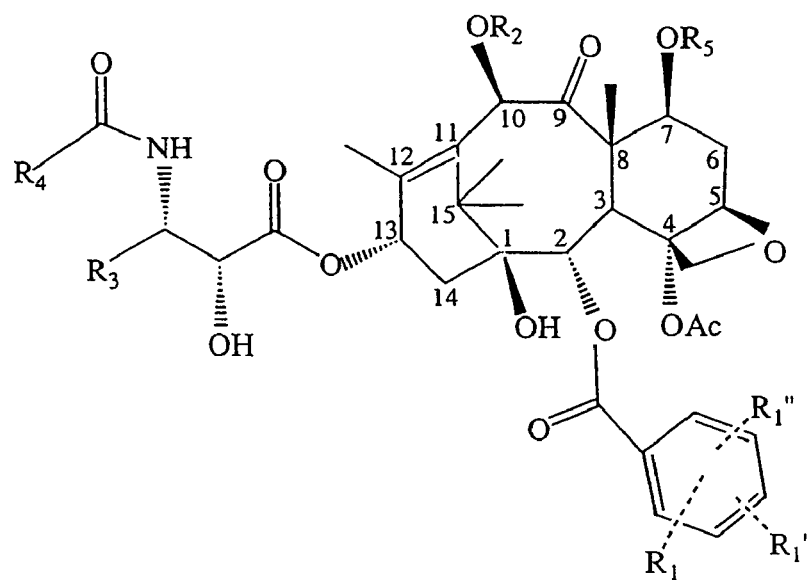

The present invention describes novel taxanes that retain high cytotoxicity and that can be effectively linked to cell binding agents. It has previously been shown that taxanes possessing a protected hydroxyl group at C-10 are highly potent (U.S. Pat. Nos. 6,340,701, 6,372,738 and 6,436,931). The first aspect of the present invention is based on the unexpected finding that the C-10 position does not have to be protected to attain high potency. Taxanes bearing a free hydroxy group at C-10 still maintain high potency as long as there is a protected hydroxy group at C-7, such as a linking group.

The present invention further describes the synthesis and in vitro evaluation of taxanes bearing a free hydroxyl group at C-10 and a linking group at C-7.

Also, it has previously been shown that taxanes possessing a benzamido or a tert-butyloxycarbonylamino (—NH-t-BOC) substituent at C-3'N along with another substituent which is an aryl or a linear branched or cyclic alkyl group are highly potent. The second aspect of the invention is based on the unexpected finding that the C-3'N position does not have to possess a benzamido or a —NH-t-BOC group to attain high potency. A number of different amide or carbamate substituents bearing alkyl, alkenyl or heterocyclic side chains can be used without any loss in potency. The linking group can be introduced on the side chains at C-3', C-3'N, or on the C-10, C-7 or C-2' positions.

The precursor to the synthesis of taxanes is the naturally occurring compound 10-deacetylbaccatin III (10-DAB) (FIG. 7). A large variety of taxanes bearing a linking group can be prepared. Further, this compound has a free hydroxy group at the C-10 position. Therefore, the number of synthetic steps needed for the production of a cytotoxic taxane according to the first aspect of the invention can be decreased because the hydroxyl group does not have to be converted into an ester, ether or carbamate. The yield of taxanes bearing a linking group can also be increased.

The present invention further describes the synthesis and in vitro evaluation of representative taxanes bearing new substituents at C-3' or C-3'N, with or without a linking group at C-7, C-10, C-2' or at C-3', C-3'N.

The art reveals that it is extremely difficult to modify existing drugs without diminishing their cytotoxic potential. The disclosed invention overcomes this problem by modifying the disclosed taxanes with chemical moieties, including ones containing thiol or disulfide groups, to which appropriate cell-binding agents can be linked. As a result, the disclosed novel taxanes preserve, and in some cases could even enhance, the cytotoxic potency of known taxanes. The cell-binding agent-taxane complexes permit the full measure of the cytotoxic action of the taxanes to be applied in a targeted fashion against unwanted cells only, therefore, avoiding side effects due to damage to non-targeted healthy cells. This invention permits the taxanes to be target site-directed, which had been impossible previously. Thus, the invention provides useful agents for the elimination of diseased or abnormal cells that are to be killed or lysed, such as tumor cells (particularly solid tumor cells), virus infected cells, microorganism infected cells, parasite infected cells, autoimmune cells (cells that produce autoantibodies or cells that regulate the production of autoantibodies), activated cells (those involved in graft rejection or graft vs. host disease), or any other type of diseased or abnormal cells, while exhibiting a minimum of side effects.

The cytotoxic agent according to the present invention comprises one or more taxanes linked to a cell-binding agent via a link. The link is part of a chemical moiety that is covalently bound to a taxane through conventional methods. In a preferred embodiment, the cell-binding agent can be covalently bound to the taxane via a disulfide or a thioether linkage.

In the following description of embodiments (1) to (9), the following apply:

The term "alkyl" means linear, branched or cyclic, unless otherwise specified.

Examples of linear alkyls include methyl, ethyl, propyl, butyl, pentyl and hexyl.

Examples of branched alkyls include isopropyl, isobutyl, sec.-butyl, tert.-butyl, isopentyl and 2-ethyl-propyl.

Examples of cyclic alkyls include cyclopropyl, cyclobutyl, cyclopentyl and cyclohexyl.

Examples of alkenyls and cycloalkenyls include isobutenyl, hexenyl, cyclopentenyl, and cyclohexenyl.

Examples of simple aryls include phenyl and naphthyl.

Examples of substituted aryls include aryls such as those described above substituted with alkyl groups, halogens, such as Cl, Br or F, nitro groups, amino groups, sulfonic acid groups, carboxylic acid groups, hydroxy groups or alkoxy groups.

Heterocyclics are compounds wherein the heteroatoms are selected from O, N, and S, and include morpholino, piperidino, piperazino, N-methylpiperazino, pyrrollyl, pyridyl, furyl, imidazolyl, oxazolyl, thiazolyl, thiopheneyl, indolyl, benzofuranyl, and benzothiopheneyl.

Examples of carbamates are those formed from alkyl, alkenyl, cycloalkyl, cycloalkenyl and aryl moieties, such as, methyl, ethyl, crotonyl, cyclohexyl, cyclohexenyl and phenyl, and from nitrogen-containing heterocyclics, such as morpholino, piperidino, piperazino and N-methyl piperazino.

Examples of aryl esters, ethers, and carbamates include phenyl and napthyl ethers, esters and carbamates.

Examples of linear, branched or cyclic alkyl or alkenyl esters include methyl, ethyl, isopropyl, allyl, propenyl, cyclohexyl and cyclohexenyl esters.

Examples of linear, branched or cyclic alkyl or alkenyl ethers include methyl, ethyl, isopropyl, allyl, propenyl, and cyclohexyl ethers.

The taxanes useful in the present invention have the formula (I) shown below:

(I)

[Chemical structure diagram of taxane with positions labeled 1-15, showing substituents $R_2O$, $OR_5$, $OR_6$, $R_4$, $R_3$, NH, OH, OAc, and aromatic ring with $R_1$, $R_1'$, $R_1''$]

These novel taxanes can be divided into nine embodiments, designated (1) to (9). Examples of the embodiments (1) to (4) are shown in FIG. 2. Examples of embodiments (5) to (9) are shown in FIG. 6.

Embodiments (1)-(4)

In embodiments (1) to (4), $R_1$ is H, an electron withdrawing group, such as F, $NO_2$, CN, Cl, $CHF_2$ and $CF_3$ or an electron donating group such as —$OCH_3$, —$OCH_2CH_3$, —$NR_7R_8$ and —$OR_9$. $R_1'$ and $R_1''$ are the same or different and are H, an electron withdrawing group, such as F, $NO_2$, CN, Cl, $CHF_2$ and $CF_3$ or an electron donating group such as —$OCH_3$, —$OCH_2CH_3$, —$NR_7R_8$ and —$OR_9$.

$R_7$ and $R_8$ are the same or different and are linear, branched, or cyclic alkyl groups having from 1 to 10 carbon atoms, or simple or substituted aryl. Preferably the number of carbon atoms for $R_7$ and $R_8$ is 1 to 4. Also, preferably $R_7$ and $R_8$ are the same. Examples of preferred —$NR_7R_8$ groups include dimethyl amino, diethyl amino, di-isopropyl amino and dibutyl amino, where the butyl moiety is any of primary, secondary, tertiary or isobutyl.

$R_9$ is linear, branched or cyclic alkyl having 1 to 10 carbon atoms. $R_1$ is preferably —$OCH_3$, Cl, F, $NO_2$, and $CF_3$.

More preferably, $R_1$ is —$OCH_3$ and is in the meta position, and one of $R_1'$ and $R_1''$ is —$OCH_3$ and the other is H.

In embodiments (1), (2) and (4), $R_2$ is H, or together with the oxygen atom at the C-10 position, a heterocyclic or aryl ether, a heterocyclic or aryl ester, a heterocyclic or aryl carbamate, a linear, branched or cyclic alkyl ester having from 1 to 10 carbon atoms in the alkyl, a linear, branched or cyclic alkenyl ester having from 2 to 10 carbon atoms in the alkenyl, a linear, branched or cyclic alkyl ether having from 1 to 10 carbon atoms, a linear, branched or cyclic alkenyl ether having from 2 to 10 carbon atoms, a carbamate of the formula —OCOX, wherein X is a nitrogen-containing heterocyclic, such as piperidino, morpholino, piperazino and N-methylpiperazino, or a carbamate of the formula —$OCONR_{10}R_{11}$, wherein $R_{10}$ and $R_{11}$ are the same or different and are H, linear, branched or cyclic alkyl having 1 to 10 carbon atoms, or simple or substituted aryl.

Preferred examples of aryl ethers, esters and carbamates include phenyl and naphthyl ethers, esters and carbamates.

Preferred examples of alkyl and alkenyl esters include —$OCOCH_3$, —$OCOCH_2CH_3$, crotonyl and dimethylacryloyl. Preferred examples of alkyl and alkenyl ethers include methyl, ethyl, allyl, propyl, propenyl and isobutenyl ethers. Preferred examples of carbamates include —$OCONHCH_2CH_3$, —$OCONHCH_2CH_2CH_3$, —OCO-morpholino, —OCO-piperazino, —OCO-piperidino and —OCO—N-methylpiperazino. Preferably, $R_2$ is H.

In embodiment (3), $R_2$ is the linking group.

In embodiments (1), (3) and (4), $R_3$ is alkyl having from 1 to 10 carbon atoms, alkenyl having from 2 to 10 carbon atoms, cycloalkyl or cycloalkenyl having from 3 to 10 carbon atoms, aryl, or heterocyclic.

Preferably, $R_3$ is propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl.

More preferably, $R_3$ is t-BOC, iso-butenyl, propenyl, thiophenyl, thiazolyl or furyl.

In embodiment (2), $R_3$ is —CH=C$(CH_3)_2$.

In embodiments (1) to (4), $R_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC$(CH_3)_3$, or together with and the —CONH-group at the C-3' position a carbamate formed from any of said alkyl, alkenyl, cycloalkyl, cycloalkenyl, aryl, or a nitrogen-containing heterocyclic and an oxygen atom.

Preferably, $R_4$ is propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl.

More preferably, $R_4$ is t-butoxy, iso-butenyl, propenyl, thiophenyl, thiazolyl or furyl.

In embodiments (1) and (2), $R_5$ is the linking group and $R_6$ has the same definition as above for $R_2$ for embodiments (1), (2) and (4).

In embodiment (3), $R_5$ has the same definition as above for $R_2$ for embodiments (1), (2) and (4).

In embodiment (3), $R_6$ has the same definition as above for $R_2$ for embodiments (1), (2) and (4).

In embodiment (4), $R_6$ is a linking group, and $R_5$ has the same definition as above for $R_2$ for embodiments (1), (2) and (4).

Suitable linking groups are well known in the art and include those which will form disulfide links, thioether links, acid labile links, photolabile links, peptidase labile links and esterase labile links. Preferred are those which will form disulfide links and thioether links.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —$(CR_{13}R_{14})_m(CR_{15}R_{16})_n(OCH_2CH_2)_y$SZ, —$CO(CR_{13}R_{14})_m(CR_{15}R_{16})_n(OCH_2CH_2)_y$SZ, —$(CR_{13}R_{14})_m$ $(CR_{17}=CR_{18})(CR_{15}R_{16})_m OCH_2CH_2)_y$SZ, —CO—$(CR_{13}R_{14})_m(CR_{17}=CR_{18})(CR_{15}R_{16})_m$ $(OCH_2CH_2)_y$, SZ, —$CONR_{12}(CR_{13}R_{14})_m(CR_{15}R_{16})_n$ $(OCH_2CH_2)_y$SZ, furyl-XSZ, oxazolyl-XSZ, thiazolyl-XSZ, thiopheneyl-XSZ, imidazolyl-XSZ, morpholino-XSZ, -piperazino-XSZ, piperidino-XSZ, CO-furyl-XSZ, CO-thiopheneyl-XSZ, CO-thiazolyl-XSZand —CO—N-methylpiperazino-XSZ, —CO-morpholino-XSZ, —CO-piperazino-XSZ, —CO-piperidino-XSZ, and —CO—N-methylpiperazino-XSZ, wherein:

Z is H or SR,

X is linear alkyl or branched alkyl having from 1 to 10 carbon atoms or a polyethylene glycol spacer with 2 to 20 repeating ethylene oxy units;

R and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or linear or branched alkyl having from 1 to 4 carbon atoms, $R_{17}$ and $R_{18}$ are H or methyl, n is an integer from 1 to 10, m is an integer from 1 to 10 and can also be 0, y is an integer from 1 to 20 and can also be 0.

Figure 3:
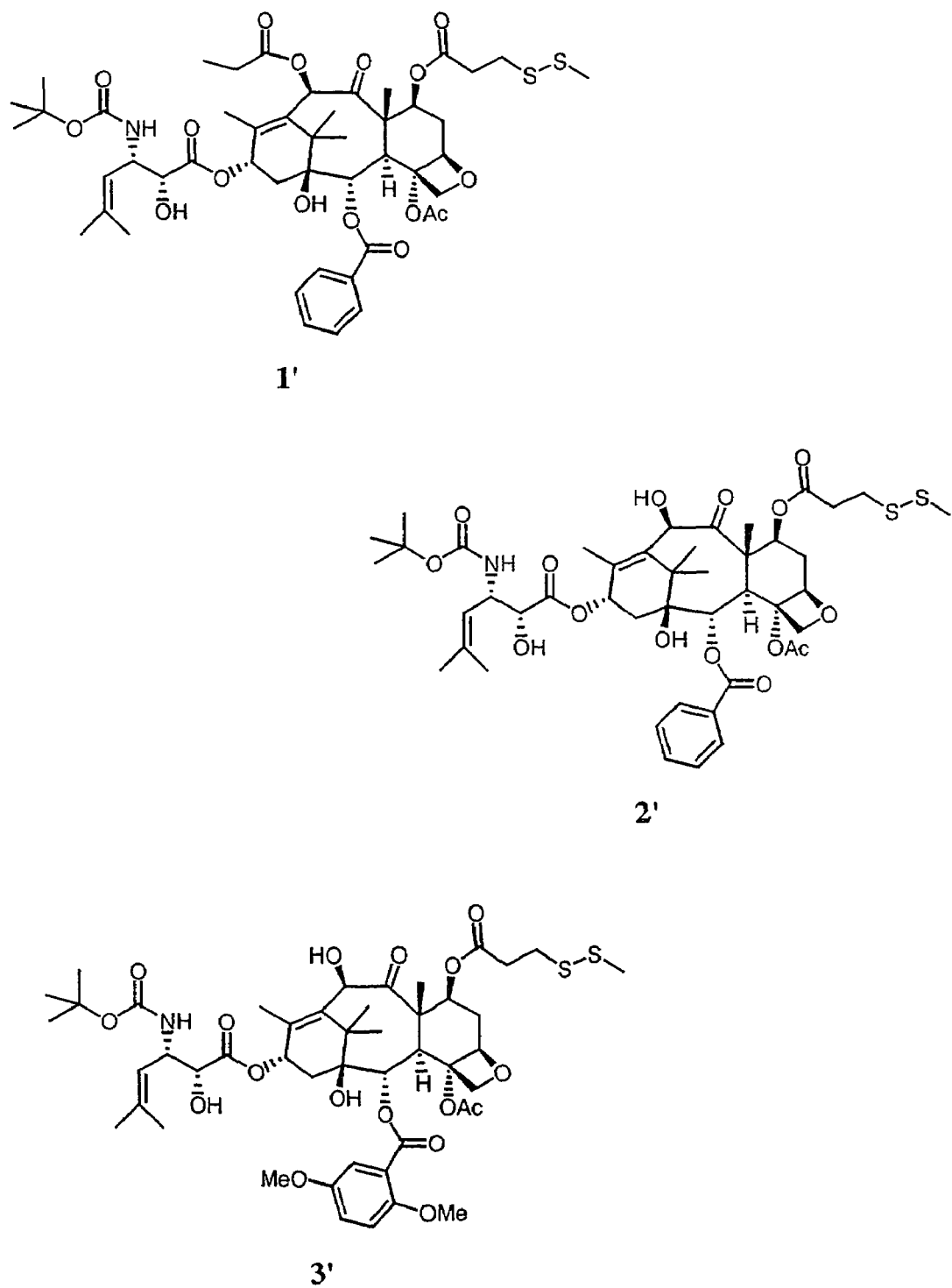
Figure 4:
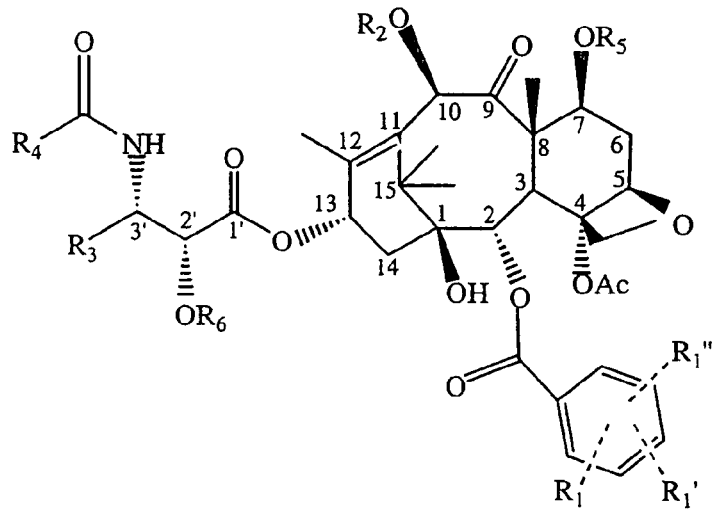

The preferred taxanes of the first aspect of the present invention are those bearing a free hydroxyl group at C-10 (i.e. $R_2$) and a linking group at C-7 (i.e. $R_5$). The most preferred taxanes of the present invention are taxanes 2' and 3' shown in FIG. 3.

Embodiments (5) to (9)

In embodiments (5) to (9), $R_1$ is H, an electron-withdrawing group, such as F, $NO_2$, CN, Cl, $CHF_2$ and $CF_3$ or an electron donating group such as —$OCH_3$, —$OCH_2CH_3$, —$NR_7R_8$ and —$OR_9$. $R_1'$ and $R_1''$ are the same or different and are H, an electron withdrawing group, such as F, $NO_2$, CN, Cl, $CHF_2$ and $CF_3$ or an electron donating group such as —$OCH_3$, —$OCH_2CH_3$, —$NR_7R_8$ and —$OR_9$.

$R_7$ and $R_8$ are the same or different and are linear, branched, or cyclic alkyl groups having 1 to 10 carbon atoms or simple or substituted aryl. Preferably the number of carbon atoms for $R_7$ and $R_8$ is 1 to 4. Also, preferably $R_7$ and $R_8$ are the same. Examples of preferred —$NR_7R_8$ groups include dimethyl amino, diethyl amino, dipropyl amino, di-isopropylamino and dibutyl amino, where the butyl moiety is any of primary, secondary, tertiary and isobutyl.

$R_9$ is linear, branched or cyclic alkyl having 1 to 10 carbon atoms.

Preferably, $R_1$ is —$OCH_3$, Cl, F, $NO_2$ and $CF_3$.

More preferably, $R_1$ is —$OCH_3$ and in the meta position, and one of $R_{1'}$ and $R_1''$ is —$OCH_3$ and the other is H.

In embodiments (5), (6) and (7), $R_3$ and $R_4$ are the same or different and are alkyl having from 1 to 10 carbon atoms, alkenyl having from 2 to 10 carbon atoms, cycloalkyl or cycloalkenyl having from 3 to 10 carbon atoms, aryl, or heterocyclic and $R_4$ additionally is —$OC(CH_3)_3$, or together with the —CONH— group at the C-3' position, a carbamate formed from any of said alkyl, alkenyl, cycloalkyl, or cycloalkenyl, aryl, or a nitrogen-containing heterocyclic and an oxygen atom.

Preferably, one or both of $R_3$ and $R_4$ are propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothipheneyl.

More preferably, one or both of $R_3$ and $R_4$ are t-BOC, iso-butenyl, propenyl, thiophenyl, thiazolyl or furyl.

In embodiments (8) and (9), $R_2$, $R_5$ and $R_6$ are the same or different and are H, or together with the oxygen atoms at the C-10, C-7 and C-2' positions, respectively, a heterocyclic or aryl ether, a heterocyclic or aryl ester, or a heterocyclic or aryl carbamate, a linear, branched or cyclic alkyl ester having from 1 to 10 carbon atoms in the alkyl, a linear, branched or cyclic alkenyl ester having from 2 to 10 carbon atoms in the alkenyl, a linear, branched or cyclic alkyl ether having from 1 to 10 carbon atoms, a linear, branched or cyclic alkenyl ether having from 2 to 10 carbon atoms, a carbamate of the formula —OCOX, wherein X is a nitrogen-containing heterocyclic, such as piperidino, morpholino, piperazino and N-methylpiperazino, or a carbamate of the formula —$OCONR_{10}R_{11}$, wherein $R_{10}$ and $R_{11}$ are the same or different and are H, linear, branched or cyclic alkyl having 1 to 10 carbon atoms or simple or substituted aryl.

Preferred examples of aryl ethers, esters and carbamates include phenyl and naphthyl ethers, esters and carbamates.

Preferred examples of alkyl and alkenyl esters include —$OCOCH_3$, —$OCOCH_2CH_3$, crotonyl and dimethylacryloyl. Preferred examples of alkyl and alkenyl ethers include methyl, ethyl, allyl, propyl, propenyl and isobutenyl ethers. Preferred examples of carbamates include —$OCONHCH_2CH_3$, —OCO-morpholino, —OCO-piperazino, and —OCO—N-methylpiperazino.

Preferably, $R_6$ is H and one of $R_2$ and $R_5$ is H.

In embodiment (5), $R_2$ is the linking group, and $R_5$ and $R_6$ have the same definition as for embodiments (8) and (9).

In embodiment (6), $R_5$ is the linking group, and $R_2$ and $R_6$ have the same definition as for embodiments (8) and (9).

In embodiment (7), $R_6$ is the linking group or H, and $R_2$ and $R_5$ have the same definition as for embodiments (8) and (9).

In embodiment (8), $R_3$ is the linking group, and $R_4$ has the same definition for embodiments (5), (6) and (7).

In embodiment (9), $R_4$ is the linking group, and $R_3$ has the same definition as for embodiments (5), (6) and (7).

Suitable linking groups are well known in the art and include the groups that will form disulfide links, thioether links, acid labile links, photolabile links, peptidase labile links and esterase labile links. Preferred are those that will form disulfide links and thioether links. When the linking group is a thiol- or disulfide-containing group, the side chain carrying the thiol or disulfide group can be linear or branched alkyl, alkenyl, cycloalkenyl, aromatic or heterocyclic or a polyethylene glycol. One of ordinary skill in the art can readily identify suitable side chains.

Specific examples of the thiol- or disulfide-containing substituents include —$(CR_{13}R_{14})_m(CR_{15}R_{16})_n(OCH_2CH_2)_y$SZ, —$CO(CR_{13}R_{14})_m(CR_{15}R_{16})_n(OCH_2CH_2)_y$SZ, —$(CR_{13}R_{14})_m$ $(CR_{17}=CR_{18})(CR_{15}R_{16})_m OCH_2CH_2)_y$SZ, —CO—$(CR_{13}R_{14})_m(CR_{17}=CR_{18})(CR_{15}R_{16})_m$ $(OCH_2CH_2)_y$, SZ, —$CONR_{12}(CR_{13}R_{14})_m(CR_{15}R_{16})_n$ $(OCH_2CH_2)_y$SZ, furyl-XSZ, oxazolyl-XSZ, thiazolyl-XSZ, thiopheneyl-XSZ, imidazolyl-XSZ, morpholino-XSZ, -piperazino-XSZ, piperidino-XSZ, CO-furyl-XSZ, CO-thiopheneyl-XSZ, CO-thiazolyl-XSZ and —CO—N-methylpiperazino-XSZ, —CO-morpholino-XSZ, —CO-piperazino-XSZ, —CO-piperidino-XSZ, and —CO—N-methylpiperazino-XSZ, wherein:

Z is H or SR,

X is a linear alkyl or branched alkyl having from 1 to 10 carbon atoms or a polyethylene glycol spacer with 2 to 20 repeating ethylene oxy units;

R and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or linear or branched alkyl having from 1 to 4 carbon atoms, $R_{17}$ and $R_{18}$ are H or methyl, n is an integer from 1 to 10, m is an integer from 1 to 10 and can also be 0, y is an integer from 1 to 20 and can also be 0.

The taxanes of the present invention can be synthesized according to known methods. The starting material for the synthesis is the commercially available 10-deacetylbaccatin III, shown in FIG. 7. The chemistry to introduce various substituents is described in several publications (Ojima et al, *J. Med. Chem.* 39: 3889-3896 (1996), Ojima et al., *J. Med. Chem.* 40: 267-278 (1997); I. Ojima et al., *Proc. Natl. Acad. Sci.*, 96: 4256-4261 (1999); I. Ojima et al., U.S. Pat. No. 5,475,011 and U.S. Pat. No. 5,811,452). The preparation of representative taxanes of the present invention is described in the Examples below.

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. High cytotoxicity is defined as exhibiting a toxicity having an $IC_{50}$ in the range of $1\times10^{-12}$ to $3\times10^{-9}$ M, when measured in vitro with cultured cancer cells upon a 72 hour exposure time to the drug. One of ordinary skill in the art can determine the appropriate chemical moiety for $R_1$ and the appropriate position for $R_1$ using only routine experimentation.

For example electron donating groups at the meta position are expected to increase the cytotoxic potency, while substitution at the para position is not expected to increase the potency as compared to the parent taxane. Typically a few representative taxanes with substituents at the different positions (ortho, meta and para) will be prepared initially and evaluated for in vitro cytotoxicity.

Figure 5:
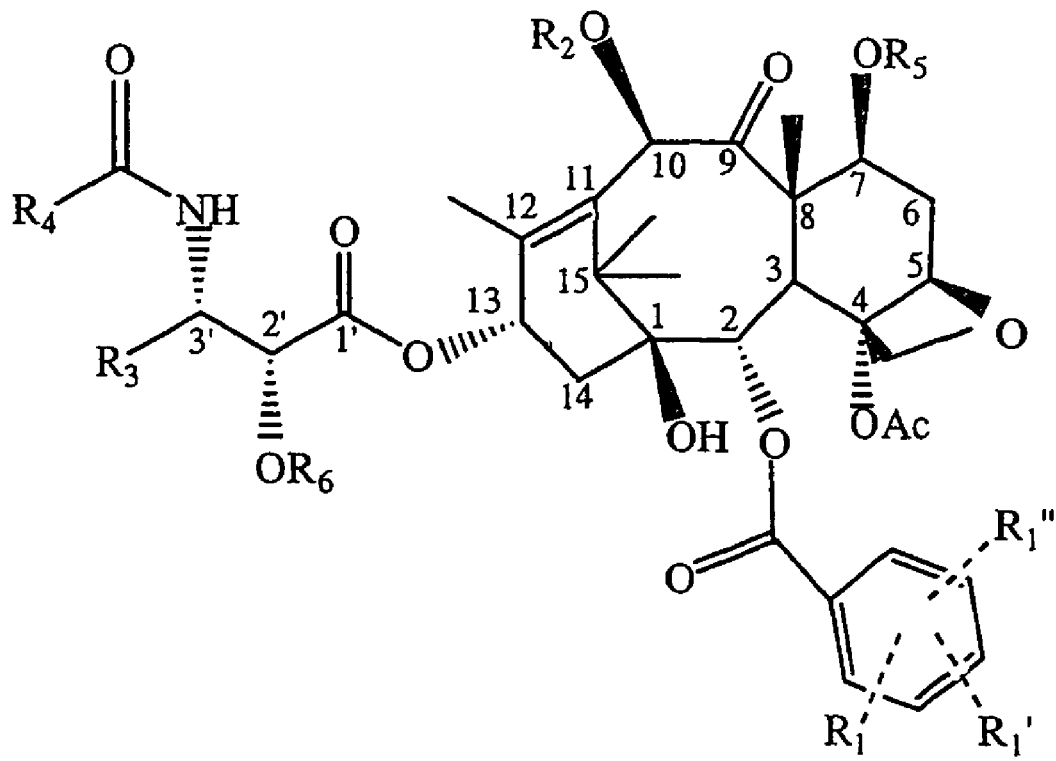

The new taxoids described in FIGS. 5 and 16 can be prepared by the β-lactam synthon method (Ojima, I.; Habus, I.; Zhao, M.; Zucco, M.; Park, Y. H.; Sun, C. M.; Brigaud, T. Tetrahedron, 48: 6985 (1992); Holton, R. A.; Biediger, R. J.; Boatman, P. D. in Taxol: Science and Applications; Suffness, M., Ed.; CRC: Boca Raton, 1995, p. 97) using appropriately derivatized baccatin III analog (7) and β-lactams as starting materials. The β-lactams 4-6d, 19-25 and 38-44 can be prepared by previously described methods (Brieva, R. Crich, J. Z.; Sih, C. J. J. Org. Chem., 58: 1068 (1993); Palomo, C.; Arrieta, A.; Cossio, F.; Aizpurua, J. M.; Mielgo, A.; Aurrekoetxea, N. Tetrahedron Lett., 1990, 31, 6429). The baccatin III analog (7) can be prepared using the commercially available 10-deacetylbaccatin III (10-DAB) (FIG. 7) as starting material.

The β-lactams 6a-d, 21-25 and 40-44 can be coupled with the baccatin III analog (7) in the presence of NaH or LiHMDS to give protected taxoids 8-11, 26-30 and 45-49. The silyl protecting groups can be finally deprotected in the presence of HF-pyridine to yield the desired taxanes 12-15, 31-35, and 50-54 (FIGS. 16a, 16b and 16c).

Disulfide-containing taxoids of the present invention (FIGS. 6 and 17) can be synthesized from the intermediates described above (8-11, 26-30, 45-49). The C-10 acetate can be removed successfully with hydrazine monohydrate. The reesterification of the C-10 position can then be carried out in the presence of EDC (1-[3-(dimethylamino)propyl-3-ethylcarbodiimide hydrochloride) employing the carbodiimide based coupling protocol using the required disulfide derivatives of the carboxylic acids. The coupled products can be deprotected with HF-pyridine to give the desired disulfide-containing taxoids (FIGS. 17a and 17b).

The disulfide or thiol-containing substituent can also be introduced at one of the other positions where a hydroxyl group already exists. The chemistry to protect the various hydroxyl groups, while reacting the desired one, has been described previously (see, for example, the references cited, supra). The substituent is introduced by simply converting the free hydroxyl group to a disulfide-containing ether, a disulfide-containing ester, or a disulfide-containing carbamate. Alternatively, a polyethylene glycol spacer may be introduced between the disulfide or thiol substituent and the hydroxy group that is being derivatized. (See, for example, U.S. application Ser. No. 10/144,042, filed May 14, 2002) This transformation is achieved as follows. The desired hydroxyl group is deprotonated by treatment with the commercially available reagent lithium hexamethyldisilazane (1.2 equivalents) in tetrahydrofuran at −40° C. as described in I. Ojima et al, supra. The resulting alkoxide anion is then reacted with an excess of a dihalo compound, such as dibromoethane, to give a halo ether. Displacement of the halogen with a thiol (by reaction with potassium thioacetate and treatment with mild base or hydroxylamine) will provide the desired thiol-containing taxane. The thiol group can be converted into a methyl or pyridyl disulfide by reaction with methyl methane thiolsulfonate or dithiodipyridine respectively. This method is described in U.S. Pat. No. 5,416,064.

The desired hydroxyl group can also be esterified directly by reaction with an acyl halide, such as 3-bromopropionyl chloride to give a bromo ester. Displacement of the bromo group by treatment with potassium thioacetate and further processing as described above will provide the thiol or disulfide-containing taxane ester. In order to prepare disulfide-containing carbamates, the hydroxyl group can be reacted with a commercially available chloroformate, such as para-nitrophenyl chloroformate, followed by reaction with an amino alkyl disulfide (e.g., methyldithio cysteamine).

Alternatively, the thiol or disulfide substituent can be incorporated into the β-lactam subunit, which is then reacted with the appropriately protected 10-deacetylbaccatin III to give the desired taxanes bearing a thiol or disulfide linking group at the C-3' position.

The new taxanes and the disulfide containing taxane drugs of the invention can be evaluated for their ability to suppress proliferation of human tumor cell lines in vitro. The human tumor cell lines A-549 (human lung carcinoma) and MCF-7 (human breast tumor, are used for the assessment of cytotoxicity of these compounds. Cells are exposed to the compounds for 72 hours and the surviving fractions of cells are measured in direct plating efficiency assays as previously described (Goldmacher et al, *J. Cell. Biol.* 102: 1312-1319 (1986) and $IC_{50}$ values are then calculated from this data.

The results of the in vitro cytotoxicity measurement of taxoids and disulfide-containing taxoids according to the second aspect of the present invention are shown in FIGS. 18 and 19. FIG. 18 shows the results of the cytotoxicity determination of twelve new taxanes of the present invention. Except for taxane 52, which bears a phenyl substituent at $R_4$, all the other new taxanes were extremely potent towards both A-549 and MCF-7 cell lines with $IC_{50}$ values in the $10^{-10}$ to $10^{-11}$ M range. Taxane 52 was less cytotoxic with an $IC_{50}$ value of $3\times10^{-9}$ M towards both cell lines that were tested. Similarly, disulfide-containing taxoids of the present invention are also extremely potent toward both A-549 and MCF-7 cells and display steep killing curves (FIG. 19).

The effectiveness of the compounds of the invention as therapeutic agents depends on the careful selection of an appropriate cell-binding agent. Cell-binding agents may be of any kind presently known, or that become known and include peptides and non-peptides. Generally, these can be antibodies, or fragments thereof, (especially monoclonal antibodies), lymphokines, hormones, growth factors, vitamins, nutrient-transport molecules (such as transferring, or any other cell-binding molecule or substance.

More specific examples of cell-binding agents that can be used include:

fragments of antibodies such as sFv, Fab, Fab', and F(ab')$_2$ (Parham, *J. Immunol.* 131: 2895-2902 (1983); Spring et al, *J. Immunol.* 113: 470-478 (1974); Nisonoff et al, *Arch. Biochem. Biophys.* 89: 230-244 (1960));

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

vitamins such as folic acid;

growth factors and colony-stimulating factors such as EGF, TGF-α, G-CSF, M-CSF and GM-CSF (Burgess, *Immunology Today* 5: 155-158 (1984)); and transferrin (O'Keefe et al, *J. Biol. Chem.* 260: 932-937 (1985)).

Monoclonal antibody techniques allow for the production of extremely specific cell-binding agents in the form of specific monoclonal antibodies or fragments thereof. Particularly well known in the art are techniques for creating monoclonal antibodies, or fragments thereof, by immunizing mice, rats, hamsters, or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies, or fragments thereof, is the use of phage libraries of sFv (single chain variable region), specifically human sFv. (See e.g., Griffiths et al., U.S. Pat. No. 5,885,793; McCafferty et al., WO 92/01047; Liming et al., WO 99/06587.)

Selection of the appropriate cell-binding agent is a matter of choice that depends upon the particular cell population to be targeted, but in general monoclonal antibodies are preferred if an appropriate one is available.

For example, the monoclonal antibody MY9 is a murine IgG$_1$ antibody that binds specifically to the CD33 antigen (J. D. Griffin et al *Leukemia Res.*, 8: 521 (1984)) which can be used if the target cells express CD33, such as in the disease of acute myelogenous leukemia (AML). Similarly, the monoclonal antibody anti-B4 is a murine IgG$_1$ that binds to the CD19 antigen on B cells (Nadler et al, *J. Immunol.* 131: 244-250 (1983)) and can be used if the target cells are B cells or diseased cells that express this antigen, such as in non-Hodgkin's lymphoma or chronic lymphoblastic leukemia. Similarly, the antibody N901 is a murine monoclonal IgG$_1$ antibody that binds to CD56 found on small cell lung carcinoma cells and on cells of other tumors of neuroendocrine origin (Roy et al. *J. Nat. Cancer Inst.* 88:1136-1145 (1996)).

Antibodies that target solid tumors are also useful, such as the C242 antibody which binds to a carbohydrate antigen found on MUC1 present on pancreatic and colorectal tumors. (U.S. Pat. No. 5,552,293); antibody J591, which binds to PSMA (prostate specific membrane antigen) which is expressed on prostate cancer cells and on endothelial cells of neovasculature in tumors (U.S. Pat. No. 6,107,090, He Liu et al. *Cancer Res.* 57: 3629-3634 (1997); and antibodies to HER-2, which is overexpressed on certain breast tumors. Examples of anti-HER-2 antibodies are the TA1 antibody (L. A. Maier et al. *Cancer Res.* 51: 5361-5369 (1991)) and the 4D5 antibody (U.S. Pat. Nos. 6,387,371 and 6,399,063).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes can be used for the treatment of melanoma.

Folic acid, which targets the folate receptor expressed on ovarian and other cancers, is also a suitable cell-binding agent.

Cancers of the breast and testes can be successfully targeted with estrogen (or estrogen analogues) or androgen (or androgen analogues), respectively, as cell-binding agents.

Conjugates of the taxanes of the invention and a cell-binding agent can be formed using any techniques presently known or later developed. Numerous methods of conjugation are taught in U.S. Pat. Nos. 5,416,064 and 5,475,092. The taxane ester can be modified to yield a free amino group and then linked to an antibody or other cell-binding agent via an acid labile linker or a photolabile linker. The taxane ester can be condensed with a peptide and subsequently linked to a cell-binding agent to produce a peptidase labile linker. The hydroxyl group on the taxane ester can be succinylated and linked to a cell-binding agent to produce a conjugate that can be cleaved by intracellular esterases to liberate free drug. Most preferably, the taxane ethers, esters, or carbamates are treated to create a free or protected thiol group, and then the disulfide- or thiol-containing taxanes are linked to the cell-binding agent via disulfide bonds.

Representative conjugates of the invention are antibody-taxane, antibody fragment-taxane, epidermal growth factor (EGF)-taxane, melanocyte stimulating hormone (MSH)-taxane, thyroid stimulating hormone (TSH)-taxane, estrogen-taxane, estrogen analogue-taxane, androgen-taxane, androgen analogue-taxane, and folate-taxane.

Taxane conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), 2-iminothiolane, or S-acetylsuccinic anhydride by known methods. See, Carlsson et al, *Biochem. J.* 173: 723-737 (1978); Blattler et al, *Biochem.* 24: 1517-1524 (1985); Lambert et al, *Biochem.* 22: 3913-3920 (1983); Klotz et al, *Arch. Biochem. Biophys.* 96: 605 (1962); and Liu et al, *Biochem.* 18: 690 (1979), Blakey and Thorpe, *Antibody, Immunoconjugates & Radiopharmaceuticals*, 1: 1-16 (1988), Worrell et al *Anti-Cancer Drug Design* 1: 179-184 (1986). The free or protected thiol-containing cell-binding agent thus derived is then reacted with a disulfide- or thiol-containing taxane to produce conjugates. The conjugates can be purified by HPLC or by gel filtration.

Similarly, for example, estrogen and androgen cell-binding agents such as estradiol and androstanediol can be esterified at the C-17 hydroxy group with an appropriate disulfide containing carboxylic acid using e.g., dicyclohexylcarbodiimide as a condensing agent. Examples of such carboxylic acids that can be employed are 3-(2-pyridyldithio) propanoic acid, 3-methyldithiopropanoic acid, 4-(2-pyridyldithio) pentanoic acid, and 3-phenyldithiopropanoic acid. Esterification of the C-17 hydroxy group can also be achieved by reaction with an appropriately protected thiol group containing carboxylic acid chloride such as 3-S-acetylpropanoyl chloride. Other methods of esterification can also be employed as described in the literature (Haslam, *Tetrahedron* 36: 2409-2433 (1980)). The protected or free thiol-containing androgen or estrogen can then be reacted with a disulfide- or thiol-containing taxane to produce a conjugate. The conjugate can be purified by column chromatography on silica gel or by HPLC. Folic acid can be condensed with a suitable hydrazide such as 4-(2-pyridyldithio) pentanoic acid hydrazide in the presence of a condensing agent such as dicyclohexyl carbodiimide to give a hydrazone containing an active disulfide. The disulfide-containing folate can then be reacted with a thiol-containing taxane to produce a conjugate that can be purified by column chromatography over silica gel or by HPLC.

Preferably, monoclonal antibody- or cell-binding agent-taxane conjugates are those that are joined via a disulfide bond, as described above, that are capable of delivering taxane molecules. Such cell-binding conjugates are prepared by known methods such as by modifying monoclonal antibodies with succinimidyl pyridyl-dithiopropionate (SPDP) (Carlsson et al, *Biochem. J.* 173: 723-737 (1978)). The resulting thiopyridyl group is then displaced by treatment with thiol-containing taxanes to produce disulfide linked conjugates. Alternatively, in the case of the aryldithio-taxanes, the formation of the cell-binding conjugate is effected by direct displacement of the aryl-thiol of the taxane by sulfhydryl groups previously introduced into antibody molecules. Conjugates containing 1 to 10 taxane drugs linked via a disulfide bridge are readily prepared by either method.

More specifically, a solution of the dithiopyridyl modified antibody at a concentration of 1 mg/ml in 0.1 M potassium phosphate buffer, at pH 6.5 containing 1 mM EDTA is treated with the thiol-containing taxane (1.25 molar eq./dithiopyridyl group). The release of thiopyridine from the modified antibody is monitored spectrophotometrically at 343 nm and is complete in about 20 hours. The antibody-taxane conjugate is purified and freed of unreacted drug and other low molecular weight material by gel filtration through a column of Sephadex G-25 or Sephacryl S300. The number of taxane moieties bound per antibody molecule can be determined by measuring the ratio of the absorbance at 230 nm and 275 nm. An average of 1 to 10 taxane molecules/antibody molecule can be linked via disulfide bonds by this method.

Antibody-taxane conjugates with non-cleavable links can also be prepared. The antibody can be modified with crosslinking reagents such as N-sucinimidyl 4-(maleimidomethyl)cyclohexane-1-carboxylate (SMCC), sulfo-SMCC, N-succinimidyl 4-maleimidobutyrate (SMB), sulfo-SMB, N-succinimidyl 6-maleimidocaproate (SMC), sulfo-SMC, m-maleimidobenzoyl-N-hydroxysuccinimide ester (MBS), sulfo-MBS or succinimidyl-iodoacetate, as described in the literature, to introduce 1-10 reactive groups. See, Yoshitake et al, *Eur. J. Biochem.* 101: 395-399 (1979); Hashida et al, *J. Applied Biochem.* 6: 56-63 (1984); and Liu et al, *Biochem.* 18: 690-697 (1979). The modified antibody is then reacted with the thiol-containing taxane derivative to produce a conjugate. The conjugate can be purified by gel filtration through a Sephadex G-25 column.

The modified antibodies, or fragments thereof, are treated with the thiol-containing taxanes (1.25 molar equivalent/maleimido group). The mixtures are incubated overnight at about 4° C. The antibody-taxane conjugates are purified by gel filtration through a Sephadex G-25 column. Typically, an average of 1 to 10 taxanes is linked per antibody.

A preferred method is to modify antibodies, or fragments thereof, with succinimidyl-4-(maleimidomethyl)-cyclohexane-1-carboxylate (SMCC) to introduce maleimido groups followed by reaction of the modified antibody or fragment with the thiol-containing taxanes to give a thioether linked conjugate. Again, conjugates with 1 to 10 drug molecules per antibody molecule result.

Cytotoxicity of antibody conjugates of these taxoids to non-adherent cell lines such as Namalwa and HL-60 can be measured by back-extrapolation of cell proliferation curves as described in Goldmacher et al, *J. Immunol.* 135: 3648-3651 (1985). Cytotoxicity of these compounds to adherent cell lines such as SKBR₃ and A431 can be determined by clonogenic assays as described in Goldmacher et al, *J. Cell Biol.* 102: 1312-1319 (1986).

The present invention also provides a therapeutic composition comprising:
  (a) an effective amount of one or more taxanes linked to a cell-binding agent, and
  (b) a pharmaceutically acceptable carrier, diluent, or excipient.

Similarly, the present invention provides a method for inducing cell death in selected cell populations comprising contacting target cells or tissue containing target cells with an effective amount of a cytotoxic agent comprising one or more taxanes linked to a cell-binding agent.

The cytotoxic agent is prepared as described above.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells:
  treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 100 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HUV infection, AIDS, etc.; and parasite infections, such as giardiasis, amoebiasis, schistosomiasis, and others as determined by one of ordinary skill in the art.

EXAMPLES

The invention will now be illustrated by reference to non-limiting examples. Unless otherwise stated, all percents, ratios, parts, etc. are by weight.

Example 1

Preparation of Taxane 2'

Figure 8:
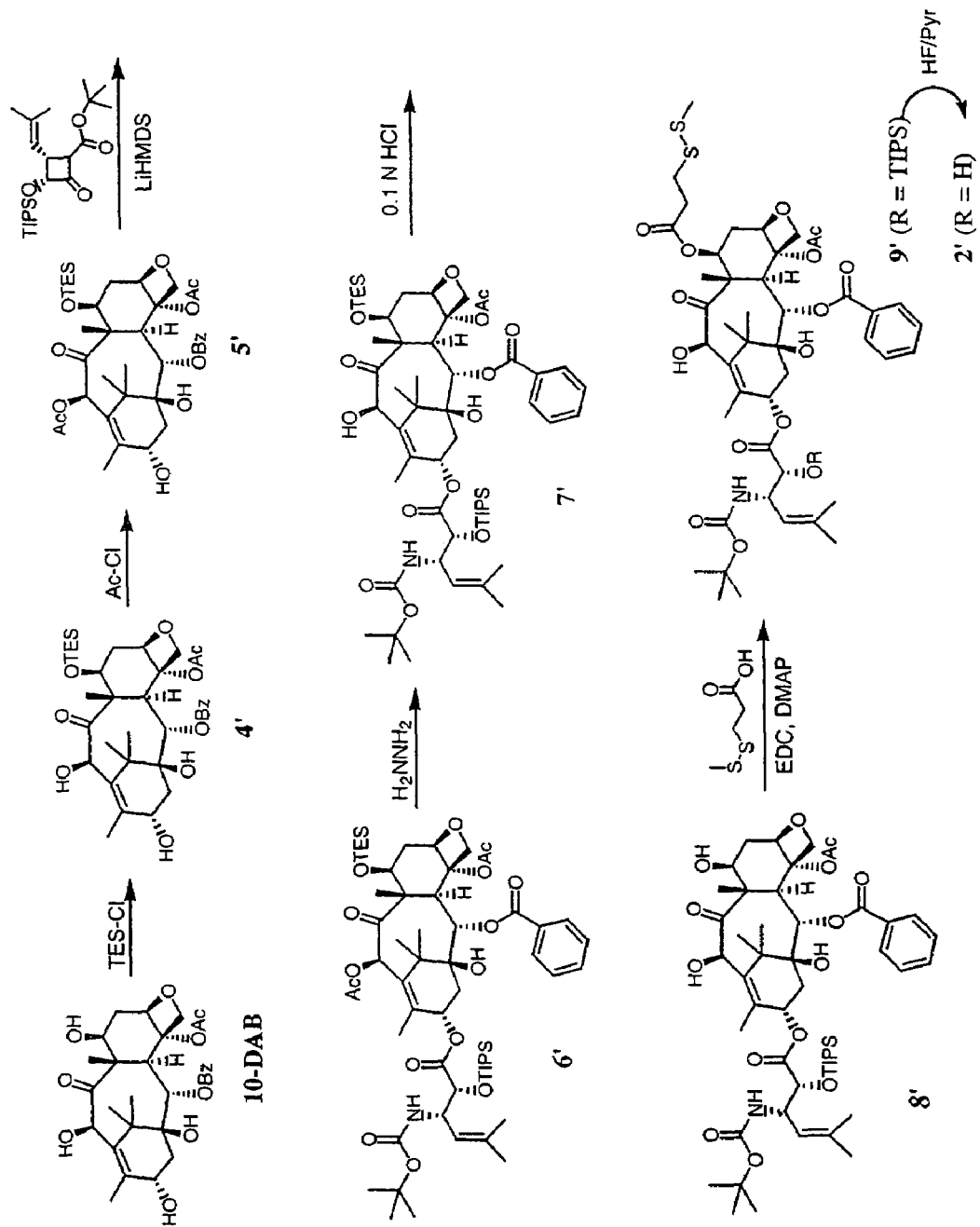

Taxane 2' (3'-dephenyl-3'-(isobutenyl)-7-(methyldisulfonyl-propanoyl)-docetaxel) was prepared from commercially available 10-deacetylbaccatin III (FIG. 7) following the scheme shown in FIG. 8.

Compounds 4-6' were prepared as described by Greene et al. in J. Am. Chem. Soc. 110: 5917-5919 (1988) and by Ojima et al, J. Med. Chem. 39: 3889-3896 (1996) and references cited therein.

Compound 7' (7-(triethylsilyl)-2'-(triisopropylsilyloxy)-3'-dephenyl-3'-(isobutenyl)-docetaxel) was prepared by adding hydrazine monohydrate (1 mL) to a solution of 6' (65 mg, 0.059 mmol) in ethanol (2 mL) at room temperature. The reaction was stirred at room temperature and monitored by thin layer chromatography using 40% ethyl acetate in hexane. After 1 hour the reaction was complete by thin layer chromatography and quenched with saturated aqueous ammonium chloride (10 mL). The aqueous layer was extracted with ethyl acetate (10 ml×3). The combined extracts were dried over anhydrous magnesium sulfate and concentrated in vacuo. The residue was purified on a silica gel column using 40% ethyl acetate in hexane as the eluant to afford product 7' as a white solid (42 mg, 69%): $^1$H NMR (CDCl$_3$) δ 0.53 (m, 6H), 0.92 (t, J=8.0 Hz, 9H), 1.11 (m, 24H), 1.20 (s, 3H), 1.23 (s, 3 H), 1.32 (s, 9H), 1.71 (s, 3H), 1.72 (m, 3H), 1.78 (s, 3H), 1.92 (m, 4H), 2.35 (m, 5H), 3.89 (d, J=6.8 Hz, 1H), 4.18 (d, J=8.4 Hz, 1H), 4.23 (d, J=2.0 Hz, 1H), 4.28 (d, J=8.4 Hz, 1H), 4.37 (dd, J=6.4, 10.4 Hz, 1H), 4.41 (d, J=3.2 Hz, 1H), 4.80 (m, 2H), 4.91 (d, J=8.0 Hz, 1H), 5.10 (d, J=2.0 Hz, 1H), 5.31 (d, J=8.8 Hz, 1H), 5.63 (d, J=7.2 Hz, 1H), 6.13 (t, J=9.0 Hz, 1H), 7.43 (t, J=8.0 Hz, 2H), 7.57 (t, J=8.0 Hz, 1 H), 8.07 (d, J=8.0 Hz 2H). m/z LC/MS for $C_{56}H_{89}NO_{14}Si_2Na^+$: calcd: 1078.58; found: 1078.40.

Compound 8' (2'-(triisopropylsilyloxy)-3'-dephenyl-3'-(isobutenyl)-docetaxel) was prepared by the following steps. A solution of compound 7' (35 mg, 0.029 mmol) was made by adding a solution of 0.1 N HCl in ethanol (5 mL) at 0° C. The solution was stirred with gradual warming to room temperature and allowed to stir for 16 hrs. The reaction was quenched with saturated aqueous sodium bicarbonate (10 mL), and the aqueous layer was extracted with ethyl acetate (15 ml×3). The combined extracts were dried over anhydrous magnesium sulfate and concentrated in vacuo. The residue was purified on a silica gel column using 50% ethyl acetate in hexane as the eluant to afford product 8' as a white solid (20 mg, 64%): $^1$H NMR (CDCl$_3$) δ 1.11 (m, 24H), 1.23 (s, 3H), 1.26 (s, 3H), 1.30 (s, 9H), 1.74 (s, 6H), 1.79 (s, 3H), 1.84 (m, 1H), 1.92 (s, 3H), 2.36 (s, 3H), 2.38 (m, 1H), 2.57 (m, 1H), 3.92 (d, J=6.8 Hz, 1H), 4.17 (d, J=1.2 Hz, 1H), 4.22 (d, J=8.0 Hz, 1H), 4.23 (m, 1H), 4.31 (d, J=8.0 Hz, 1H), 4.42 (d, J=2.8 Hz, 1H), 4.75 (m, 1H), 4.85 (m, 1H), 4.95 (d, J=7.6 Hz, 1H), 5.20 (s, 1H), 5.33 (d, J=8.8 Hz, 1H), 5.68 (d, J=7.2 Hz, 1H), 6.14 (t, J=8.8 Hz, 1H), 7.46 (t, J=8.0 Hz, 2H), 7.60 (t, J=8.0 Hz, 1H), 8.10 (d, J=8.0 Hz, 1 H).

Compound 9' (2'-(triisopropylsilyloxy)-3'-dephenyl-3'-(isobutenyl)-7-(methyldisulfamyl-propanoyl)-docetaxel) was prepared by the following steps. To a solution of 8' (20 mg, 0.020 mmol) in methylene chloride (3 mL) was added DMAP (3 mg, 0.02 mmol), dithio acid (3 mg, 0.018 mmol) and EDC (8 mg, 0.042 mmol). The resulting mixture was stirred overnight. Thin layer chromatography analysis using 25% ethyl acetate in hexane revealed virtually all starting material was consumed and a new spot was present. The reaction was quenched with saturated aqueous ammonium chloride (10 mL) and extracted into methylene chloride (10 ml×3). The combined extracts were dried over anhydrous magnesium sulfate and concentrated in vacuo. The residue was purified on a silica gel column using 25% ethyl acetate in hexane as the eluant to afford 9' as a white solid (9 mg, 41%): $^1$H NMR (CDCl$_3$) δ 1.11 (m, 24H), 1.22 (s, 3H), 1.34 (s, 9H), 1.76 (s, 3H), 1.80 (s, 3 H), 1.85 (s, 3H), 1.95 (m, 4H), 2.36 (s, 3H), 2.41 (m, 1H), 2.42 (s, 3H), 2.54 (m, 1 H), 2.70 (t, J=7.2 Hz, 2H), 2.88 (m, 2H), 3.93 (br s, 1H), 4.04 (d, J=7.2 Hz, 1H), 4.24 (d, J=8.8 Hz, 1H), 4.33 (d, J=8.8 Hz, 1H), 4.43 (d, J=2.8 Hz, 1H), 4.77 (m, 1H), 4.86 (m, 1H), 4.94 (d, J=8.0 Hz, 1H), 5.32 (m, 2H), 5.54 (dd, J=6.8, 10.4 Hz, 1H), 5.69 (d, J=7.2 Hz, 1H), 6.13 (t, J=8.8 Hz, 1H), 7.47 (t, J=8.0 Hz, 2H), 7.61 (t, J=8.0 Hz, 1H), 8.10 (d, J=8.0 Hz 1H). m/z LC/MS for $C_{54}H_{81}NO_{15}S_2SiNa^+$: calcd: 1098.48; found: 1098.28.

Taxane 2' (3'-dephenyl-3'-(isobutenyl)-7-(methyldisulfonyl-propanoyl)-docetaxel) was prepared by the following steps. To a solution of 9' (9 mg, 0.008 mmol) in pyridine-acetonitrile (1/1, 2 mL) was added HF/pyridine (70:30, 0.1 mL) at 0° C., and the mixture was stirred for 24 hours with warming to room temperature. The reaction was quenched with saturated aqueous sodium bicarbonate. The reaction mixture was then diluted with ethyl acetate (5 mL×2), the combined organic layers were washed with water (5 mL), dried over anhydrous sodium sulfate and concentrated in vacuo. The residue was purified on a silica gel column using 60% ethyl acetate in hexane as the eluant to afford the final product 2' as a white solid (5 mg, 64%): $^1$H NMR (CDCl$_3$) δ 1.10 (s, 3H), 1.21 (s, 3H), 1.36 (s, 9H), 1.56 (s, 3 H), 1.77 (s, 6H), 1.86 (s, 3H), 1.94 (m, 1H), 1.97 (s, 3H), 2.35 (m, 1H), 2.37 (s, 3 H), 2.42 (s, 3H), 2.56 (m, 1H), 2.70 (t, J=7.2 Hz, 2H), 2.88 (dd, J=2.4, 6.8 Hz, 2 H), 3.36 (br d, J=4.8 Hz, 1H), 3.95 (d, J=3.2 Hz, 1H), 4.01 (d, J=6.8 Hz, 1H), 4.23 (m, 2H), 4.33 (d, J=8.4 Hz, 1H), 4.77 (m, 2H), 4.94 (d, J=7.6 Hz, 1H), 5.31 (m, 1H), 5.32 (d, J=1.6 Hz, 1H), 5.51 (dd, J=7.2, 10.8 Hz, 1H), 5.68 (d, J=7.2 Hz, 1H), 6.16 (d, J=9.0 Hz, 1H), 7.48 (t, J=8.0 Hz, 2H), 7.62 (t, J=8.0 Hz, 1H), 8.11 (d, J=8.0 Hz 1H).

m/z LC/MS for $C_{45}H_{61}NO_{15}S_2Na^+$: calcd: 942.35; found: 942.47.

Example 2

Preparation of Taxne 3'

Figure 9:
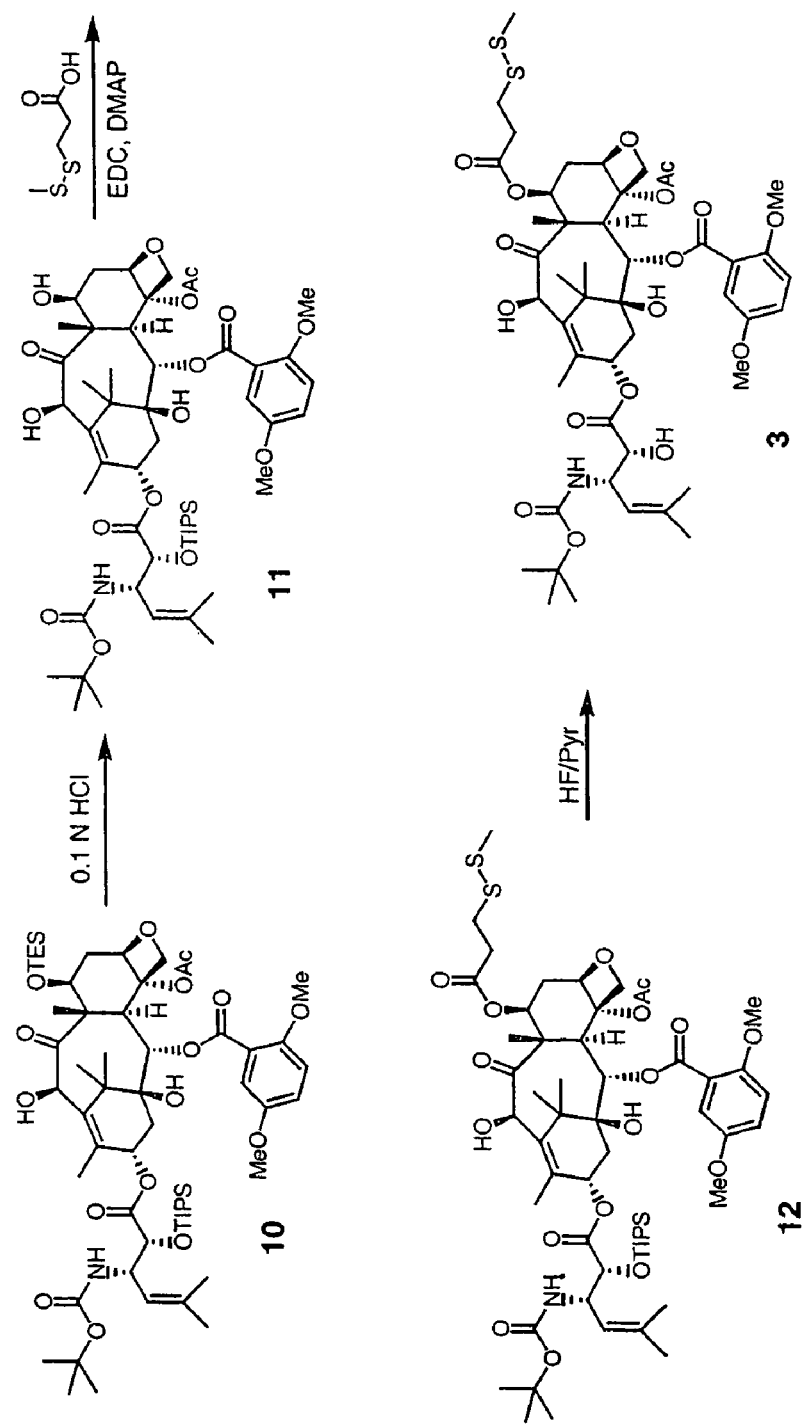

Taxane 3' (3'-dephenyl-3'-(isobutenyl)-2-debenzoyl-2-(2,5-dimethoxybenzoyl)-7-(methyldisulfonyl-propanoyl)-docetaxel) was prepared from compound 10' following the scheme shown in FIG. 9.

Compound 10' (7-(Triethylsilyl)-2'-(triisopropylsilyloxy)-3'-dephenyl-3'-(isobutenyl)-2-debenzoyl-2-(2,5-dimethoxybenzoyl)-docetaxel) was prepared by the following steps. To a solution of 9' (36 mg, 0.031 mmol) in ethanol (1.5 mL) was added hydrazine monohydrate (1 mL) at room temperature. The reaction was stirred at room temperature and monitored by thin layer chromatography using 40% ethyl acetate in hexane (developed twice). After 1 hour, the reaction was complete by thin layer chromatography and quenched with saturated aqueous ammonium chloride (10 mL). The aqueous layer was extracted with ethyl acetate (10 ml×3). The combined extracts were dried over anhydrous magnesium sulfate and concentrated in vacuo. The residue was purified on a silica gel column using 35% ethyl acetate in hexane as the eluant to afford the deacetylated product 10' as a white solid (19 mg, 57%): $^1$H NMR (CDCl$_3$) δ 0.56 (m, 6H), 0.92 (t, J=8.0 Hz, 9H), 1.11 (m, 27H), 1.22 (s, 3H), 1.23 (s, 3H), 1.38 (m, 10H), 1.69 (s, 3H), 1.72 (m, 3H), 1.78 (s, 3H), 1.89 (s, 3H), 1.93 (m, 1H), 2.18 (s, 3H), 2.32 (m, 1H), 2.44 (m, 2H), 3.81 (s, 3H), 3.82 (d, J=6.8 Hz, 1H), 3.96 (s, 3H), 4.25 (d, J=2.0 Hz, 1H), 4.29 (d, J=8.0 Hz, 1H), 4.34 (dd, J=6.4, 10.4 Hz, 1H), 4.39 (d, J=2.0 Hz, 1H), 4.42 (d, J=8.0 Hz, 1H), 4.76 (t, J=9.2 Hz, 1H), 4.89 (m, 2H), 5.11 (d, J=2.0 Hz, 1H), 5.34 (d, J=8.8 Hz, 1 H), 5.64 (d, J=6.4 Hz, 1H), 6.13 (t, J=9.0 Hz, 1H), 6.94 (d, J=9.2 Hz, 1H), 7.06 (dd, J=9.2, 3.2 Hz, 1H), 7.29 (d, J=2.8 Hz 1H). m/z LC/MS for $C_{58}H_{93}NO_{16}Si_2Na^+$: calcd: 1138.60; found: 1138.43.

Compound 11' (2'-(triisopropylsilyoxy)-3'-dephenyl-3'-(isobutenyl)-2-debenzoyl-2-(2,5-dimethoxybenzoyl)-docetaxel) was prepared by the following steps. A solution of 5% hydrochloric acid in ethanol (9.0 mL) was added to 10' (86.4 mg, 0.0774 mmol) at 0° C. The mixture was stirred under N$_2$, warming to room temperature. After 5 hours the reaction was quenched with saturated aqueous sodium bicarbonate and extracted into ethyl acetate (25 mL×2). The combined ethyl acetate layers were then washed with water (25 mL×2), dried over anhydrous magnesium sulfate and concentrated in vacuo. The crude residue was purified on a silica gel column with 50% ethyl acetate in hexanes as the eluant. Product 11' was isolated as a white solid (61.5 mg, 79%): $^1$H NMR (CDCl$_3$) δ 1.08 (s, 27H), 1.23 (s, 3H), 1.36 (s, 9H), 1.58 (m, 1H), 1.67 (s, 3H), 1.70 (s, 3H), 1.76 (s, 3H), 1.82 (m, 2H), 1.88 (s, 3 H), 2.16 (s, 3H), 2.31 (m, 1H), 2.50 (m, 2H), 3.17 (br s, 1H), 3.79 (s, 3 H), 3.85 (d, J=6.4 Hz, 1H), 3.95 (s, 1H), 4.18 (m, 2H), 4.29 (d, J=8.4 Hz, 1H), 4.37 (d, J=2 Hz, 1H), 4.41 (d, J=8.4 Hz, 1H), 4.74 (t, J=9 Hz, 1H), 4.90 (t, J=9.8 Hz, 2H), 5.17 (d, J=1.6 Hz, 1H), 5.32 (d, J=9.2 Hz, 1H), 5.65 (d, J=6.8 Hz, 1H), 6.10 (t, J=8.8 Hz, 1H), 6.93 (d, J=9.2 Hz, 1H), 7.05 (dd, J=9.2, 3.0 Hz, 1H), 7.28 (d, J=3.0 Hz, 1H). m/z LC/MS for $C_{52}H_{79}NO_{16}SiNa^+$: calcd: 1024.52; found: 1024.31.

Compound 12' (2'-(triisopropylsilyoxy)-3'-dephenyl-3'-(isobutenyl)-2-debenzoyl-2-(2,5-dimethoxybenzoyl)-7-(methyldisulfonyl-propanoyl)-docetaxel) was prepared by the following steps. To a solution of 11' (25 mg, 0.025 mmol), EDC (10 mg, 0.05 mmol) and DMAP (3 mg, 0.025 mmol) in methylene chloride (0.8 mL), a solution of methyldithiopropionic acid (3.6 mg, 0.024 mmol) in methylene chloride (4.0 mL) was added. The reaction was stirred under N$_2$ at room temperature for 5 hours. The reaction was quenched with saturated aqueous ammonium chloride and extracted into methylene chloride (25 mL×2). The combined organic layers were washed with water (15 mL×1), dried over anhydrous magnesium sulfate and concentrated in vacuo. The residue was purified on a silica gel column with 30% ethyl acetate in hexanes as the eluant yielding product 12' (21.3 mg, 75%): $^1$H NMR (CDCl$_3$) δ 1.12 (s, 27H), 1.23 (s, 6H), 1.37 (s, 9H), 1.68 (s, 3H), 1.72 (s, 3H), 1.88 (s, 3H), 1.93 (s, 3H), 2.17 (s, 3H), 2.41 (s, 3H), 2.69 (t, J=6.8 Hz, 2 H), 2.86 (m, 2 H) 3.22 (br s, 1H), 3.80 (s, 3H), 3.95 (m, 4H), 4.31 (d, J=8.0 Hz, 1H), 4.38 (d, J=2.4 Hz, 1H), 4.45 (d, J=8.4 Hz, 1H), 4.76 (t, J=9.8 Hz, 1H), 4.90 (m, 2 H), 5.29 (s, 1H), 5.34 (d, J=9.2 Hz, 1H), 5.48 (dd, J=7.2, 10.8 Hz, 1H), 5.66 (d, J=6.4 Hz, 1H), 6.11 (t, J=8.8 Hz, 1H), 6.95 (d, J=9.2 Hz, 1H), 7.06 (dd, J=3.2, 9.2 Hz, 1 H), 7.28 (d, J=3.2 Hz, 1H). m/z LC/MS for $C_{56}H_{85}NO_{17}S_2SiNa^+$: cacld: 1158.50; found: 1158.33.

Taxane 3' (3'-dephenyl-3'-(isobutenyl)-2-debenzoyl-2-(2,5-dimethoxybenzoyl)-7-(methyldisulfonyl-propanoyl)-docetaxel) was prepared by the following steps. Under N$_2$, compound 12' (27.6 mg, 0.0243 mmol) was dissolved in pyridine-acetonitrile (1/1, 2.0 mL). HF/pyridine (70:30, 0.28 mL) was added at 0° C. and the reaction stirred for 24 hours, warming to room temperature. The reaction was quenched with saturated aqueous sodium bicarbonate and extracted into ethyl acetate (30 mL×3). The combined organic layers were washed with additional saturated aqueous sodium bicarbonate (25 mL×1), followed by saturated aqueous cupric sulfate (25 mL×3). The combined organic layers were washed with water (25 mL×1), dried over anhydrous magnesium sulfate and concentrated in vacuo. The crude residue was purified on a silica gel column with 50% ethyl acetate in hexanes as the eluant, yielding 3' (19.7 mg, 82.8%): $^1$H NMR (CDCl$_3$) δ 1.25 (s, 6H), 1.38 (s, 9H), 1.69, (s, 3H), 1.74 (s, 3H), 1.87 (s, 3H), 1.94 (s, 3H), 2.18 (s, 3H), 2.41 (s, 3H), 2.68 (t, J=6.8 Hz, 2H), 2.86 (m, 2H), 3.12 (br s, 1H), 3.29 (d, J=6.4 Hz, 1H), 3.80 (s, 3H), 3.92 (m, 4H), 4.16 (d, J=2.0, 6.4 Hz, 1H), 4.30 (d, J=8.0 Hz, 1H), 4.43 (d, J=8.4 Hz, 1H), 4.75 (m, 2H), 4.90 (d, J=8.0 Hz, 1H), 5.29 (s, 1H), 5.33 (d, J=8.0 Hz, 1H), 5.46 (dd, J=7.2, 10.8 Hz, 1H), 5.65 (d, J=6.4 Hz, 1H), 6.14 (t, J=8.8 Hz 1H), 6.95 (t, J=9.2 Hz, 1H), 7.06 (dd, J=3.2, 9.2 Hz, 1H), 7.28 (d, J=3.2 Hz, 1H). m/z LC/MS for $C_{47}H_{65}NO_{17}S_2Na^+$: calcd: 1002.37; found 1001.99.

Example 3

In Vitro Cytotoxicity Assays

The sulfide, disulfide, and sulfhydryl containing taxane drugs of the invention can be evaluated for their ability to suppress proliferation of various human tumor cell lines in vitro. Four adherent cell lines, A431 (human epidermoid carcinoma), SKBR$_3$ (human breast tumor), A549 (human lung carcinoma) and MCF-7 (human breast tumor), and the non-adherent cell line, Namalwa (Burkitt's lymphoma) are used for the assessment of cytotoxicity of these compounds. Cells are exposed to the compounds for 72 hours and the surviving fractions of cells are measured in direct assays. A431, SKBR$_3$, A549 and MCF-7 are assayed for plating efficiency (Goldmacher et al, J. Cell. Biol. 102: 1312-1319 (1986) and Namalwa are assayed by growth back extrapolation (Goldmacher et al, J. Immunol. 135: 3648-3651 (1985). IC$_{50}$ values are then calculated from this data.

The cytotoxicity of taxanes 2' and 3' was measured as follows.

A431, A549 and MCF-7 cells were plated at different densities in 6-well tissue-culture plates in DMEM medium supplemented with 10% fetal calf serum. Taxane 2', at varying concentrations, was added and the cells were maintained in a humidified atmosphere at 37° C. and 6% $CO_2$ until colonies of approximately 20 cells or more were formed (6 to 10 days). Control plates contained no taxane. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

Figure 10:
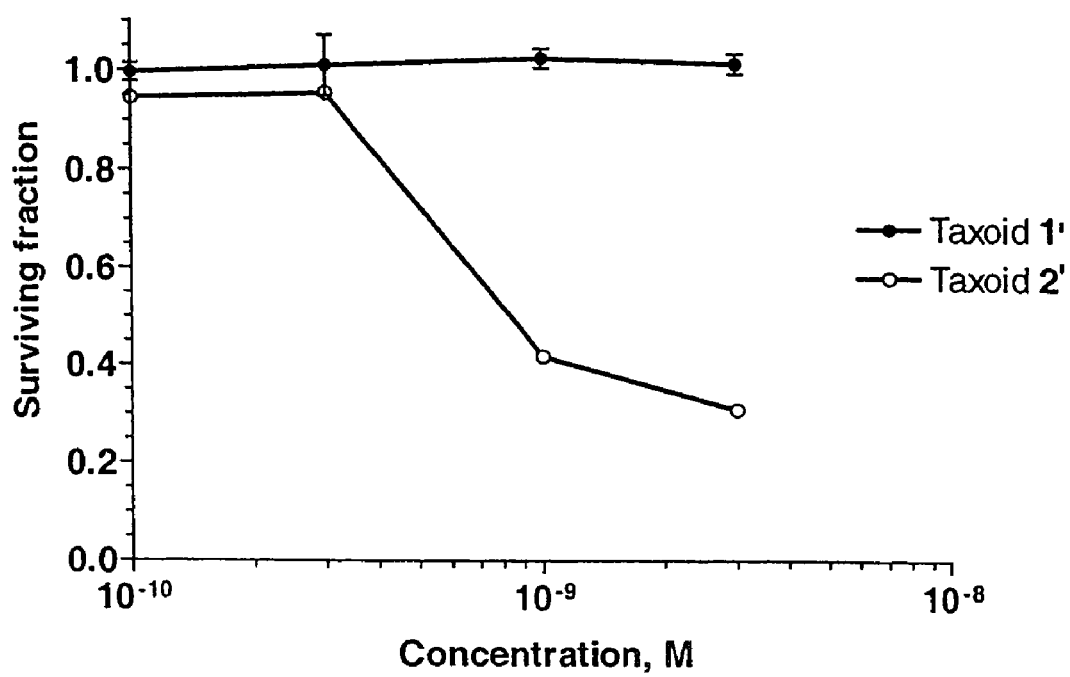
FIG. 10 shows a comparison of the in vitro potency of taxanes 1 and 2' towards A431 cells.

FIG. 10 shows the results of the cytotoxicity determination. Taxane 2' bearing a free hydroxy group at C-10 and a linking group at C-7 is highly potent with an $IC_{50}$ value of $8\times10^{-10}$ M towards A431 cells. In contrast, the corresponding taxane 1' (FIG. 3) that bears an ester group at C-10 is non-toxic to these cells even at $3\times10^{-9}$ M. These results demonstrate that the C-10 position of a taxane does not need to be protected to maintain high potency.

The cytotoxic potency of taxane 3' was similarly confirmed. A549 and MCF-7 cells were plated at different densities in 6-well tissue-culture plates in DMEM medium supplemented with 10% fetal calf serum. Taxane 2' at varying concentrations, was added and the cells were maintained in a humidified atmosphere at 37° C. and 6% $CO_2$ until colonies of approximately 20 cells or more were formed (6 to 10 days). Control plates contained no taxane. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

Figure 11:
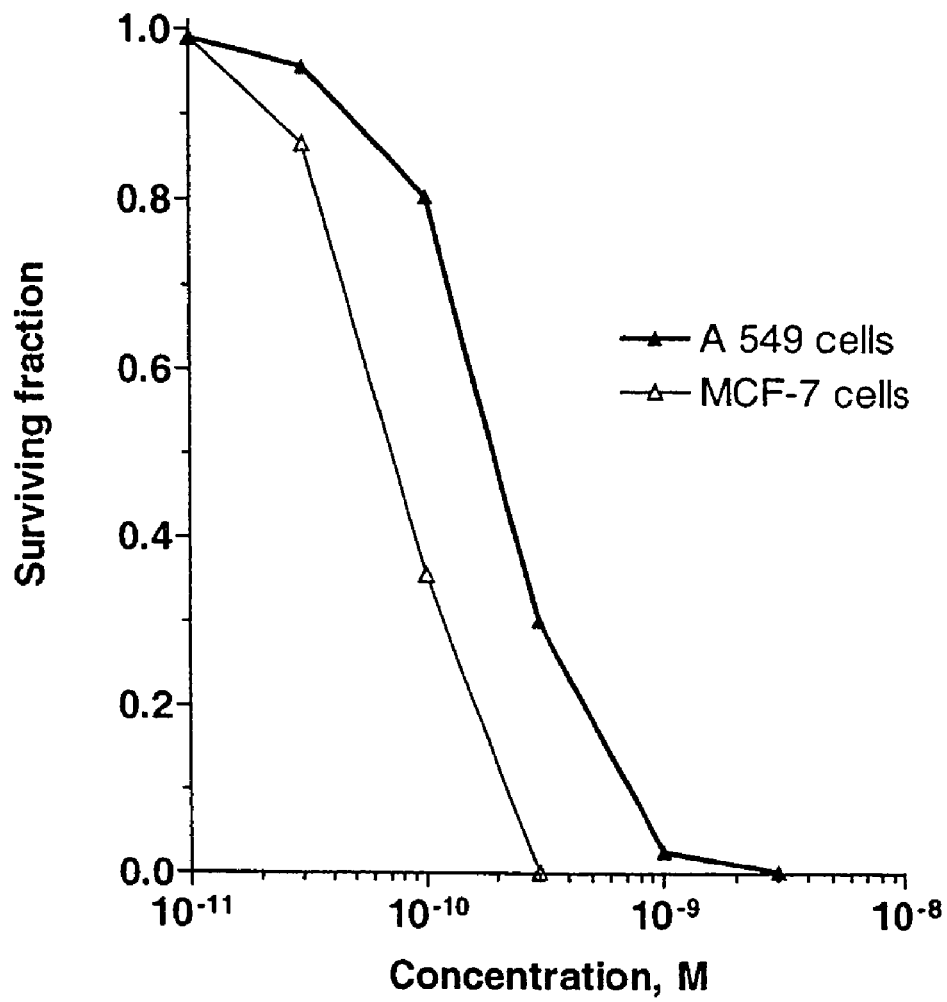
FIG. 11 shows the in vitro cytotoxicity of taxane 3' toward A549 and MCF-7 cells.

FIG. 11 shows the results of the cytotoxicity determination. Taxane 3' bearing a free hydroxy group at C-10 and a linking group at C-7 shows even greater potency towards the two tumor cell lines tested with $IC_{50}$ values of $1.8\times10^{-10}$ M and $6.3\times10^{-11}$ M towards A549 and MCF-7 cells, respectively. These results confirm that the C-10 position of a taxane does not need to be protected to maintain high potency.

Example 4

Conjugation to Antibodies

Conjugation of Thiol-containing Taxane to Antibodies via Disulfide Links

The conjugation of thiol-containing taxanes to antibodies, or fragments thereof, via disulfide links is performed in two steps. In the first step dithiopyridyl groups are introduced into antibodies or antibody fragments using succinimidyl pyridyldithiopentanoate (SPP) as described by Carlsson et al. The thiopyridyl groups are then displaced by reaction with the thiol-containing taxane to produce a conjugate.

Preparation of Antibody-SS-taxane Conjugates

Antibodies anti-B4, anti-EGF receptor and N901, or fragments thereof, are modified with SPDP or SPP as described in the literature. Between 1 to 10 dithiopyridyl groups are introduced on the average per antibody molecule.

A solution of the dithiopyridyl modified antibody at a concentration of 1 mg/ml in 0.1 M potassium phosphate buffer pH 6.5 containing 1 mM EDTA at 25° C. is treated with a thiol-containing taxane (1.25 molar equivalent/dithiopyridyl group). The release of thiopyridine from the modified antibody or fragment thereof is monitored spectrophotometrically at 343 nm and is found to be complete in about 20 hours. The antibody-taxane conjugate is purified and freed of unreacted drug and other low molecular weight material by gel filtration through a column of Sephadex G-25. The number of taxane molecules bound per antibody molecule is determined by measuring the ratio between the absorbances at 230 nm and 275 nm. An average of 1-10 taxane molecules per antibody molecule can be linked via disulfide bonds by this method.

Conjugation of Thiol-containing Taxane to Antibodies via a Noncleavable Thioether Link The conjugation of a thiol-containing taxane is performed in two steps. The antibody, or fragment thereof, is first reacted with succinimidyl maleimidomethylcyclohexane carboxylate (SMCC) to introduce maleimido groups. The modified antibody is then reacted with the thiol-containing taxane forming thioether links.

Preparation of Antibody-taxane Conjugates (Non-cleavable)

Antibodies, anti-B4, anti-EGF receptor and N901, or fragments thereof, are modified with SMCC as described in the literature.

The modified antibodies or antibody fragments are treated with thiol-containing taxane (1.25 molar equivalent/maleimido group). The mixtures are incubated overnight at 4° C. The antibody-taxane conjugates are purified as described above. Typically, an average of 1-10 taxane molecules per antibody molecule are linked.

Example 5

Specific Preparation of Antibody-taxane Conjugates

Murine monoclonal antibodies directed against the human EGF receptor (EGFR) were developed. The EGF receptor is known to be over-expressed in several human squamous cell cancers, such as, head and neck, lung and breast. Four different antibodies, KS-61 (IgG2a), KS-77 (IgG1), KS-78 (Ig2a), and KS-62 (IgG2a) were linked to taxanes via disulfide bonds. The murine monoclonal antibody TA1, directed against the neu oncogene over-expressed in human breast and ovarian cancers, was used for the preparation of TA1-taxane conjugates. The preparation of these particular conjugates is described below.

Preparation of Anti-EGFR Antibody KS-61-taxane Conjugate

The anti-EGFR antibody KS-61 was first modified with N-succinimidyl-4-[2-pyridyldithio]pentanoate (SPP) to introduce dithiopyridyl groups. The antibody (2.3 mg/mL) in 50 mM potassium phosphate buffer, pH 6.5, containing NaCl (50 mM) and EDTA (2 mM), was treated with SPP (11 molar equivalents in ethanol). The final ethanol concentration was 1.4% (v/v). After 90 minutes at ambient temperature, lysine (50 mM) was added to help in the removal of any noncovalently bound SPP. The reaction was allowed to proceed for two hours, and then purified by gel filtration through a Sephadex G25 column equilibrated in the above buffer. Antibody-containing fractions were pooled and the degree of modification was determined by treating a sample with dithiothreitol and measuring the change in absorbance at 343 nm (release of pyridine-2-thione with $\epsilon 343 = 8,080$ $M^{-1}$ $cm^{-1}$). Recovery of the antibody was about 90%, with 5.0 pyridyldithio groups linked per antibody molecule.

The modified antibody was diluted with 50 mM potassium phosphate buffer, pH 6.5, containing NaCl (50 mM) and EDTA (2 mM) to a final concentration of 1.28 mg/mL. Taxane-SH (1.7 eq. per dithiopyridyl group) in ethanol (10% v/v in final reaction mixture) was then added to the modified antibody solution. The reaction proceeded at ambient temperature under argon for 24 hours. The progress of the reaction was monitored spectrophotometrically at 343 nm for release of pyridine-2-thione, caused by disulfide exchange between the taxane-SH and the dithiopyridyl groups on the antibody. The increase in absorbance at 343 nm indicated that the taxane had linked to the antibody. The reaction mixture was then loaded on to a Sephadex G25 SF gel filtration column equilibrated with phosphate-buffered saline (PBS, pH 6.5) containing 20% propylene glycol. The major peak comprised monomeric KS-61-Taxane. The concentration of the conjugate was determined by measuring the absorbance at 280 nm. The conjugate was formulated with Tween 80 (0.05%) and human serum albumin (HSA, 1 mg/mL).

Preparation of Anti-EGFR Antibody KS-77-Taxane Conjugate

The anti-EGFR antibody KS-77 was modified with N-succinimidyl 4-[2-pyridyldithio]pentanoate (SPP) to introduce dithiopyridyl groups. The antibody (5.0 mg/mL) in 50 mM potassium phosphate buffer, pH 6.5, was treated with SPP (11 molar equivalents in ethanol). The final ethanol concentration was 2% (v/v). After 90 minutes at ambient temperature, lysine (50 mM) was added to help in the removal of any non-covalently bound SPP. The reaction mixture was allowed to incubate for two hours, and then purified by gel filtration through a Sephadex G25 column equilibrated in the above buffer. Antibody containing fractions were pooled and the degree of modification was determined by treating a sample with dithiothreitol and measuring the change in absorbance at 343 nm (release of 2-mercaptopyridine with $\epsilon 343 = 8,080\, M^{-1}\, cm^{-1}$). Recovery of the antibody was about 90%, with 4.24 pyridyldithio groups linked per antibody molecule.

The modified antibody was diluted with 50 mM potassium phosphate buffer, pH 6.5, containing NaCl (50 mM) and EDTA (2 mM) to a final concentration of 1.4 mg/mL. Taxane-SH (1.7 equivalents per dithiopyridyl group) in ethanol (10% v/v in final reaction mixture) was then added to the modified antibody solution. The reaction proceeded at ambient temperature under argon for 24 hours. An increase in absorbance at 343 nm was noted, indicating that pyridine-2-thione was being released, and the taxane had linked to the antibody. The reaction mixture was then loaded on to a Sephacryl S300HR gel filtration column equilibrated with phosphate-buffered saline (PBS, pH 6.5). The major peak comprised monomeric KS-77-Taxane. The concentration of antibody KS-77 was determined by measuring the absorbance at 280 nm. The conjugate was formulated with Tween 80 (0.06%) and HSA (1 mg/mL).

Preparation of Anti-EGFR Antibody KS-62-taxane Conjugate

The anti-EGF antibody-taxane conjugate (KS-62-Taxane) was prepared in a manner similar to that described for the preparation of the anti-EGFR antibody KS-77-taxane conjugate above. The modified antibody was diluted with 50 mM potassium phosphate buffer, pH 6.5, containing NaCl (50 mM) and EDTA (2 mM) to a final concentration of 2.5 mg/mL. The antibody was modified with SPP to introduce 5.25 pyridyldithio groups per antibody molecule Taxane-SH (1.7 eq.) in ethanol (10% v/v in final reaction mixture) was then added to the modified antibody solution. The reaction proceeded at ambient temperature under argon for 24 hours. The conjugate was purified by passage through a Sephacryl S300HR gel filtration column equilibrated with phosphate-buffered saline (PBS, pH 6.5). The major peak comprised monomeric KS-62-Taxane. The conjugate was formulated in PBS, containing Tween 80 (0.01%, w/v) and HSA (1 mg/mL).

Preparation of Anti-EGFR Antibody KS-78-taxane Conjugate

The anti-EGFR antibody-Taxane conjugate, KS-78-Taxane, was prepared in a manner similar to that described for the preparation of the anti-EGFR antibody KS-77-taxane conjugate above. The modified antibody was diluted with 50 mM potassium phosphate buffer, pH 6.5, containing NaCl (50 mM) and EDTA (2 mM) to a final concentration of 1.6 mg/mL. The antibody was modified with SPP to introduce 4.0 pyridyldithio groups per antibody molecule. Taxane-SH (1.7 eq.) in ethanol (15% v/v in final reaction mixture) was then added to the modified antibody solution. The reaction proceeded at ambient temperature under argon for 24 hours. The solution was then split into two batches, Batch A and Batch B, which were treated separately. Batch A was dialyzed against PBS, pH 6.5 containing 2 mM CHAPS (3-[(cholamidopropyl) dimethylammonio]-1-propanesulfonate) and 20% (v/v) propylene glycol. The pH of the final solution was 6.0. Batch B was dialyzed into PBS, pH 6.5 containing 20% (v/v) propylene glycol. After dialyses, HSA (1 mg/mL) was added to both batches. Batch B was further treated with Tween 80 (0.05%, w/v).

Preparation of TA1-taxane Conjugate

The murine monoclonal antibody TA1, which binds to the neu oncogene expressed on breast and ovarian tumors, was used in the preparation of a taxane conjugate. TA1 (3.2 mg/mL) in 50 mM potassium phosphate buffer, pH 6.5, containing NaCl (50 mM) and EDTA (2 mM) was treated with SPP (8.0 molar equivalents in ethanol). The final ethanol concentration was 5% (v/v). After 90 minutes at ambient temperature, lysine (50 mM) was added to help in the removal of any non-covalently bound SPP. The reaction mixture was incubated for 2 hours, and then gel filtered through a Sephadex G25 column equilibrated in the above buffer. Antibody-containing fractions were pooled and the degree of modification was determined by treating a sample with dithiothreitol and measuring the change in absorbance at 343 nm (release of pyridine-2-thione with $\epsilon 343 = 8,080\, M^{-1}\, cm^{-1}$). Recovery of the antibody was about 90%, with 4.9 pyridyldithio groups linked per antibody molecule.

The modified antibody was diluted with 50 mM potassium phosphate buffer, pH 6.5, containing NaCl (50 mM) and EDTA (2 mM) to a final concentration of 1.0 mg/mL. Taxane-SH (1.7 eq. per pyridyldithio group incorporated) in ethanol (10% v/v in final reaction mixture) was then added to the modified antibody solution. The reaction proceeded at ambient temperature under argon for 24 hours. The release of pyridine-2-thione (monitored at 343 nm), indicated that the disulfide exchange between the Taxane-SH and the pyridyldithio substituent on the antibody was complete. A portion of the reaction mixture (4.0 mg) was then loaded on a Sephacryl S300HR gel filtration column equilibrated with phosphate-buffered saline (PBS, pH 6.5). The major peak comprised monomeric TA1-Taxane. The remaining conjugate was diluted to 0.5 mg/mL, and dialyzed into 50 mM potassium phosphate buffer, pH 6.5, containing NaCl (50 mM), EDTA (2 mM) and 20% propylene glycol. The concentration of antibody TA1 was determined in both species by measuring the absorbance at 280 nm. The conjugates were formulated in PBS containing Tween 80 (0.01%) and HSA (1 mg/mL).

Example 6

Other Methods of Linking Taxanes

Acid Labile Linkers

Taxanes can be esterified with N-protected amino acids, such as N-tboc-L-alanine in the presence of dicyclohexylcarbodiimide and dimethylaminopyridine (DMAP) by standard methods described in the chemical literature. Cleavage of the t-boc protecting group with trifluoroacetic acid will give a taxane ester containing a terminal amino group. This amino group containing taxane can be linked to antibodies, or fragments thereof, and other cell binding agents via an acid labile linker as previously described (Blättler et al, Biochemistry, 24: 1517-1524 (1985), U.S. Pat. Nos. 4,542,225, 4,569,789 and 4,764,368).

Photolabile Linker

The amino group-containing taxane derivative described above can be linked to cell binding agents via a photolabile linker as previously described. (Senter et al, Photochemistry and Photobiology, 42: 231-237 (1985), U.S. Pat. No. 4,625,014).

Peptidase Labile Linker

The amino group-containing taxane described above can also be linked to cell binding agents via peptide spacer linkers. It has been previously shown that short peptide spacers between drugs and macromolecular protein carriers are stable in serum but are readily hydrolyzed by intracellular lysosomal peptidases (Trouet et al, Proc. Nat'l. Acad. Sci., 79: 626-629 (1982)). The amino group containing taxane can be condensed with peptides such as Ala-Leu, Leu-Ala-Leu or a dimer of Ala-Leu using condensing agents such as 1-[3-(dimethylamino)propyl]-3-ethyl carbodiimide-HCl to give a peptide derivative of the taxane which can then be linked to cell binding agents.

Esterase Labile Linker

Taxanes can be esterified by reaction of the hydroxyl group with succinic anhydride and then linked to a cell binding agent to produce a conjugate that can be cleaved by intracellular esterases to liberate free drug. (For examples see: Aboud-Pirak et al, Biochem. Pharmacol., 38: 641-648 (1989), Laguzza et al, J. Med. Chem., 32: 549-555 (1989)).

Example 7

In Vivo Anti-tumor Activity

The anti-tumor effect of anti-EGF receptor antibody-taxane conjugate on human squamous cancer (A431) xenografts in SCID mice was established as follows. The anti-tumor effect of two different anti-human epidermal growth factor receptor-taxane conjugates (anti-EGFR-taxane conjugates), KS-61-Taxane and KS-77-Taxane was evaluated in a human tumor xenograft model in SCID mice.

Five week old female SCID mice (25 animals) were inoculated subcutaneously in the right flank with A-431 human squamous cancer cells ($1.5 \times 10^6$ cells/mouse) in 0.1 mL of serum-free medium. The tumors were grown for 11 days to an average size of 100.0 mm$^3$ (range of 54-145 mm$^3$). The animals were then randomly divided into four groups (3 to 5 animals per group) according to their tumor size. The first group received KS-61-Taxane conjugate (10 mg/kg, qd×5) administered intravenously. The second group received the KS-77-Taxane conjugate (10 mg/kg, qd×5) administered intravenously. The third group received free (non-conjugated) taxane (0.24 mg/kg, qd×5, intravenously) at the same dose as that present in the conjugate. The fourth group, a control group of animals, received PBS using the same treatment schedule as groups 1-3.

Figure 12:
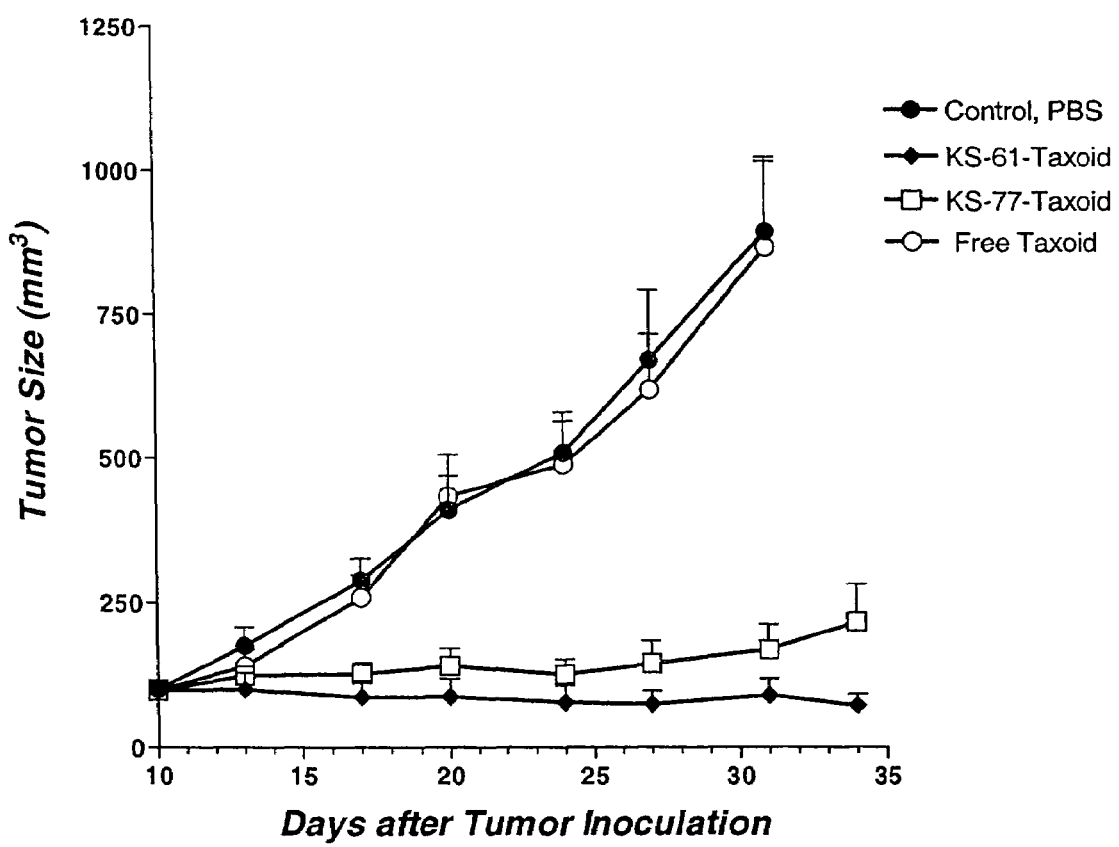
FIG. 12 shows the anti-tumor effect of anti-EGF receptor antibody-taxane conjugate on human squamous cancer (A431) xenografts in SCID mice.
Figure 13:
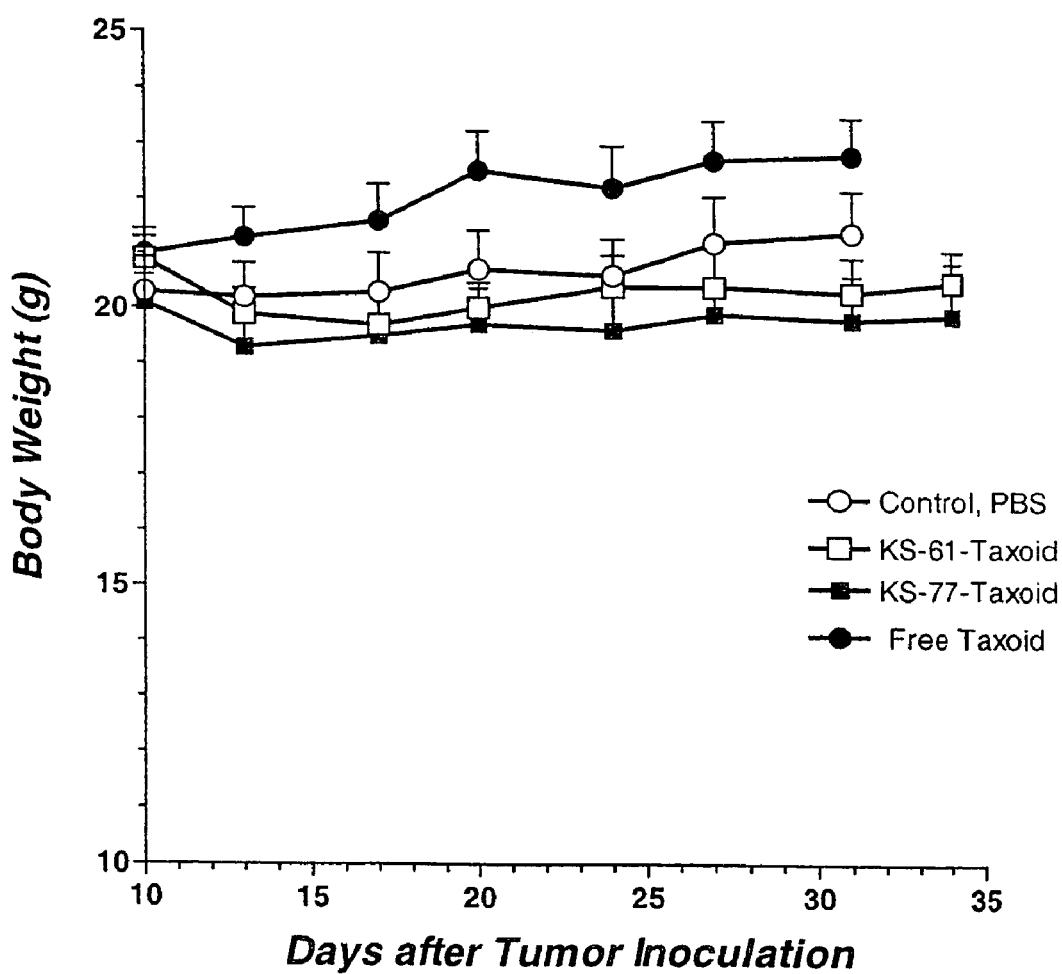
FIG. 13 shows the body weight change of the SCID mice used in the experiment described in Example 8.

The sizes of the tumors were measured twice weekly and the tumor volumes were calculated with the formula: ½(length×width×height). The weight of the animals was also measured twice per week. The results are shown in FIGS. 12 and 13. The tumors in the control group of mice grew to a size of nearly 1000 mm$^3$ in 31 days. Treatment with free taxane showed no therapeutic effect, and the tumors in this group grew at essentially the same rate as in the control group of animals that received PBS.

In contrast, both of the anti-EGFR-taxane conjugates showed remarkable anti-tumor activity resulting in complete inhibition of tumor growth in all the treated animals for the duration of the experiment—34 days for the KS-61-Taxane conjugate and 27 days for the KS-77-Taxane conjugate. The data also show that targeted delivery of the taxane using a tumor-specific antibody is essential for the anti-tumor activity, since an equivalent dose of unconjugated taxane showed no anti-tumor effect in this model. Importantly, the doses of antibody-taxane conjugate used were non-toxic to the animals as demonstrated by the absence of any weight loss (see FIG. 13).

Example 8

In Vitro Cytotoxicity of Antibody-taxane Conjugates

The cytotoxicity of anti-EGFR-taxane conjugate, KS-78-Taxane, was measured in a clonogenic assay using the EGF-receptor-positive human A431 cell line (ATCC CRL 1555). N901-taxane conjugate, a similar conjugate made with the mouse monoclonal antibody N901 against human CD56 was tested as a specificity control, since A431 cells do not express its target antigen, CD56. The cytotoxicity of TA1-Taxane conjugate, a conjugate made with the mouse monoclonal antibody TA1 against human Neu antigen, was measured on the antigen-positive human cell line SK-BR-3 (ATCC HTB 30) and the antigen-negative A431 cell line. Cells were plated at different densities in 6-well tissue-culture plates in DMEM medium supplemented with 10% fetal calf serum. Immunoconjugates at varying concentrations were added and the cells were maintained in a humidified atmosphere at 37° C. and 6% $CO_2$ until colonies of approximately 20 cells or more were formed (6 to 10 days). Control plates contained no immunoconjugate. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

Figure 14:
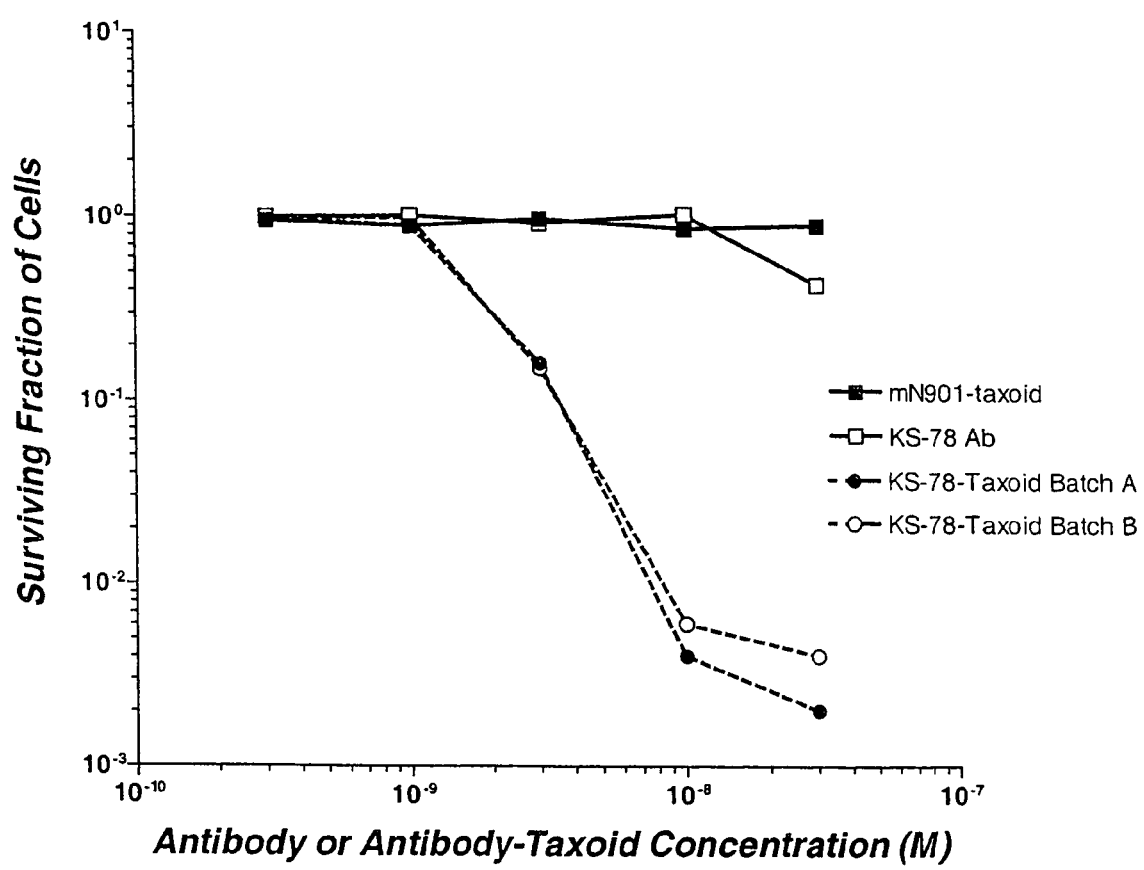
FIG. 14 shows the results of a cytotoxicity determination for the anti-EGF receptor-taxane conjugate on the target antigen-positive cell line A431 and for the N901-taxane conjugate for which the A431 cell line does not express the target antigen.

FIG. 14 shows the results of the cytotoxicity determination for the two Batches of KS-78-Taxane conjugate on the target antigen-positive cell line A431. Conjugates from both batches show similar toxicity to the target cells; treatment for 6 days at concentrations of $10^{-8}$ M achieved surviving fractions of less than $10^{-2}$ (less than 1% of cells survive). A control conjugate, N901-Taxane, for which there are no antigens present on the surface of A431 cells, shows no toxicity to the cells at concentrations of up to $3 \times 10^{-8}$ M. Unconjugated KS-78 antibody also shows very little cytotoxic effect. These results demonstrate the target antigen-specific cytotoxicity of the KS-78-taxane conjugate.

Figure 15:
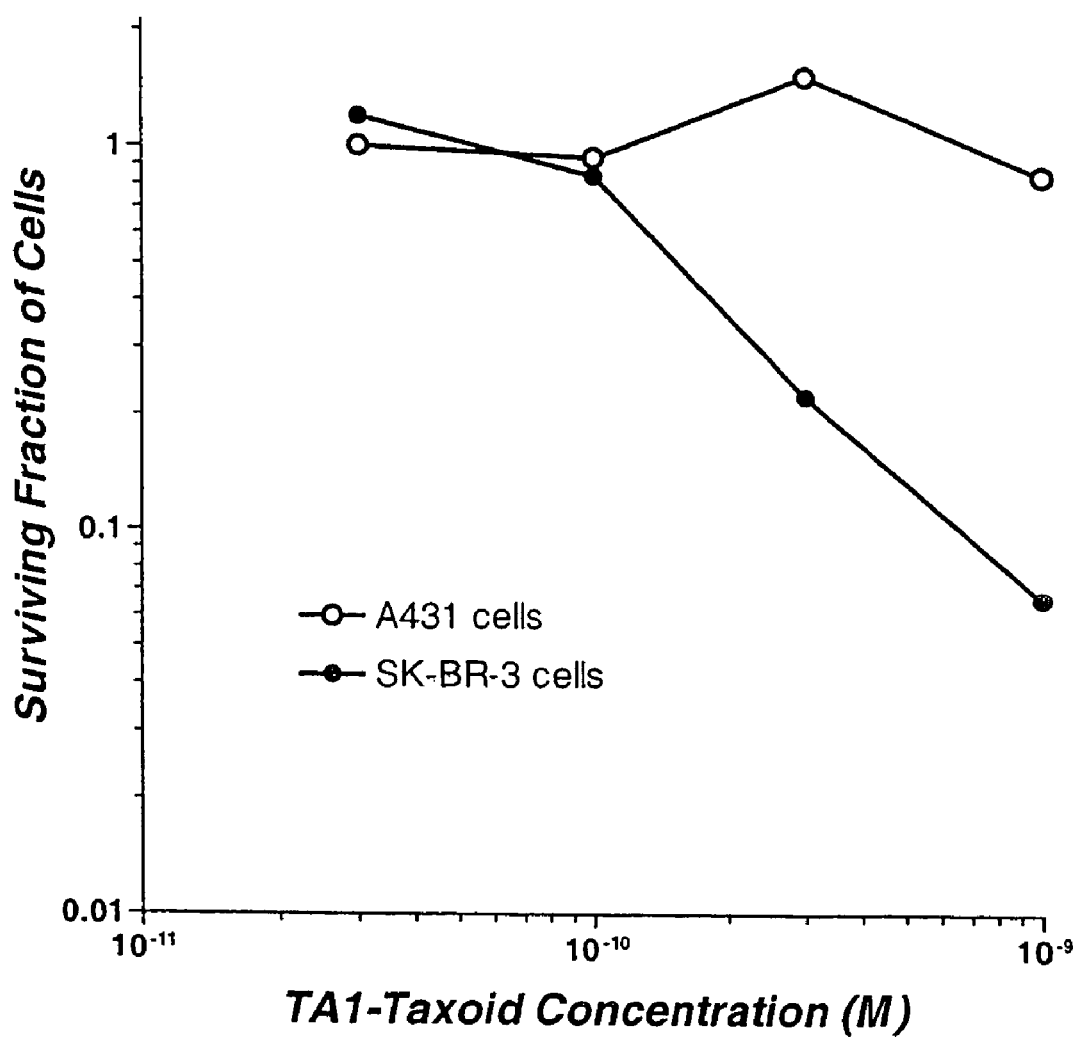
FIG. 15 shows the cytotoxic potency and selectivity of the TA1-taxane conjugate in the target antigen-positive cell line SK-BR-3 and the non-target antigen-negative cell line A431.

The cytotoxic potency and selectivity of the TA1-taxane conjugate was assayed with the target antigen-positive cell line SK-BR-3 and the target antigen-negative cell line A431. The results are shown in FIG. 15. At a conjugate concentration of $10^{-9}$ M, more than 90% of the target SK-BR-3 cells were killed (surviving fraction of less than 0.1), while no These results demonstrate the selective killing of antigen-positive cells and that the cytotoxic effect of the conjugate is dependent on the specific binding through its antibody component.

Examples 9 and 10

General Methods:

Chemicals were obtained from Aldrich Chemical Co. or other commercial sources and were used without further purification, unless otherwise noted. All anhydrous reactions were performed in oven-dried glassware under argon. Tetrahydrofuran (THF) was distilled over sodium/benzophenone. All reactions were monitored by E. Merck analytical thin layer chromatography (TLC) plates (silica gel 60 GF, aluminum back) and analyzed with 254 nm UV light and/or vanillin/sulfuric acid spray and/or phosphomolybdic acid/ethanol spray. Silica gel for column chromatography was purchased from E. Merck (230-400 mesh). Preparative thin layer chromatography (PTLC) plates (silica gel 60 GF) were purchased from Analtech. $^1$H and $^{13}$C NMR spectra were obtained in $CDCl_3$ on a Bruker 400 MHz spectrometer and were assigned by comparison of chemical shifts and coupling constants with those of related compounds. Chemical shifts are reported as δ-values, and coupling constants are reported in Hertz. Mass spectra were obtained on an Agilent Esquire 3000 Electrospray Mass Spectrometer. The phrase "worked-up in the usual way" refers to diluting the reaction mixture with an excess amount of an organic solvent, washing with water and brine, drying over sodium sulfate and evaporating the solvent in vacuo unless otherwise noted. The beta-lactams 4, 19 and 38 the baccatin III derivative 7 were prepared following the procedures that are reported in the literature (Brieva, R. Crich, J. Z.; Sih, C. J. J. Org. Chem., 58: 1068-1075 (1993); Holton, R. A.; Zhang, Z.; Clarke, P. A.; Nadizadeh, H.; Procter, J. D. Tetrahedron Lett. 39: 2883-2886 (1998); Chen, S-H.; Vittorio, F.; Wei, J-M.; Long, B.; Fairchild, C.; Mamber, S. W.; Kadow, J. F.; Vyas, D.; Doyle, T. W. Bioorganic Med. Chem. Lett., 4(3): 479-482 (1994). NMR data of these compounds were identical to those in the literature.

Example 9

Synthesis of New Taxoids 12-15, 31-35 and 50-54 (FIGS. 5 and 16) of the Present Invention is Described Below General procedure for the coupling of the baccatin III derivative 7 with the β-lactams 6a-d, 21-25 and 40-44.

Synthesis of the silyl protected taxoids 8-11, 26-30 and 45-49. To a stirred solution of the baccatin derivative 7 (0.04 mmol) in THF (2 mL) was added NaH (2 mmol). The reaction mixture was stirred for 15 min., a β-lactam, such as 6a-d, 21-25 or 40-44; 0.08 mmol) was introduced, and the reaction mixture was further stirred for 4-6 h. The reaction was diluted with EtOAc, quenched with acetic acid, and worked-up in the usual way. Finally, the crude product was applied on a PTLC plate (30% EtOAc/Hexane) and the desired product was isolated.

General Procedure for Removal of the Silyl Protecting Groups; Synthesis of the Taxoids 12-15, 31-35 and 50-54

To a stirred solution of every 10 mg of a protected taxoid 8-11, 26-30 or 45-49) in THF (0.5 mL) was added 0.15 mL of pyridine at 0° C. Then over 5 min, 0.15 mL of HF-pyridine was introduced to the stirred solution. The reaction mixture was allowed to come to room temperature and further stirred for 24 h. The reaction mixture was then diluted with EtOAc, washed with saturated aqueous $NaHCO_3$ solution and worked-up in the usual way. Finally the crude product was applied to a PTLC plate (60% EtOAc/Hexane) and the desired product was isolated.

Synthesis of Representative Disulfide-containing Taxoids (FIGS. 6, 17) of the Present Invention Removal of the C-10 Acetate Group. Synthesis of 16.

To a stirred solution of the taxoid 10 (~70 mg) in ethanol (1.5 mL) was added at room temperature hydrazine monohydrate (0.6 mL). The reaction mixture was stirred at room temperature for 1 h, then diluted with ethyl acetate, washed with aqueous saturated ammonium chloride solution and worked-up in the usual way. The crude product was applied to a PTLC plate (10% EtOAc/$CH_2Cl_2$) and the desired product was isolated.

Esterification of the C-10 Hydroxyl Group of Taxoids. Synthesis of 17 and 36

To a stirred solution of a carboxylic acid in dichloromethane (2 mL for every 30 mg of acid) was added EDC (1-[3-(dimethylamino)propyl-3-ethylcarbodiimide hydrochloride) (1 equiv.) at room temperature and the reaction mixture was stirred for 15 min. DMAP (4-(dimethylamino)pyridine) (catalytic amount) was then added and the reaction mixture was stirred for another 5 min. The C-10 deacetyl taxoid 16 (1/15 equiv.) was then introduced at room temperature and the reaction mixture was further stirred for 4 h. The reaction mixture was diluted with ethyl acetate, washed with water, saturated aqueous $NaHCO_3$ solution and worked-up in the usual way. Finally the crude product was applied to a PTLC plate (10% EtOAc/Hexane) and the desired product was isolated.

Synthesis of Disulfide-containing Taxoids 18 and 37

To a stirred solution of every 10 mg of a protected taxoid 17 or 36 in THF (0.5 mL) was added 0.15 mL of pyridine at 0° C. Then over 5 min, 0.15 mL of HF-pyridine was introduced to the stirred solution. The reaction mixture was allowed to come to room temperature and further stirred for 24 h. The reaction mixture was then diluted with EtOAc, washed with saturated aqueous $NaHCO_3$ solution and worked-up in the usual way. Finally the crude product was applied to a PTLC plate (60% EtOAc/Hexane) and the desired products 18 and 37 were obtained.

Compound 6a.
$^1$H NMR ($CDCl_3$) δ 7.03 (m, 1H), 5.26 (dt, 1H), 4.96 (t, 1H), 4.94 (t, 1H), 1.82 (s, 3H), 1.76 (s, 3H), 1.63 (m, 8H), 1.06 (m, 21H).

Compound 6b.
$^1$H NMR ($CDCl_3$) δ 7.31 (m, 1H), 5.26 (dt, 1H), 4.96 (t, 1H), 4.92 (t, 1H), 2.6 (m, 6H), 1.82 (s, 3H), 1.76 (s, 3H), 1.06 (m, 21H).

Compound 6c.
$^1$H NMR ($CDCl_3$) δ 7.1 (m, 1H), 6.74 (dd, 1H), 5.24 (dt, 1H), 5.02 (d, J=6 Hz, 1H), 4.85 (m, 1H), 1.91 (dd, 3H), 1.81 (s, 3H), 1.77 (s, 3H), 1.06 (m, 21H); $^{13}$C NMR ($CDCl_3$) δ 166.93, 162.99, 145.98, 140.20, 124.01, 117.68, 76.89, 55.77, 26.05, 18.33, 18.28, 17.66, 17.50, 17.46; LRMS m/z calculated for $C_{20}H_{35}NO_3SiNa$ (M+Na)$^+$ 388.23, found 388.

Compound 6d.
$^1$H NMR ($CDCl_3$) δ 6.55 (m, 1H), 5.24 (dt, 1H), 4.98 (d, J=5.6 Hz, 1H), 4.85 (m, 1H), 2.17 (s, 3H), 1.94 (s, 3H), 1.81 (s, 3H), 1.77 (s, 3H) 1.06 (m, 21 H); $^{13}$C NMR ($CDCl_3$) δ

166.65, 163.29, 159.81, 139.58, 126.15, 118.27, 117.45, 76.59, 55.71, 27.92, 26.07, 21.25, 18.34, 17.50, 17.46; LRMS m/z calculated for $C_{21}H_{37}NO_3SiNa$ $(M+Na)^+$ 402.24, found 402.1.

Compound 8.

$^1$H NMR (CDCl$_3$) δ 7.32 (d, J=3.2 Hz, 1H), 7.07 (d, J=3.2 Hz, 1H), 7.04 (d, J=3.2 Hz, 1H), 6.95 (d, J=9.2 Hz, 1H), 6.58 (bs, 1H), 6.43 (s, 1H), 6.12 (d, J=9.2 Hz, 1H), 6.03 (t, 1H), 5.67 (d, J=6.4 Hz, 1H), 5.38 (d, J=8.8 Hz, 1H), 5.09 (t, 1H), 4.89 (d, J=8.4 Hz, 1H), 4.47 (s, 1H), 4.42 (m, 2H), 4.28 (d, J=8 Hz, 1 H), 3.97 (s, 3H), 3.79 (s, 3H), 3.74 (m, 1H), 2.48 (m, 1H), 2.36 (d, 1H), 2.20 (s, 3H), 2.17 (s, 6H), 2.08 (m, 2H), 1.98 (s, 3H), 1.89 (m, 2H), 1.72 (s, 9H), 1.60 (m, 5H), 1.22 (s, 3H), 1.21 (s, 3H), 1.11 (s, 21H), 0.91 (t, 9H), 0.56 (m, 6H).

Compound 9.

$^1$H NMR (CDCl$_3$) δ 7.32 (d, J=3.2 Hz, 1H), 7.07 (d, J=2.8 Hz, 1H), 7.04 (d, J=3.2 Hz, 1H), 6.95 (d, J=8.8 Hz, 1H), 6.47 (bs, 1H), 6.43 (s, 1H), 6.07 (d, J=9.2 Hz, 1H), 6.4 (t, 1H), 5.68 (d, J=6.8 Hz, 1H), 5.38 (d, J=9.2 Hz, 1H), 5.09 (t, 1H), 4.89 (d, J=8.4 Hz, 1H), 4.47 (s, 1H), 4.42 (m, 2H), 4.28 (d, J=8.4 Hz, 1 H), 3.96 (s, 3H), 3.79 (s, 3H), 3.74 (d, J=6.4 Hz, 1H), 2.45 (m, 5H), 2.35 (d, J=9.2 Hz, 1H), 2.17 (s, 3H), 2.15 (s, 3H), 1.98 (s, 3H), 1.89 (m, 4H), 1.72 (s, 9H), 1.24 (s, 3H), 1.22 (s, 3H), 1.11 (s, 21H), 0.90 (t, 9H), 0.55 (m, 6H).

Compound 10.

$^1$H NMR (CDCl$_3$) δ 7.29 (d, J=3.2 Hz, 1H), 7.05 (dd, 1H), 6.94 (d, J=9.2 Hz, 1H), 6.71 (m, 1H), 6.43 (s, 1H), 6.05 (t, 1H), 5.74 (m, 2H), 5.67 (d, J=6.8 Hz, 1H), 5.37 (d, J=8.8 Hz, 1H), 5.10 (t, 1H), 4.88 (d, J=9.6 Hz, 1H), 4.25-4.47 (m, 5H), 4.10 (m, 1H), 3.96 (s, 3H), 3.79 (s, 3H), 3.73 (m, 1H), 2.48 (m, 1H), 2.36 (bs, 1H), 2.33 (bs, 1H), 2.17 (s, 3H), 2.15 (s, 3H), 1.97 (s, 3H), 1.79 (d, J=6.8 Hz, 3H), 1.71 (s, 9H), 1.21 (m, 7H), 1.10 (s, 21H), 0.90 (t, 12H), 0.55 (m, 6H); $^{13}$C NMR (CDCl$_3$) δ 201.97, 171.67, 169.68, 169.27, 166.77, 164.65, 153.40, 152.83, 140.51, 139.82, 136.79, 133.72, 124.99, 121.57, 120.26, 119.93, 115.91, 113.54, 84.35, 81.00, 77.22, 76.44, 76.24, 75.27, 74.72, 72.19, 71.91, 58.62, 56.78, 55.81, 50.16, 46.54, 42.86, 37.30, 36.47, 26.55, 25.59, 22.54, 21.13, 20.82, 18.47, 18.01, 17.93, 17.63, 14.37, 12.53, 9.98, 6.68, 5.27; LRMS m/z calculated for $C_{59}H_{91}NO_{16}Si_2Na$ $(M+Na)^+$ 1148.58, found 1148.5.

Compound 11.

$^1$H NMR (CDCl$_3$) δ 7.29 (d, J=3.2 Hz, 1H), 7.05 (dd, 1H), 6.94 (d, J=9.2 Hz, 1H), 6.44 (s, 1H), 6.04 (t, 1H), 5.65 (m, 2H), 5.49 (s, 1H), 5.38 (d, J=9.2 Hz, 1H), 5.13 (t, 1H), 4.89 (d, J=8.4 Hz, 1H), 4.45 (s, 1H), 4.40 (m, 2H), 4.27 (d, J=8 Hz, 1H), 3.98 (s, 3H), 3.79 (s, 3H), 3.74 (m, 1H), 3.14 (s, 1H), 2.48 (m, 3H), 2.17 (s, 3H), 2.15 (s, 3H), 2.04 (s, 3H), 1.98 (s, 3H), 1.71 (s, 9H), 1.21 (s, 3H), 1.10 (s, 3H), 1.10 (s, 21H), 0.90 (t, 9H), 0.55 (m, 6H); $^{13}$C NMR (CDCl$_3$) δ 203.94, 202.03, 171.80 169.66, 169.28, 166.86, 165.62, 153.42, 152.75, 151.23, 150.56, 140.71, 136.39, 136.17, 133.64, 132.41, 121.83, 120.35, 119.96, 118.46, 115.84, 113.58, 113.49, 106.05, 84.37, 81.03, 77.18, 76.45, 76.40, 75.32, 74.90, 72.20, 72.06, 60.88, 58.64, 56.74, 55.82, 49.78, 46.55, 45.82, 42.84, 37.32, 36.51, 26.96, 26.47, 25.59, 22.55, 21.12, 20.83, 19.68, 18.02, 17.85, 14.40, 12.54, 9.98, 6.69, 5.28; LRMS m/z calculated for $C_{60}H_{93}NO_{16}Si_2Na$ $(M+Na)^+$ 1162.59, found 1162.3.

Compound 12.

$^1$H NMR (CDCl$_3$) δ 7.32 (d, J=3.2 Hz, 1H), 7.07 (dd, 1H), 6.94 (d, J=9.2 Hz, 1H), 6.58 (s, 1H), 6.29 (s, 1H), 6.18 (t, 1H), 5.89 (d, J=8.4 Hz, 1H), 5.66 (d, J=6.8 Hz, 1H), 5.38 (d, J=8.8 Hz, 1H), 5.10 (t, 1H), 4.93 (d, 1H), 4.40 (d, J=8.4 Hz, 1H), 4.35 (m, 1H), 4.27 (d, J=8.4 Hz, 1H), 4.24 (m, 1H), 3.94 (s, 3H), 3.80 (s, 3H), 3.74 (d, J=6.8 Hz, 1H), 3.61 (d, J=6.4 Hz, 1H), 3.00 (s, 1H), 2.58-2.30 (m, 4H), 2.23 (s, 3H), 2.20 (s, 3H), 2.13 (m, 4H), 1.86 (s, 3H), 1.75 (s, 3H), 1.72 (s, 3H), 1.69 (s, 3H), 1.63 (s, 6H), 1.60 (m, 2H), 1.29 (s, 3H), 1.15 (s, 3H); LRMS m/z calculated for $C_{47}H_{61}NO_{16}Na$ $(M+Na)^+$ 918.39, found 918.3.

Compound 13.

$^1$H NMR (CDCl$_3$) δ 7.33 (d, J=3.2 Hz, 1H), 7.06 (dd, 1H), 6.94 (d, J=9.2 Hz, 1H), 6.50 (s, 1H), 6.29 (s, 1H), 6.19 (t, 1H), 5.86 (d, J=8.4 Hz, 1H), 5.66 (d, J=6.8 Hz, 1H), 5.38 (d, J=9.2 Hz, 1H), 5.08 (t, 1H), 4.93 (d, J=8.4 Hz, 1 H), 4.39 (m, 2H), 4.29 (d, J=8.4 Hz, 1H), 4.25 (m, 1H), 3.93 (s, 3H), 3.80 (s, 3H), 3.74 (d, J=6.4 Hz, 1H), 3.64 (d, J=6.4 Hz, 1H), 3.00 (s, 1H), 2.41-2.56 (m, 7H), 2.32 (m, 1H), 2.23 (s, 3H), 2.22 (s, 3H), 1.98 (m, 2H), 1.86 (s, 3H), 1.75 (m, 11H), 1.29 (s, 3H), 1.15 (s, 3H); $^{13}$C NMR (CDCl$_3$) δ 203.90, 172.88, 171.24, 170.21, 166.63, 164.86, 153.39, 153.03, 142.25, 139.02, 138.93, 138.60, 133.33, 120.24, 120.14, 119.90, 115.93, 113.55, 84.51, 81.04, 77.74, 76.47, 76.10, 75.77, 73.56, 72.23, 72.17, 58.83, 56.69, 55.86, 49.95, 45.56, 42.88, 36.56, 35.74, 33.14, 31.48, 26.90, 25.67, 23.25, 22.42, 21.72, 20.86, 18.55, 14.97, 9.53; LRMS m/z calculated for $C_{46}H_{59}NO_{16}Na$ $(M+Na)^+$ 904.37, found 904.4.

Compound 14.

$^1$H NMR (CDCl$_3$) δ 7.33 (d, J=3.2 Hz, 1H), 7.07 (dd, 1H), 6.95 (d, J=9.2 Hz, 1H), 6.78 (m, 1H), 6.29 (s, 1H), 6.19 (t, 1H), 5.74 (d, J=15.2 Hz, 1H), 5.67 (d, J=6.4 Hz, 1H), 5.62 (d, J=8.4 Hz, 1H), 5.39 (d, J=8.8 Hz, 1H), 5.09 (t, 1 H), 4.93 (d, 1H), 4.40 (d, J=8.4 Hz, 1H), 4.37 (m, 1H), 4.30 (d, J=8.4 Hz, 1H), 4.24 (m, 1H), 3.94 (s, 3H), 3.80 (s, 3H), 3.74 (d, J=6.4 Hz, 1H), 3.59 (d, J=6 Hz, 1 H), 2.97 (s, 1H), 2.31-2.56 (m, 5H), 2.23 (s, 3H), 2.21 (s, 3H), 1.84 (s, 3H), 1.82 (m, 3H), 1.75 (s, 3H), 1.72 (s, 3H), 1.69 (s, 3H), 1.60 (s, 3H), 1.29 (s, 3H), 1.15 (s, 3H); LRMS m/z calculated for $C_{44}H_{57}NO_{16}Na$ $(M+Na)^+$ 878.36, found 878.3.

Compound 15.

$^1$H NMR (CDCl$_3$) δ 7.33 (d, J=3.2 Hz, 1H), 7.07 (dd, 1H), 6.94 (d, J=8.8 Hz, 1H), 6.29 (s, 1H), 6.18 (t, 1H), 5.67 (d, J=6.8 Hz, 1H), 5.52 (m, 2H), 5.40 (d, J=8.8 Hz, 1H), 5.05 (t, 1H), 4.93 (d, 1H), 4.40 (m, 2H), 4.29 (d, J=8.4 Hz, 1H), 4.23 (m, 1H), 3.94 (s, 3H), 3.80 (s, 3H), 3.75 (d, J=6.4 Hz, 1H), 3.57 (d, J=6.4 Hz, 1H), 2.97 (s, 1H), 2.33-2.58 (m, 4H), 2.23 (s, 3H), 2.21 (s, 3H), 2.07 (s, 3H), 1.87 (s, 3H), 1.81 (s, 3H), 1.75 (s, 3H), 1.72 (s, 3H), 1.68 (s, 3H), 1.40 (t, 1H), 1.29 (s, 3H), 1.15 (s, 3H); $^{13}$C NMR (CDCl$_3$) δ 203.95, 196.43, 173.15, 171.25, 170.08, 166.71, 166.28, 153.41, 152.97, 152.13, 151.25, 142.50, 138.44, 136.19, 133.19, 120.45, 120.19, 119.96, 117.80, 115.85, 113.53, 106.08, 94.84, 91.01, 84.52, 81.01, 77.71, 76.45, 76.24, 75.79, 73.61, 72.50, 72.18, 58.82, 56.64, 55.86, 49.85, 45.84, 45.55, 42.86, 36.63, 35.71, 27.12, 26.80, 25.60, 22.41, 21.75, 20.85, 19.73, 18.48, 14.95, 9.52; LRMS m/z calculated for $C_{45}H_{59}NO_{16}Na$ $(M+Na)^+$ 892.37, found 892.3.

Compound 16.

$^1$H NMR (CDCl$_3$) δ 7.30 (t, 1H), 7.06 (dm, 1H), 6.95 (d, J=9.2 Hz, 1H), 6.72 (m, 1H), 6.12 (q, 1H), 5.75 (m, 2H), 5.64 (d, J=6.8 Hz, 1H), 5.62 (d, J=8.4 Hz, 1H), 5.37 (m, 1H), 5.10 (m, 2H), 4.89 (d, 1H), 4.26-4.47 (m, 5H), 3.97 (s, 3 H), 3.80 (s, 3H), 3.79 (d, 1H), 3.10 (d, J=15.6 Hz, 1H), 2.31-2.44 (m, 3H), 2.18 (s, 3H), 2.09 (t, 1H), 1.91 (s, 3H), 1.69-1.82 (m, 12H), 1.57 (m, 1H), 1.25 (s, 3H), 1.12 (m, 25H), 0.9 (m, 12H), 0.5 (m, 6H).

Compound 17.

¹H NMR (CDCl₃) δ 7.30 (t, 1H), 7.06 (dm, 1H), 6.95 (d, J=9.2 Hz, 1H), 6.72 (m, 1H), 6.47 (s, 1H), 6.05 (t, 1H), 5.72 (m, 2H), 5.38 (m, 1H), 5.10 (m, 1H), 4.89 (d, 1H), 4.40-4.48 (m, 3H), 4.28 (d, J=8 Hz, 1H), 3.98 (s, 3H), 3.80 (s, 3H), 3.74 (d, J=6.4 Hz, 1H), 3.13 (d, J=12 Hz, 1H), 2.82-3.15 (m, 4H), 2.43 (s, 3H), 2.35-2.51 (m, 3H), 2.18 (d, 3H), 2.09 (m, 1H), 1.99 (s, 3H), 1.79-1.93 (m, 2H), 1.71 (m, 9H), 1.56 (s, 3H), 1.22 (s, 6H), 1.11 (s, 21H), 0.9 (m, 12H), 0.5 (m, 6H).

Compound 18.

¹H NMR (CDCl₃) δ 7.32 (t, 1H), 7.06 (dm, 1H), 6.95 (d, J=8.8 Hz, 1H), 6.72 (m, 1H), 6.33 (s, 1H), 6.05 (q, 1H), 5.67 (d, J=6.8 Hz, 1H), 5.60 (d, 1H), 5.39 (m, 1H), 5.07 (m, 1H), 4.93 (d, 1H), 4.20-4.42 (m, 4H), 3.95 (s, 3H), 3.80 (s, 3H), 3.74 (d, J=6.4 Hz, 1H), 2.91-3.04 (m, 5H), 2.42 (s, 3H), 2.31-2.53 (m, 3H), 2.18 (d, 3H), 2.10 (m, 1H), 1.87 (s, 3H), 1.79-1.93 (m, 2H), 1.75 (s, 3H), 1.72 (s, 3H), 1.67 (d, 3H), 1.51-1.64 (m, 3H), 1.29 (s, 3H), 1.15 (s, 3H), 0.9 (t, 2H); LRMS m/z calculated for $C_{46}H_{61}NO_{16}S_2Na$ (M+Na)⁺ 970.33, found 970.2.

Compound 19.

¹H NMR (CDCl₃) δ 7.41 (s, 1H), 7.30 (m, 2H), 6.80 (m, 2H), 6.38 (m, 2H), 5.24 (d, J=4.8 Hz, 1H), 5.20 (d, J=5.2 Hz, 1H), 3.75 (s, 3H), 1.03 (s, 21 H); ¹³C NMR (CDCl₃) δ 165.33, 156.24, 148.27, 142.83, 130.91, 118.45, 114.29, 110.64, 110.26, 77.94, 57.06, 55.41, 17.55, 17.49, 11.80; LRMS m/z calculated for $C_{23}H_{33}NO_4SiNa$ (M+Na)⁺ 438.21, found 438.1.

Compound 20.

¹H NMR (CDCl₃) δ 7.39 (s, 1H), 6.54 (bs, 1H), 6.35 (m, 2H), 5.15 (m, 1H), 4.81 (d, J=4.4 Hz, 1H), 0.98 (s, 21H); ¹³C NMR (CDCl₃) δ 169.81, 150.49, 142.53, 110.48, 109.09, 80.03, 53.52, 17.49, 17.43, 11.73; LRMS m/z calculated for $C_{16}H_{27}NO_3SiNa$ (M+Na)⁺ 332.17, found 332.0.

Compound 21.

¹H NMR (CDCl₃) δ 7.38 (s, 1H), 7.13 (m, 1H), 6.80 (dd, 1H), 6.35 (m, 2H), 5.25 (d, J=5.6 Hz, 1H), 5.19 (d, J=5.6 Hz, 1H), 1.93 (dd, 3H), 0.98 (m, 21 H); ¹³C NMR (CDCl₃) δ 166.40, 162.72, 147.47, 146.94, 142.79, 123.57, 110.43, 109.82, 77.51, 54.96, 18.35, 17.45, 17.38, 11.71; LRMS m/z calculated for $C_{20}H_{31}NO_4SiNa$ (M+Na)⁺ 400.19, found 400.0.

Compound 22.

¹H NMR (CDCl₃) δ 7.38 (s, 1H), 6.61 (m, 1H), 6.34 (m, 2H), 5.23 (d, J=5.6 Hz, 1H), 5.15 (d, J=6 Hz, 1H), 2.18 (s, 3H), 1.95 (s, 3H), 0.98 (s, 21H); ¹³C NMR (CDCl₃) δ 166.08, 162.86, 160.95, 147.82, 142.67, 120.73, 117.02, 115.12, 110.40, 109.62, 77.11, 54.80, 27.96, 27.53, 21.33, 17.44, 17.37, 11.70; LRMS m/z calculated for $C_{21}H_{33}NO_4SiNa$ (M+Na)⁺ 414.21, found 414.0.

Compound 23.

¹H NMR (CDCl₃) δ 8.00 (m, 2H), 7.58 (tt, 1H), 7.42-7.48 (m, 3H), 6.45 (d, J=3.2 Hz, 1H), 6.38 (m, 1H), 5.47 (d, J=6 Hz, 1H), 5.23 (d, J=6 Hz, 1H), 0.99 (s, 21H); ¹³C NMR (CDCl₃) δ 166.22, 164.95, 147.77, 142.93, 133.34, 131.96, 129.89, 128.13, 110.47, 110.00, 76.81, 55.17, 17.48, 17.41, 11.73; LRMS m/z calculated for $C_{23}H_{31}NO_4SiNa$ (M+Na)⁺ 436.19, found 436.0.

Compound 24.

¹H NMR (CDCl₃) δ 7.40 (s, 1H), 6.36 (m, 2H), 5.14 (d, J=5.6 Hz, 1H), 5.11 (d, J=5.6 Hz, 1H), 1.43 (s, 9H), 0.96 (m, 21H); ¹³C NMR (CDCl₃) δ 165.76, 147.97, 147.75, 142.73, 110.45, 109.72, 83.46, 77.83, 56.16, 27.87, 17.44, 17.38, 11.69; LRMS m/z calculated for $C_{21}H_{35}NO_5SiNa$ (M+Na)⁺ 432.22, found 432.1.

Compound 25.

¹H NMR (CDCl₃) δ 8.03 (d, 1H), 7.65 (m, 1H), 7.39 (m, 1H), 6.56 (m, 1H), 6.42 (d, J=3.2 Hz, 1H), 6.34 (m, 1H), 5.45 (d, J=5.6 Hz, 1H), 5.23 (d, J=6 Hz, 1H), 0.99 (s, 21H); ¹³C NMR (CDCl₃) δ 164.52, 154.39, 147.56, 147.48, 145.45, 142.88, 120.86, 112.10, 110.44, 110.08, 76.56, 17.45, 17.38, 11.71; LRMS m/z calculated for $C_{21}H_{29}NO_5SiNa$ (M+Na)⁺ 426.17, found 426.0.

Compound 26.

¹H NMR (CDCl₃) δ 7.32 (s, 1H), 7.04 (dd, 1H), 6.93 (d, J=9.2 Hz, 1H), 6.78 (m, 1H), 6.45 (s, 1H), 6.31 (m, 1H), 6.16 (m, 2H), 5.86 (dd, 1H), 5.68 (d, J=6.8 Hz, 1H), 5.56 (d, J=9.2 Hz, 1H), 5.00 (s, 1H), 4.89 (d, J=8 Hz, 1H), 4.46 (m, 1H), 4.10 (d, J=8 Hz, 1H), 4.28 (d, J=8 Hz, 1H), 3.94 (s, 3H), 3.79 (s, 3H), 3.76 (m, 1H), 3.47 (m, 1H), 2.48 (m, 1H), 2.25 (s, 3H), 2.11 (s, 3H), 1.95 (s, 3H), 1.87 (m, 4H), 1.74 (s, 3H), 1.22 (s, 6H), 1.10 (s, 21H), 1.03 (t, 12H), 0.55 (m, 6H).

Compound 27.

¹H NMR (CDCl₃) δ 7.32 (s, 1H), 7.04 (dd, 1H), 6.93 (d, J=9.2 Hz, 1H), 6.45 (s, 1H), 6.31 (m, 1H), 6.16 (m, 2H), 6.05 (d, J=9.2 Hz, 1H), 5.57-5.69 (m, 3H), 4.99 (s, 1H), 4.91 (d, J=8 Hz, 1H), 4.44 (m, 2H), 4.28 (d, J=8 Hz, 1H), 3.94 (s, 3H), 3.79 (s, 3H), 3.76 (m, 1H), 2.31 (s, 3H), 2.11 (s, 3H), 2.09 (s, 3H), 2.04 (s, 3H), 1.87 (s, 3H), 1.74 (s, 3H), 1.22 (s, 6H), 1.10 (s, 21H), 1.03 (t, 12H), 0.55 (m, 6H); LRMS m/z calculated for $C_{60}H_{89}NO_{17}Si_2Na$ (M+Na)⁺ 1174.56, found 1174.3.

Compound 28.

¹H NMR (CDCl₃) δ 7.76 (d, 1H), 7.43-7.56 (m, 3H), 7.04 (dd, 1H), 6.93 (dd, 1H), 6.44 (s, 1H), 6.22 (m, 1H), 5.69 (m, 1H), 4.90 (m, 1H), 4.44 (m, 2 H), 4.30 (d, J=8 Hz, 1H), 3.87 (s, 3H), 3.79 (s, 3H), 3.76 (m, 1H), 2.31 (s, 1H), 2.19 (s, 3H), 2.02 (m, 2H), 1.74 (s, 3H), 0.88-1.13 (m, 33H), 0.58 (m, 6H); LRMS m/z calculated for $C_{62}H_{87}NO_{17}Si_2Na$ (M+Na)⁺ 1196.54, found 1196.3.

Compound 29.

¹H NMR (CDCl₃) δ 7.32 (s, 1H), 7.04 (dd, 1H), 6.92 (d, J=9.2 Hz, 1H), 6.45 (s, 1H), 6.32 (m, 1H), 6.22 (s, 1H), 6.18 (t, 1H), 5.67 (d, J=6.4 Hz, 1H), 5.25 (q, 2H), 4.94 (s, 1H), 4.91 (d, J=8 Hz, 1H), 4.44 (m, 2H), 4.29 (d, J=8 Hz, 1H), 3.93 (s, 3H), 3.78 (s, 3H), 3.76 (m, 1H), 2.50 (m, 1H), 2.37 (m, 1H), 2.29 (s, 3H), 2.17 (s, 3H), 2.00 (s, 3H), 1.74 (s, 3H), 1.41 (s, 9H), 1.38 (m, 2H), 1.22 (s, 3H), 1.20 (s, 3H), 1.06 (m, 6H), 0.83-0.98 (m, 30H), 0.55 (m, 6H); LRMS m/z calculated for $C_{60}H_{91}NO_{18}Si_2Na$ (M+Na)⁺ 1192.57, found 1192.3.

Compound 30.

¹H NMR (CDCl₃) δ 7.48 (s, 1H), 7.35 (s, 1H), 7.27 (d, J=3.2 Hz, 1H), 7.14 (d, J=9.6 Hz), 7.06 (d, 1H), 7.04 (d, J=3.2 Hz, 1H), 6.94 (d, J=9.2 Hz, 1 H), 6.51 (m, 1H), 6.45 (s, 1H), 6.33 (m, 1H), 6.24 (s, 1H), 6.20 (t, 1H), 5.69 (d, J=6.4 Hz, 1H), 5.64 (d, J=9.2 Hz), 5.06 (s, 1H), H), 4.91 (d, 1H), 4.44 (m, 2H), 4.29 (d, J=8 Hz, 1H), 3.95 (s, 3H), 3.81 (s, 3H), 3.79 (m, 1H), 3.18 (s, 1H), 2.50 (m, 1H), 2.37 (m, 1H), 2.33 (s, 3H), 2.16 (s, 3H), 2.01 (s, 3H), 1.92 (m, 1H), 1.74 (s, 3 H), 1.25 (s, 3H), 1.23 (s, 3H), 0.88-1.02 (m, 27H), 0.55 (m, 6H); LRMS m/z calculated for $C_{60}H_{85}NO_{18}Si_2Na$ (M+Na)⁺ 1186.52, found 1186.3.

Compound 31.

¹H NMR (CDCl₃) δ 7.39 (s, 1H), 7.30 (d, J=3.2 Hz, 1H), 7.07 (dd, 1H), 6.95 (d, J=9.2 Hz, 1H), 6.84 (m, 1H), 6.35 (m, 1H), 6.32 (m, 1H), 6.29 (s, 1H), 6.23 (t, 1H), 6.05 (d, J=9.2

Hz, 1H), 5.83 (dd, 1H), 5.65 (m, 2H), 4.92 (d, 1H), 4.71 (s, 1H), 4.40 (m, 2H), 4.30 (d, J=8 Hz, 1H), 3.91 (s, 3H), 3.75 (s, 3H), 3.73 (d, 1H), 3.40 (m, 1H), 3.06 (s, 1H), 2.56 (m, 1H), 2.34 (m, 3H), 2.22 (s, 3H), 2.17 (s, 3H), 1.85 (s, 6H), 1.70 (s, 3H), 1.29 (s, 3H), 1.25 (s, 1H), 1.16 (s, 3H); LRMS m/z calculated for $C_{44}H_{53}NO_{17}Na$ (M+Na)$^+$ 890.32, found 890.2.

Compound 32.

$^1$H NMR (CDCl$_3$) δ 7.39 (s, 1H), 7.30 (d, J=3.2 Hz, 1H), 7.07 (dd, 1H), 6.95 (d, J=9.2 Hz, 1H), 6.36 (m, 1H), 6.31 (m, 2H), 6.22 (t, 1H), 5.92 (d, J=9.2 Hz, 1H), 5.59-5.67 (m, 3H), 4.92 (d, 1H), 4.71 (m, 1H), 4.40 (m, 2H), 4.30 (d, J=8 Hz, 1H), 3.91 (s, 3H), 3.81 (s, 3H), 3.74 (d, 1H), 3.35 (d, 1H), 3.10 (s, 1H), 2.95 (s, 1H), 2.34-2.58 (m, 4H), 2.23 (s, 3H), 2.20 (s, 3H), 2.09 (s, 3H), 1.86 (s, 3H), 1.85 (s, 3H), 1.73 (s, 3H), 1.29 (s, 3H), 1.25 (s, 1H), 1.16 (s, 3H); LRMS m/z calculated for $C_{45}H_{55}NO_{17}Na$ (M+Na)$^+$ 904.34, found 904.2.

Compound 33.

$^1$H NMR (CDCl$_3$) δ 7.75 (d, 1H), 7.43-7.56 (m, 4H), 7.29 (d, J=2.8 Hz, 1H), 7.06 (dd, 1H), 6.95 (d, J=9.2 Hz, 1H), 6.38 (s, 1H), 6.29 (m, 2H), 5.83 (d, 1H), 5.66 (d, 1H), 4.91 (d, 1H), 4.79 (m, 1H), 4.41 (d, J=8 Hz, 1H), 4.40 (m, 1H), 4.33 (d, J=8 Hz, 1H), 3.95 (s, 3H), 3.81 (s, 3H), 3.77 (m, 1H), 3.12 (s, 1H), 2.42 (m, 1H), 2.25 (s, 3H), 2.24 (s, 3H), 1.86 (s, 3H), 1.73 (s, 3H), 1.29 (s, 3H), 1.25 (s, 3 H); LRMS m/z calculated for $C_{47}H_{53}NO_{17}Na$ (M+Na)$^+$ 926.32, found 926.2.

Compound 34.

$^1$H NMR (CDCl$_3$) δ 7.39 (s, 1H), 7.28 (d, J=2.8 Hz, 1H), 7.07 (dd, 1H), 6.95 (d, J=9.2 Hz, 1H), 6.36 (m, 1H), 6.31 (m, 2H), 6.21 (t, 1H), 5.67 (d, J=6.4 Hz, 1H), 5.26 (d, 1H), 5.19 (d, 1H), 4.93 (d, 1H), 4.68 (m, 1H), 4.40 (m, 2H), 4.30 (d, J=8 Hz, 1H), 3.93 (s, 3H), 3.80 (s, 3H), 3.74 (d, 1H), 3.17 (m, 2H), 2.38-2.57 (m, 4H), 2.24 (s, 3H), 2.22 (s, 3H), 1.88 (s, 3H), 1.73 (s, 3H), 1.41 (s, 9H), 1.29 (s, 3 H), 1.25 (s, 3H) 1.16 (s, 3H); LRMS m/z calculated for $C_{45}H_{57}NO_{18}Na$ (M+Na)$^+$ 922.35, found 922.2.

Compound 35.

$^1$H NMR (CDCl$_3$) δ 7.47 (s, 1H), 7.42 (s, 1H), 7.30 (d, J=3.2 Hz, 1H), 7.05-7.09 (m, 2H), 6.94-6.99 (m, 2H), 6.51 (m, 1H), 6.38 (m, 2H), 6.28 (m, 2H), 5.75 (dd, 1H), 5.68 (d, J=6.4 Hz, 1H), 4.93 (d, 1H), 4.77 (m, 1H), 4.40 (m, 2H), 4.31 (d, J=8.4 Hz, 1H), 3.95 (s, 3H), 3.81 (s, 3H), 3.74 (d, 1H), 3.46 (d, 1H), 3.08 (s, 1H), 2.55 (m, 1H), 2.36-2.43 (m, 4H), 2.23 (s, 6H), 1.85 (s, 3H), 1.73 (s, 3H), 1.29 (s, 3H), 1.16 (s, 3H); $^{13}$C NMR (CDCl$_3$) δ 204.21, 172.66, 171.62, 170.70, 167.21, 157.98, 153.84, 153.23, 151.08, 147.39, 144.88, 143.11, 142.26, 134.01, 120.59, 120.40, 116.10, 115.69, 113.95, 112.73, 111.16, 108.33, 84.95, 81.51, 78.01, 76.89, 76.61, 76.11, 73.14, 72.58, 72.03, 59.28, 57.11, 56.28, 49.81, 45.99, 43.26, 36.97, 36.15, 27.36, 22.97, 22.10, 21.25, 15.33, 9.94; LRMS m/z calculated for $C_{45}H_{51}NO_{18}Na$ (M+Na)$^+$ 916.30, found 916.2.

Compound 36.

$^1$H NMR (CDCl$_3$) δ 7.30 (t, 1H), 7.05 (dm, 1H), 6.95 (dd, 1H), 6.72 (m, 1H), 6.45 (s, 1H), 6.05 (bt, 1H), 5.76 (d, 1H), 5.67 (d, J=6.4 Hz, 1H), 5.38 (m, 1H), 5.09 (m, 1H), 4.88 (d, 1H), 4.39-4.48 (m, 3H), 4.27 (d, J=8.4 Hz, 1H), 3.98 (s, 3H), 3.81 (s, 3H), 3.64-3.80 (m, 22H), 3.56 (d, 1H), 2.90 (t, 2H), 2.74 (m, 2H), 2.41 (s, 3H), 2.16 (d, 3H), 2.10 (m, 1H), 2.00 (s, 3H), 1.90 (m, 1H), 1.81 (m, 1H), 1.71 (s, 6H), 1.69 (d, 3H), 1.61 (m, 2H), 1.21-1.31 (m, 14H), 1.21 (s, 21H), 0.92 (m, 16H), 0.58 (m, 6H).

Compound 37.

$^1$H NMR (CDCl$_3$) δ 7.32 (t, 1H), 7.07 (dm, 1H), 6.95 (d, J=9.2 Hz, 1H), 6.78 (m, 1H), 6.31 (s, 1H), 6.16 (q, 1H), 5.66 (d, 1H), 5.61 (d, 1H), 5.39 (m, 1H), 5.06 (m, 1H), 4.93 (d, 1H), 4.39 (m, 2H), 4.25 (d, 1H), 4.21 (ddd, 1H), 3.94 (s, 3H), 3.85 (d, 1H), 3.80 (s, 3H), 3.73 (t, 3H), 3.64-3.65 (m, 13H), 2.98 (d, 1H), 2.90 (t, 2H), 2.80 (t, 2H), 2.39 (s, 3H), 2.21 (d, 3H), 2.06 (m, 1H), 1.86 (s, 3H), 1.84 (m, 2H), 1.75 (s, 3H), 1.71 (s, 3H), 1.69 (d, 3H), 1.61 (m, 2H), 1.27 (s, 3H), 1.14 (s, 3H), 0.89 (t, 2H); $^{13}$C NMR (CDCl$_3$) δ 203.72, 173.09, 172.89, 172.28, 171.68, 170.16, 170.04, 166.74, 166.69, 165.27, 153.42, 153.01, 152.94, 142.36, 142.32, 140.84, 138.82, 138.63, 133.27, 124.49, 120.38, 120.26, 120.19, 115.88, 115.85, 113.57, 84.52, 81.03, 77.74, 77.63, 76.46, 75.79, 73.49, 73.28, 72.46, 72.24, 72.17, 70.64, 70.62, 70.56, 70.51, 70.40, 69.76, 66.36, 58.82, 56.70, 56.66, 55.86, 50.08, 49.76, 45.58, 42.84, 38.39, 37.59, 36.58, 35.76, 35.01, 26.93, 26.86, 25.64, 25.59, 23.47, 22.43, 21.77, 19.14, 18.51, 18.46, 17.74, 14.97, 14.94, 13.58, 9.54.

Compound 38.

$^1$H NMR (CDCl$_3$) δ 7.31 (m, 3H), 7.10 (d, 1H), 6.99 (dd, 1H), 6.78 (m, 2H), 5.41 (d, J=4.8 Hz, 1H), 5.23 (d, J=5.2 Hz, 1H), 3.73 (s, 3H), 1.01 (s, 21 H); $^{13}$C NMR (CDCl$_3$) δ 165.34, 156.22, 137.45, 130.81, 127.49, 126.64, 126.15, 118.65, 114.26, 78.02, 59.28, 55.37, 17.55, 17.46, 11.79; LRMS m/z calculated for $C_{23}H_{33}NO_3SSiNa$ (M+Na)$^+$ 454.18, found 454.0.

Compound 40.

$^1$H NMR (CDCl$_3$) δ 7.28 (dd, 1H), 7.11 (m, 2H), 6.98 (dd, 1H), 6.78 (dd, 1H), 5.50 (d, J=5.6 Hz, 1H), 5.21 (d, J=6 Hz, 1H), 1.93 (dd, 3H), 1.01 (s, 21H); $^{13}$C NMR (CDCl$_3$) δ 166.40, 162.70, 147.00, 136.39, 127.61, 126.54, 125.88, 123.61, 77.39, 57.01, 18.35, 17.67, 17.47, 17.37, 12.26, 11.72; LRMS m/z calculated for $C_{20}H_{31}NO_3SSiNa$ (M+Na)$^+$ 416.17, found 416.1.

Compound 41.

$^1$H NMR (CDCl$_3$) δ 7.28 (dd, 1H), 7.11 (m, 1H), 7.00 (dd, 1H), 6.80 (s, 1H), 6.26 (dd, 1H), 5.87 (dd, 1H), 5.50 (d, J=6 Hz, 1H), 5.19 (d, J=5.6 Hz, 1H), 2.35 (s, 1H), 2.20 (dd, 6H), 0.98 (m, 21H); $^{13}$C NMR (CDCl$_3$) δ 166.04, 164.59, 162.83, 160.70, 148.34, 136.96, 127.39, 126.50, 125.65, 122.38, 120.70, 117.18, 117.12, 115.25, 77.14, 56.90, 17.48, 17.39, 12.34, 11.82; LRMS m/z calculated for $C_{21}H_{33}NO_3SSiNa$ (M+Na)$^+$ 430.18, found 430.1.

Compound 42.

$^1$H NMR (CDCl$_3$) δ 7.99 (d, 2H), 7.57 (t, 1H), 7.47 (t, 2H), 7.30 (dd, 2H), 7.18 (d, 1H), 7.01 (t, 1H), 5.73 (d, J=6 Hz, 1H), 5.25 (d, J=6.4 Hz, 1H), 1.04 (m, 21H); $^{13}$C NMR (CDCl$_3$) δ 166.13, 164.82, 136.86, 129.89, 128.11, 127.80, 126.58, 125.96, 76.89, 57.11, 17.50, 17.41, 11.83; LRMS m/z calculated for $C_{23}H_{31}NO_3SSiNa$ (M+Na)$^+$ 452.17, found 452.0.

Compound 43.

$^1$H NMR (CDCl$_3$) δ 7.30 (dd, 1H), 7.08 (dd, 1H), 6.99 (dd, 1H), 5.34 (d, J=5.6 Hz, 1H), 5.15 (d, J=5.6 Hz, 1H), 1.42 (s, 9H) 0.95 (m, 21H); $^{13}$C NMR (CDCl$_3$) δ 165.75, 147.74, 136.80, 127.58, 126.48, 125.97, 122.05, 83.53, 77.76, 58.26, 27.88, 17.67, 17.47, 17.37, 12.26, 11.70; LRMS m/z calculated for $C_{21}H_{35}NO_4SSiNa$ (M+Na)$^+$ 448.20, found 448.1.

Compound 44.

$^1$H NMR (CDCl$_3$) δ 7.98 (d, 1H), 7.65 (dd, 1H), 7.29 (dd, 1H), 7.15 (dd, 1H), 6.99 (dd, 1H), 6.56 (m, 1H), 5.71 (d, J=6 Hz, 1H), 5.25 (d, J=6 Hz, 1H), 0.99 (m, 21H); $^{13}$C NMR (CDCl$_3$) δ 164.11, 147.61, 127.96, 126.57, 126.06, 120.95, 112.12, 76.52, 57.17, 17.67, 17.50, 17.39, 11.74; LRMS m/z calculated for $C_{21}H_{29}NO_4SSiNa$ (M+Na)$^+$ 442.15, found 442.0.

Compound 45.

¹H NMR (CDCl₃) δ 7.27 (d, 1H), 7.20 (d, 1H), 7.05 (dd, 1H), 6.87-6.95 m, 4H), 6.76 (m, 1H), 6.45 (s, 1H), 6.27 (d, J=9.2 Hz, 1H), 6.17 (t, 1H), 5.85 (d, 1H), 5.75 (d, J=9.2 Hz, 1H), 5.68 (d, J=6.8 Hz, 1H), 4.92 (d, 1H), 4.83 (s, 1 H), 4.40-4.45 (m, 2H), 4.28 (d, J=8 Hz, 1H), 3.96 (s, 3H), 3.84 (d, 1H), 3.82 (s, 3H), 3.79 (d, 1H), 3.46 (m, 1H), 3.19 (s, 1H), 2.34-2.49 (m, 3H), 2.30 (s, 3H), 2.17 (s, 3 H), 2.00 (s, 3H), 1.85-1.97 (m, 9H), 1.72 (s, 3H), 1.55-1.67 (m, 5H), 1.23 (s, 6H), 1.00 (s, 21H), 0.92 (t, 9H), 0.58 (m, 6H); LRMS m/z calculated for $C_{59}H_{87}NO_{16}SSi_2Na$ (M+Na)⁺ 1176.52, found 1176.4.

Compound 46.

¹H NMR (CDCl₃) δ 7.27 (d, 1H), 7.20 (d, 1H), 7.05 (dd, 1H), 6.87-6.95 (m, 4H), 6.45 (s, 1H), 6.15-6.19 (m, 2H), 5.78 (d, 1H), 5.68 (d, J=6.8 Hz, 1H), 5.60 (s, 1H), 4.90 (d, 1H), 4.82 (s, 1H), 4.40-4.46 (m, 2H), 4.29 (d, J=8 Hz, 1H), 3.96 (s, 3H), 3.84 (d, 1H), 3.82 (s, 3H), 3.76 (d, 1H), 3.46 (m, 1H), 3.23 (s, 1H), 2.49 (m, 1H), 2.34 (m, 2H), 2.31 (s, 3H), 2.17 (m, 2H), 2.14 (s, 3H), 2.07 (s, 3H), 2.01 (s, 3H), 1.85-1.97 (m, 9H), 1.83 (s, 3H), 1.71 (s, 3H), 1.55-1.67 (m, 3H), 1.39 (m, 1H), 1.23 (s, 6H), 1.00 (s, 21H), 0.92 (t, 9H), 0.58 (m, 6H); LRMS m/z calculated for $C_{60}H_{89}NO_{16}SSi_2Na$ (M+Na)⁺ 1190.53, found 1190.5.

Compound 47.

¹H NMR (CDCl₃) δ 7.53-7.60 (m, 3H), 7.42-7.46 (t, 2H), 7.20 (d, 1H), 7.13-7.15 (m, 3H), 6.92-7.01 (m, 3H), 6.54 (d, J=9.2 Hz, 1H), 6.45 (s, 1H), 6.20 (d, 1H), 5.84 (m, 1H), 5.56 (d, J=6.4 Hz, 1H), 4.92 (m, 1H), 4.84 (s, 1H), 4.65 (d, 1H), 4.64 (d, 1H), 4.22 (d, J=8 Hz, 1H), 4.08 (m, 1H), 3.79 (m, 2H), 3.74 (s, 3H), 3.30 (m, 1H), 3.25 (s, 3H), 2.67 (m, 1H), 2.46 (m, 2H), 2.18 (s, 3H), 2.17 (m, 2H), 2.07 (s, 3H), 1.69 (s, 3H), 1.21 (s, 3H), 1.18 (s, 3H), 1.17 (s, 3H), 1.13 (m, 21H), 0.92 (t, 9H), 0.58 (m, 6H); LRMS m/z calculated for $C_{62}H_{87}NO_{16}SSi_2Na$ (M+Na)⁺ 1212.52, found 1212.5.

Compound 48.

¹H NMR (CDCl₃) δ 7.27 (d, 1H), 7.21 (d, 1H), 7.06 (dd, 1H), 6.90-6.97 (m, 3H), 6.46 (s, 1H), 6.17 (t, 1H), 5.68 (d, J=6.8 Hz, 1H), 5.43 (d, 1H), 5.42 (d, 1H), 4.90 (d, 1H), 4.76 (s, 1H), 4.41-4.46 (m, 2H), 4.29 (d, J=8 Hz, 1H), 3.94 (s, 3H), 3.79 (s, 3H), 3.77 (d, 1H), 3.24 (s, 1H), 2.52 (m, 1H), 2.41 (m, 2H), 2.30 (s, 3H), 2.01 (s, 3H), 1.88 (s, 1H), 1.73 (s, 3H), 1.40 (s, 9H), 1.23 (s, 3H), 1.22 (s, 3H), 1.00 (s, 21H), 0.92 (t, 9H), 0.58 (m, 6H); LRMS m/z calculated for $C_{60}H_{91}NO_{17}SSi_2Na$ (M+Na)⁺ 1208.54, found 1208.5.

Compound 49.

¹H NMR (CDCl₃) δ 7.47 (s, 1H), 7.22-7.29 (m, 3H), 7.06 (d, 1H), 7.05 (d, 1H), 6.94-6.98 (m, 3H), 6.50 (m, 1H), 6.44 (s, 1H), 6.19 (t, 1H), 5.84 (d, 1H), 5.69 (d, J=6.8 Hz, 1H), 4.90 (d, 1H), 4.89 (s, 1H), 4.41-4.46 (m, 2H), 4.29 (d, J=8.4 Hz, 1H), 3.98 (s, 3H), 3.82 (s, 3H), 3.77 (d, 1H), 3.16 (s, 1H), 2.52 (m, 1H), 2.36 (m, 3H), 2.31 (s, 3H), 2.24 (m, 1H), 2.15 (s, 3H), 2.00 (s, 3H), 1.88 (s, 1H), 1.72 (s, 3H), 1.17 (s, 6H), 1.00 (s, 21H), 0.92 (t, 9H), 0.58 (m, 6H); LRMS m/z calculated for $C_{60}H_{85}NO_{17}SSi_2Na$ (M+Na)⁺ 1202.50, found 1202.4.

Compound 50.

¹H NMR (CDCl₃) δ 7.32 (d, 1H), 7.27 (dd, 1H), 7.06-7.10 (m, 2H), 6.95-7.01 (m, 2H), 6.80 (m, 1H), 6.28 (s, 1H), 6.23 (t, 1H), 6.10 (d, J=9.2 Hz, 1H), 5.77-5.84 (m, 2H), 5.66 (d, J=6.8 Hz, 1H), 4.92 (d, 1H), 4.67 (s, 1H), 4.40 (d, J=8.8 Hz, 1H), 4.35 (m, 1H), 4.29 (d, J=8 Hz, 1H), 3.96 (s, 3H), 3.82 (s, 3H), 3.73 (d, J=6.4 Hz, 1H), 3.54 (bs, 1H), 3.06 (bs, 1H), 2.55 (m, 1H), 2.38 (m, 3H), 2.24 (s, 3H), 2.20 (s, 3H), 1.84 (dd, 3H), 1.82 (s, 3H), 1.29 (s, 3H), 1.16 (s, 3H); ¹³C NMR (CDCl₃) δ 203.82, 172.30, 171.23, 170.22, 166.79, 164.91, 153.44, 152.91, 141.88, 141.56, 140.94, 133.58, 127.06, 125.82, 125.59, 124.25, 120.32, 119.91, 115.68, 113.59, 99.99, 84.51, 81.15, 77.60, 76.50, 76.12, 75.72, 73.06, 72.76, 72.20, 58.88, 56.74, 55.90, 50.77, 45.58, 42.87, 36.56, 35.75, 26.96, 22.68, 21.67, 20.86, 17.82, 14.98, 9.53; LRMS m/z calculated for $C_{44}H_{53}NO_{16}SNa$ (M+Na)⁺ 906.3, found 906.2.

Compound 51.

¹H NMR (CDCl₃) δ 7.32 (d, 1H), 7.27 (dd, 1H), 7.06-7.09 (m, 2H), 6.94-6.99 (m, 2H), 6.29 (s, 1H), 6.22 (t, 1H), 6.01 (d, J=9.2 Hz, 1H), 5.79 (d, 1H), 5.66 (d, J=6.8 Hz, 1H), 5.56 (s, 1H), 4.92 (d, 1H), 4.65 (s, 1H), 4.40 (d, J=8 Hz, 1H), 4.35 (m, 1H), 4.30 (d, J=8.4 Hz, 1H), 3.95 (s, 3H), 3.82 (s, 3H), 3.74 (d, J=6.4 Hz, 1H), 3.52 (bs, 1H), 3.07 (bs, 1H), 2.34-2.57 (m, 4H), 2.24 (s, 3H), 2.21 (s, 3H), 1.84 (s, 6H), 1.72 (s, 3H), 1.29 (s, 3H), 1.15 (s, 3H); ¹³C NMR (CDCl₃) δ 203.82, 172.51, 171.23 170.14, 166.79, 165.83, 153.43, 153.19, 152.87, 142.01, 141.21, 133.49, 127.05, 125.64, 125.45, 120.32, 119.90, 117.48, 115.62, 113.55, 84.51, 81.11, 77.56, 76.18, 75.73, 73.17, 72.90, 72.18, 58.85, 56.68, 55.89, 50.57, 45.57, 42.86, 35.73, 27.21, 26.85, 22.67, 21.68, 20.86, 19.84, 14.96, 9.52; LRMS m/z calculated for $C_{45}H_{55}NO_{16}SNa$ (M+Na)⁺ 920.31, found 920.2.

Compound 52.

¹H NMR (CDCl₃) δ 7.66 (dd, 2H), 7.53 (tt, 1H), 7.43 (t, 2H), 7.33 (d, 1H), 7.22 (dd, 1H), 6.97-7.06 (m, 3H), 6.76 (d, 1H), 6.27 (s, 1H), 6.16 (d, 1H), 5.91 (d, 1H), 5.62 (d, J=6.4 Hz, 1H), 4.96 (bs, 1H), 4.89 (dd, 1H), 4.74 (s, 1H), 4.52 (d, J=7.6 Hz, 1H), 4.16 (d, J=7.6 Hz, 1H), 4.00 (m, 1H), 3.80 (s, 3H), 3.63 (s, 3H), 3.34 (d, J=6.4 Hz, 1H), 2.87 (bs, 1H), 2.40-2.61 (m, 4H), 2.24 (s, 3H), 1.99 (m, 1H), 1.77 (s, 3H), 1.66 (s, 3H), 1.13 (s, 3H), 1.12 (s, 3H); LRMS m/z calculated for $C_{47}H_{53}NO_{16}SNa$ (M+Na)⁺ 942.30, found 942.2.

Compound 53.

¹H NMR (CDCl₃) δ 7.30 (d, 1H), 7.27 (dd, 1H), 7.06-7.09 (m, 2H), 6.94-7.00 (m, 2H), 6.30 (s, 1H), 6.21 (t, 1H), 5.66 (d, J=6.8 Hz, 1H), 5.42 (d, 1H), 5.28 (d, 1H), 4.91 (d, 1H), 4.59 (s, 1H), 4.41 (d, J=8 Hz, 1H), 4.38 (m, 1H), 4.30 (d, J=8.4 Hz, 1H), 3.94 (s, 3H), 3.81 (s, 3H), 3.74 (d, J=6.4 Hz, 1H), 3.48 (bs, 1H), 3.11 (bs, 1H), 2.34-2.57 (m, 4H), 2.22 (s, 3H), 2.19 (s, 3H), 1.89 (m, 1H), 1.85 (s, 3H), 1.72 (s, 3H), 1.39 (s, 9H), 1.29 (s, 3H), 1.15 (s, 3H); ¹³C NMR (CDCl₃) δ 203.83, 172.63, 171.20, 170.00, 166.81, 154.88, 153.45, 152.74, 142.06, 141.29, 133.46, 127.05, 125.36, 120.23, 119.99, 115.61, 113.47, 84.51, 81.11, 80.36, 77.51, 76.43, 75.72, 73.21, 73.00, 72.15, 58.84, 56.54, 55.85, 45.58, 42.85, 36.47, 35.72, 28.12, 26.73, 22.63, 20.84, 14.95, 9.51; LRMS m/z calculated for $C_{45}H_{57}NO_{17}SNa$ (M+Na)⁺ 938.32, found 938.2.

Compound 54.

¹H NMR (CDCl₃) δ 7.46 (s, 1H), 7.32 (d, 1H), 7.28 (dd, 1H), 7.16 (d, 1H), 6.95-7.09 (m, 4H), 6.50 (m, 1H), 6.28 (s, 1H), 6.25 (t, 1H), 5.93 (d, 1H), 5.67 (d, J=6.8 Hz, 1H), 4.92 (d, 1H), 4.73 (s, 1H), 4.41 (d, J=8.4 Hz, 1H), 4.38 (m, 1H), 4.30 (d, J=8.4 Hz, 1H), 3.96 (s, 3H), 3.80 (s, 3H), 3.74 (d, J=6.4 Hz, 1H), 3.63 (bs, 1H), 3.09 (bs, 1H), 2.33-2.58 (m, 4H), 2.22 (s, 3H), 2.19 (s, 3H), 1.89 (m, 1H), 1.82 (s, 3H), 1.73 (s, 3H), 1.28 (s, 3H), 1.15 (s, 3H); LRMS m/z calculated for $C_{45}H_{51}NO_{17}SNa$ (M+Na)⁺ 932.28, found 932.2.

Example 10

In Vitro Cytotoxicity Assays

The new taxoids and the disulfide containing taxane drugs of the invention were evaluated for their ability to suppress proliferation of human tumor cell lines in vitro. The human tumor cell lines A-549 (human lung carcinoma) and MCF-7 (human breast tumor), are used for the assessment of cytotoxicity of these compounds. Cells are exposed to the compounds for 72 hours and the surviving fractions of cells are measured in direct assays. A549 and MCF-7 are assayed for plating efficiency (Goldmacher et al, J. Cell. Biol. 102: 1312-1319 (1986) and IC50 values are then calculated from this data.

The cytotoxicity of taxoids 14, 15, 31-35, 50-54 and disulfide-containing taxoids 18 and 37 was measured as follows. A549 and MCF-7 cells were plated at different densities in 6-well tissue-culture plates in DMEM medium supplemented with 10% fetal calf serum. The taxane, at varying concentrations, was added and the cells were maintained in a humidified atmosphere at 37° C. and 6% $CO_2$ until colonies of approximately 20 cells or more were formed (6 to 10 days). Control plates contained no taxane. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

FIG. 10 shows the results of the cytotoxicity determination of twelve new taxoids of the present invention. Except for taxane 52, which bears a phenyl substituent at R4, all the other new taxoids were extremely potent towards both A-549 and MCF-7 cell lines with $IC_{50}$ values in the $10^{-10}$ to $10^{-11}$ M range. Taxane 52 was less cytotoxic with an $IC_{50}$ value of $3 \times 10^{-9}$ M towards both cell lines that were tested.

FIG. 11 shows the cytotoxicity curves for representative disulfide-containing taxoids of the present invention. Disulfide-containing taxoids 18 and 37 are both extremely potent toward both A-549 and MCF-7 cells and display steep killing curves.

What is claimed is:

1. A cytotoxic agent composed of one or more compounds of formula (I-1) covalently bonded to a cell-binding agent through a link from the oxygen atom at the C-7 position of formula (I-1):

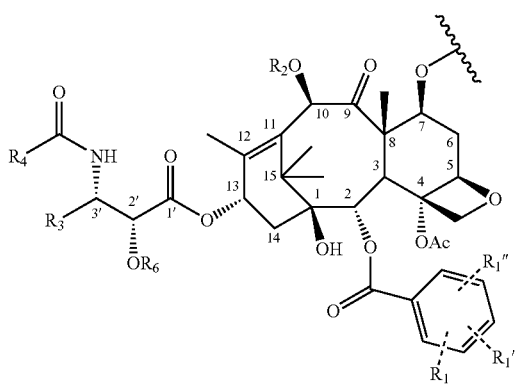

Formula (I-1)

wherein:

$R_1$ is H, an electron withdrawing group, or an electron donating group; $R_1'$ and $R_1''$ are the same or different, and are H, an electron withdrawing group, or an electron donating group;

$R_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms;

$R_3$ is alkenyl having from 2 to 10 carbon atoms, cycloalkenyl having from 3 to 10 carbon atoms or heterocyclic;

$R_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl or heterocyclic and an oxygen atom; and $R_6$ is H, or together with the oxygen atom at the C-2' position, a heterocyclic or aryl ether, a heterocyclic or aryl ester, a heterocyclic or aryl carbamate, a linear, branched or cyclic alkyl ester group having from 1 to 10 carbon atoms in the alkyl, a linear, branched or cyclic alkenyl ester group having from 2 to 10 carbon atoms in the alkenyl, a linear, branched, or cyclic alkyl ether group having from 1 to 10 carbon atoms, a linear, branched, or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms provided that when $R_3$ is —CH=C(CH$_3$)$_2$, $R_4$ is not an aryl or —OC(CH$_3$)$_3$, and wherein the cell-binding agent is selected from the group consisting of antibodies and fragments thereof, interferons, lymphokines, hormones, vitamins, growth factors, colony-stimulating factors and transferrin.

2. The cytotoxic agent of claim 1, wherein $R_2$ is H.

3. The cytotoxic agent of claim 2, wherein $R_3$ is —CH=C(CH$_3$)$_2$.

4. A cytotoxic agent composed of one or more compounds of formula (I-2) covalently bonded to a cell-binding agent through a link from the oxygen atom at the C-10 position of formula (I-2):

Formula (I-2)

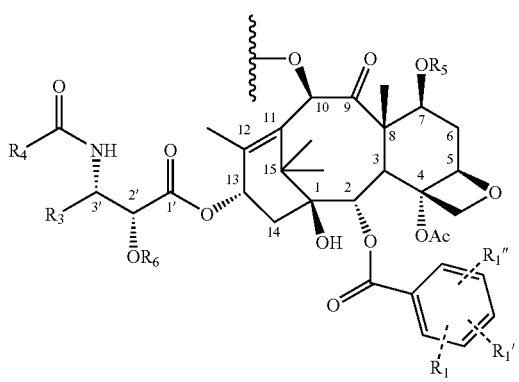

wherein:
R$_1$ is H, an electron withdrawing group or an electron donating group;
R$_1$' and R$_1$" are the same or different and are H, an electron withdrawing group, or an electron donating group;
R$_3$ is alkenyl having from 2 to 10 carbon atoms, cycloalkenyl having from 3 to 10 carbon atoms or heterocyclic;
R$_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl or heterocyclic and an oxygen atom;
R$_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms; and
R$_6$ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, provided that when R$_3$ is —CH=C(CH$_3$)$_2$, R$_4$ is not an aryl or —OC(CH$_3$)$_3$, and
wherein the cell-binding agent is selected from the group consisting of antibodies and fragments thereof, interferons, lymphokines, hormones, vitamins, growth factors, colony-stimulating factors and transferrin.

5. A cytotoxic agent composed of one or more compounds of formula (I-3) covalently bonded to a cell-binding agent through a link from the oxygen atom at the C-2' position of formula (I-3):

Formula (I-3)

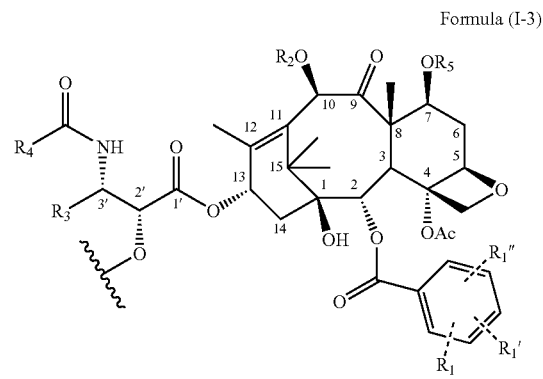

wherein:
R$_1$ is H, an electron withdrawing group or an electron donating group;
R$_1$' and R$_1$" are the same or different and are H, an electron withdrawing group, or an electron donating group;
R$_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms;
R$_3$ is alkenyl having from 2 to 10 carbon atoms, cycloalkenyl having from 3 to 10 carbon atoms or heterocyclic;
R$_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl, having from 1 to 10 carbon atoms, alkenyl having from 2 to 10 carbon atoms, cycloalkyl or cycloalkenyl having from 3 to 10 carbon atoms, aryl or heterocyclic and an oxygen atom; and
R$_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, provided that when R$_3$ is —CH═C(CH$_3$)$_2$, R$_4$ is not an aryl or —OC(CH$_3$)$_3$, and wherein the cell-binding agent is selected from the group consisting of antibodies and fragments thereof, interferons, lymphokines, hormones, vitamins, growth factors, colony-stimulating factors and transferrin.

6. The cytotoxic agent of claim 5, wherein R$_2$ is H.

7. A cytotoxic agent composed of one or more compounds of formula (I-4) covalently bonded to a cell-binding agent through a link from the C-3' carbon atom of formula (I-4):

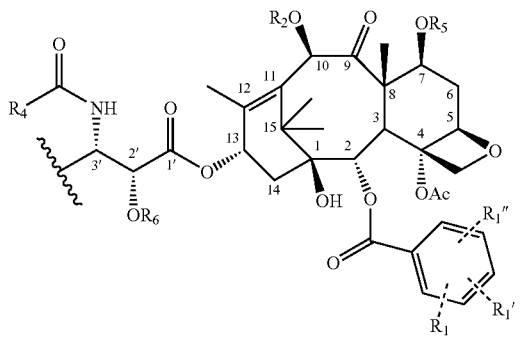

Formula (I-4)

wherein:

R$_1$ is H, an electron withdrawing group or an electron donating group;

R$_1$' and R$_1$" are the same or different and are H, an electron withdrawing group, or an electron donating group;

R$_4$ is alkyl having from 1 to 10 carbon atoms, alkenyl having from 2 to 10 carbon atoms, cycloalkyl or cycloalkenyl having from 3 to 10 carbon atoms, aryl, or heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl or heterocyclic and an oxygen atom; and R$_2$, R$_5$ and R$_6$ are the same or different and are H, or together with the oxygen atoms at the C-10, C-7 and C-2' positions, respectively, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, and wherein the cell-binding agent is selected from the group consisting of antibodies and fragments thereof, interferons, lymphokines, hormones, vitamins, growth factors, colony-stimulating factors and transferrin.

8. A cytotoxic agent composed of one or more compounds of formula (I-5) covalently bonded to a cell-binding agent through a link from the carbon atom at the C-3'N position of formula (I-5):

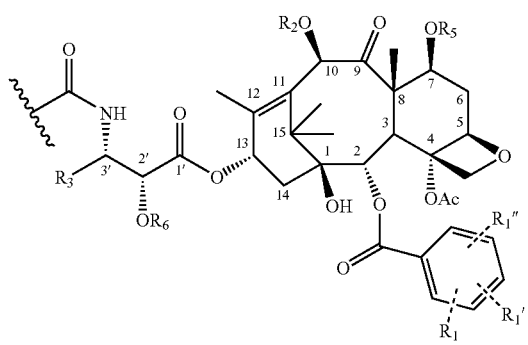

Formula (I-5)

wherein:

R$_1$ is H, an electron withdrawing group or an electron donating group;

R$_1$' and R$_1$" are the same or different and are H, an electron withdrawing group, or an electron donating group;

R$_3$ is alkyl having from 1 to 10 carbon atoms, alkenyl having from 2 to 10 carbon atoms, cycloalkyl or cycloalkenyl having from 3 to 10 carbon atoms, aryl or heterocyclic; and R$_2$, R$_5$ and R$_6$ are the same or different and are H, or together with the oxygen atoms at the C-10, C-7 and C-2' positions, respectively, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, and wherein the cell-binding agent is selected from the group consisting of antibodies and fragments thereof, interferons, lymphokines, hormones, vitamins, growth factors, colony-stimulating factors and transferrin.

9. A cytotoxic agent composed of one or more compounds of formula (I-3) covalently bonded to a cell-binding agent through a link from the oxygen atom at the C-2' position of formula (I-3):

Formula (I-3)

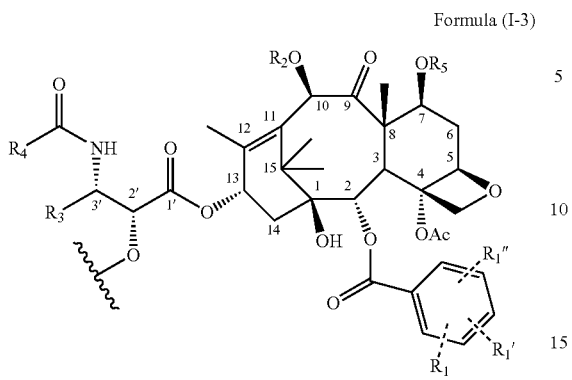

wherein:
R₁ is H, an electron withdrawing group or an electron donating group;
R₁' and R₁" are the same or different and are H, an electron withdrawing group, or an electron donating group;
R₂ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR₁₀R₁₁, wherein R₁₀ and R₁₁ are the same or different and are H, linear, branched or cyclic alkyl having from 1 to 10 carbon atoms, or simple or substituted aryl having from 1 to 10 carbon atoms;
R₃ is alkyl having from 1 to 10 carbon atoms, alkenyl having from 2 to 10 carbon atoms, cycloalkyl or cycloalkenyl having from 3 to 10 carbon atoms, aryl or heterocyclic;
R₄ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl, having from 1 to 10 carbon atoms, alkenyl having from 2 to 10 carbon atoms, cycloalkyl or cycloalkenyl having from 3 to 10 carbon atoms, aryl or heterocyclic and an oxygen atom; and
R₅ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR₁₀R₁₁, wherein R₁₀ and R₁₁ are the same or different and are H, linear, branched or cyclic alkyl having from 1 to 10 carbon atoms, or simple or substituted aryl having from 1 to 10 carbon atoms, and wherein the cell-binding agent is selected from the group consisting of antibodies and fragments thereof, interferons, lymphokines, hormones, vitamins, growth factors, colony-stimulating factors and transferrin.

10. The compound of claim 9, wherein R₂ is H.

11. A cytotoxic agent composed of one or more compounds of formula (I-2) covalently bonded to a cell-binding agent through a link from the oxygen atom at the C-10 position of formula (I-2):

Formula (I-2)

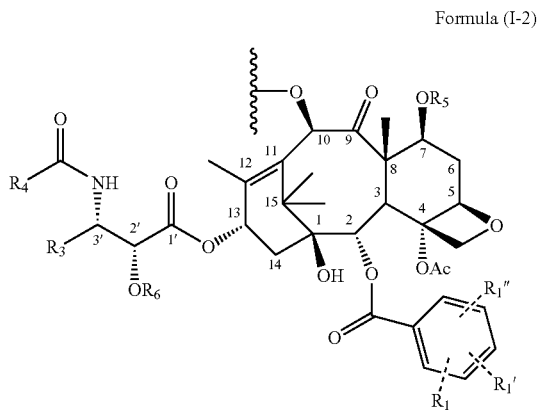

wherein:
R₁ is H, an electron withdrawing group or an electron-donating group;
R₁' and R₁" are the same or different and are H, an electron withdrawing group, or an electron donating group;
R₃ is alkyl or alkenyl having from 1 to 10 carbon atoms, cycloalkyl or cycloalkenyl having from 3 to 10 carbon atoms, aryl, or heterocyclic;
R₄ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl having from 1 to 10 carbon atoms, alkenyl having from 2 to 10 carbon atoms, cycloalkyl or cycloalkenyl having from 3 to 10 carbon atoms, aryl, or heterocyclic and an oxygen atom;
R₅ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR₁₀R₁₁, wherein R₁₀ and R₁₁ are the same or different and are H, linear, branched or cyclic alkyl having from 1 to 10 carbon atoms, or simple or substituted aryl having from 6 to 10 carbon atoms; and
R₆ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms, and wherein the cell-binding agent is selected from the group consisting of antibodies and fragments thereof, interferons, lymphokines, hormones, vitamins, growth factors, colony-stimulating factors and transferrin.

12. A cytotoxic agent composed of one or more compounds of formula (I-1) covalently bonded to a cell-binding agent through a link from the oxygen atom at the C-7 position of formula (I-1):

Formula (I-1)

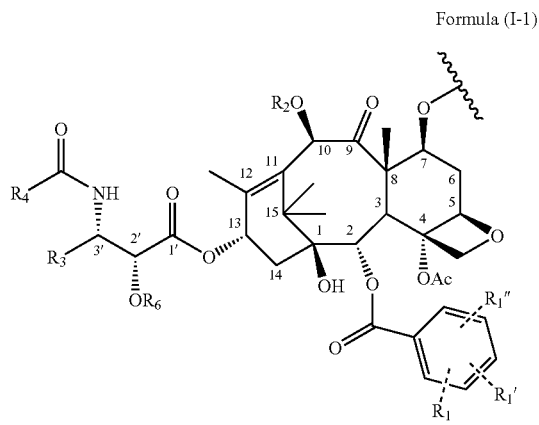

Wherein:
R$_1$ is H, an electron withdrawing group or an electron donating group;

R$_1$' and R$_1$" are the same or different and are H, an electron withdrawing group, or an electron donating group;

R$_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms;

R$_3$ is alkyl or alkenyl having from 1 to 10 carbon atoms, cycloalkyl or cycloalkenyl having from 3 to 10 carbon atoms, aryl, or heterocyclic;

R$_4$ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl having from 1 to 10 carbon atoms, alkenyl having from 2 to 10 carbon atoms, cycloalkyl or cycloalkenyl having from 3 to 10 carbon atoms, aryl, or heterocyclic and an oxygen atom; and R$_6$ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms, and wherein the cell-binding agent is selected from the group consisting of antibodies and fragments thereof, interferons, lymphokines, hormones, vitamins, growth factors, colony-stimulating factors and transferrin.

13. The cytotoxic agent of any one of claims 1 to 12, wherein the electron withdrawing group represented by R$_1$ and/or R$_1$' and/or R$_1$" is selected from the group consisting of F, NO$_2$, CN, Cl, CHF$_2$ and CF$_3$.

14. The cytotoxic agent of any one of claims 1 to 12, wherein the electron donating group represented by R$_1$ and/or R$_1$' and/or R$_1$" is selected from the group consisting of —OCH$_3$, —OCH$_2$CH$_3$, —NR$_7$R$_8$ and —OR$_9$, wherein R$_7$ and R$_8$ are the same or different and are linear, branched, or cyclic alkyl groups having from 1 to 10 carbon atoms, or simple or substituted aryl, and R$_9$ is linear, branched or cyclic alkyl having from 1 to 10 carbon atoms.

15. The cytotoxic agent of any one of claims 1 to 12, wherein R$_1$ is —OCH$_3$.

16. The cytotoxic agent of claim 14, wherein R$_7$ and/or R$_8$ have 1 to 4 carbon atoms.

17. The cytotoxic agent of claim 14, wherein R$_7$ and R$_8$ are the same.

18. The cytotoxic agent of claim 14, wherein —NR$_7$R$_8$ is dimethyl amino, diethyl amino, dipropyl amino, di-isopropylamino or dibutyl amino, where the butyl moiety is any of primary, secondary, tertiary and isobutyl.

19. The cytotoxic agent of any one of claims 1 to 12, wherein R$_1$ is in the meta position, and one of R$_1$' and R$_1$" is —OCH$_3$ and the other is H.

20. The cytotoxic agent of any one of claims 1, 2 and 4-6, wherein one or both of R$_3$ and R$_4$ are propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl, or R$_4$ is together with the —CONH— group at the C-3' position, a carbamate formed from t-butyl, propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl and an oxygen atom.

21. The cytotoxic agent of any one of claims 9-12, wherein one or both of R$_3$ and R$_4$ are propenyl, isobutenyl, hexenyl, cyclopentenyl, cyclohexenyl, furyl, pyrollyl, thiazolyl, imidazolyl, pyridyl, morpholino, piperidino, piperazino, oxazolyl, indolyl, benzofuranyl, or benzothiopheneyl, or R$_4$ is together with the —CONH— group at the C-3' position, a carbamate formed from propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl, or benzothiopheneyl and an oxygen atom.

22. The cytotoxic agent of claim 3, wherein R$_4$ is t-butoxy, propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofiiranyl, benzothiopheneyl, or together with the —CONH— group at the C-3' position, a carbamate formed from propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl and an oxygen atom.

23. The cytotoxic agent of claim 7, wherein R$_4$ is t-butoxy, propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl, or together with the —CONH— group at the C-3' position, a carbamate formed from propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl and an oxygen atom.

24. The cytotoxic agent of claim 8, wherein R$_3$ is propenyl, isobutenyl, hexenyl, cyclopentenyl, cyclohexenyl, furyl, pyrollyl, thiopheneyl, thiazolyl, imidazolyl, pyridyl, morpholino, piperidino, piperazino, oxazolyl, indolyl, benzofuranyl or benzothiopheneyl.

25. The cytotoxic agent of any one of claims 1, 2 and 4-6, wherein one or both of R$_3$ and R$_4$ are isobutenyl, propenyl, thiopheneyl, thiazolyl or furyl, or R$_4$ is together with the —CONH— group at the C-3' position, a carbamate formed from t-butoxy, isobutenyl, propenyl, thiopheneyl, thiazolyl or furyl and an oxygen atom.

26. The compound of claim 9, wherein one or both of R$_3$ and R$_4$ are isobutenyl, propenyl, thiopheneyl, thiazolyl or furyl, or R$_4$ is together with the —CONH— group at the C-3' position, a carbamate formed from isobutenyl, propenyl, thiopheneyl, thiazolyl or furyl and an oxygen atom.

27. The cytotoxic agent of claim 3, wherein R$_4$ is t-butoxy, isobutenyl, propenyl, thiopheneyl, thiazolyl, furyl, or together with the —CONH— group at the C-3' position, a carbamate formed from isobutenyl, propenyl, thiopheneyl, thiazolyl or furyl and an oxygen atom.

28. The cytotoxic agent of claim 7, wherein R$_4$ is t-butoxy, isobutenyl, propenyl, thiopheneyl, thiazolyl or furyl, or together with the —CONH— group at the C-3' position, a carbamate formed from isobutenyl, propenyl, thiopheneyl, thiazolyl or furyl and an oxygen atom.

29. The cytotoxic agent of claim 8, wherein R$_3$ is isobutenyl, propenyl, thiopheneyl, thiazolyl or furyl.

30. The cytotoxic agent of claim 1 or 12, wherein the carbamate formed by OR$_2$ and/or OR$_6$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

31. The cytotoxic agent of claim 2 or 3, wherein the carbamate formed by OR$_6$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

32. The cytotoxic agent of claim 4 or 11, wherein the carbamate formed by OR$_5$ and/or OR$_6$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

33. The cytotoxic agent of claim 5 or 9, wherein the carbamate formed by OR$_2$ and/or OR$_5$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

34. The cytotoxic agent of claim 6, wherein the carbamate formed by OR$_5$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

35. The cytotoxic agent of claim 7 or 8, wherein the carbamate formed by OR$_2$ and/or OR$_5$ and/or OR$_6$ is —OCONHCH$_2$CH$_3$, —OCONHCH$_2$CH$_2$CH$_3$, —OCO-morpholino, —OCO-piperazino, —OCO-piperidino or —OCO—N-methylpiperazino.

36. The cytotoxic agent of any one of claims 1 to 12 wherein the cell-binding agent is selected from the group consisting of antibodies and fragments thereof.

37. The cytotoxic agent of any one of claims 1 to 12 wherein the cell-binding agent is a monoclonal antibody or fragment thereof.

38. The cytotoxic agent of any one of claims 1 to 12 wherein the link is selected from the group consisting of a disulfide link, a thioether link, an acid labile link, a photolabile link, a peptidase labile link and an esterase labile link.

39. The cytotoxic agent of any one of claims 1 to 12 wherein the link is a disulfide or thioether link.

40. The cytotoxic agent of claim 39, wherein the disulfide or thioether link is formed from a linking group of a taxane, wherein the linking group is —(CR$_{13}$R$_{14}$)$_m$(CR$_{15}$R$_{16}$)$_n$(OCH$_2$CH$_2$)$_y$SZ, —CO(CR$_{13}$R$_{14}$)$_m$(CR$_{15}$R$_{16}$)$_n$(OCH$_2$CH$_2$)$_y$SZ, —(CR$_{13}$R$_{14}$)$_m$(CR$_{17}$=CR$_{18}$)(CR$_{15}$R$_{16}$)$_m$(OCH$_2$CH$_2$)$_y$SZ, —CO(CR$_{13}$R$_{14}$)$_m$(CR$_{17}$=CR$_{18}$)(CR$_{15}$R$_{16}$)$_m$(OCH$_2$CH$_2$)$_y$SZ, —CONR$_{12}$(CR$_{13}$R$_{14}$)$_m$(CR$_{15}$R$_{16}$)$_n$(OCH$_2$CH$_2$)$_y$SZ, furyl-XSZ, oxazolyl-XSZ, thiazolyl-XSZ, thiopheneyl-XSZ, imidazolyl-XSZ, morpholino-XSZ, -piperazino-XSZ, piperidino-XSZ, —CO-furyl-XSZ, —CO-thiopheneyl-XSZ, —CO-thiazolyl-XSZ, —CO—N-methylpiperazino-XSZ, —CO-morpholino-XSZ, —CO-piperazino-XSZ, —CO-piperidino-XSZ, or —CO—N-methylpiperazino-XSZ, wherein Z is H or SR;

X is a linear or branched alkyl having from 1-10 carbon atoms, a linear or branched alkenyl having from 2-10 carbon atoms, or a polyethylene glycol spacer having from 2 to 20 repeating ethylene oxy units;

R and R$_{12}$ are the same or different and are linear alkyl, branched alkyl or cyclic alkyl having from 1 to 10 carbon atoms, or simple or substituted aryl or heterocyclic, and R$_{12}$ can in addition be H;

R$_{13}$, R$_{14}$, R$_{15}$ and R$_{16}$ are the same or different and are H or a linear or branched alkyl having from 1 to 4 carbon atoms;

R$_{17}$ and R$_{18}$ are H or methyl;

n is an integer from 1 to 10;

m is an integer from 1 to 10 and can also be 0; and y is an integer from 1 to 20 and can also be 0.

41. A pharmaceutical composition comprising a therapeutically effective amount of the cytotoxic agent of any one of claims 1 to 12 and a pharmaceutically acceptable carrier, diluent or excipient.

42. A method for inducing cell death in selected cell populations comprising contacting target cells or tissue containing the target cells with an effective amount of the cytotoxic agent of any one of claims 1 to 12.

43. A method of preparing the cytotoxic agent of claim 1 comprising reacting a compound of the following formula (I) with said cell-binding agent to thereby form a link from the C-7 position of the compound of formula (I) to the cell-binding agent:

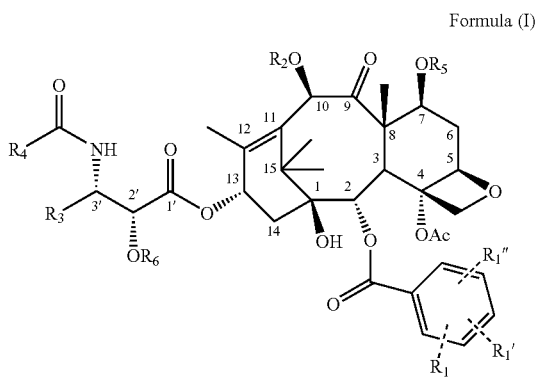

Formula (I)

wherein:
$R_1$ is H, an electron withdrawing group, or an electron donating group; $R_1'$ and $R_1''$ are the same or different, and are H, an electron withdrawing group, or an electron donating group;

$R_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms;

$R_3$ is alkenyl having from 2 to 10 carbon atoms, cycloalkenyl having from 3 to 10 carbon atoms or heterocyclic;

$R_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl, or heterocyclic and an oxygen atom;

$R_5$ is a linking group; and $R_6$ is H, or together with the oxygen atom at the C-2' position, a heterocyclic or aryl ether, a heterocyclic or aryl ester, a heterocyclic or aryl carbamate, a linear, branched or cyclic alkyl ester group having from 1 to 10 carbon atoms in the alkyl, a linear, branched or cyclic alkenyl ester group having from 2 to 10 carbon atoms in the alkenyl, a linear, branched, or cyclic alkyl ether group having from 1 to 10 carbon atoms, a linear, branched, or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms provided that when R$_3$ is —CH═C(CH$_3$)$_2$, R$_4$ is not an aryl or —OC(CH$_3$)$_3$.

44. The method of claim 43 wherein R$_2$ is H.

45. The method of claim 43 wherein R$_3$ is —CH═C(CH$_3$)$_2$.

46. A method of preparing the cytotoxic agent of claim 4 comprising reacting a compound of the following formula (I) with said cell-binding agent to thereby form a link from the oxygen atom at the C-10 position of the compound of formula (I) to the cell-binding agent:

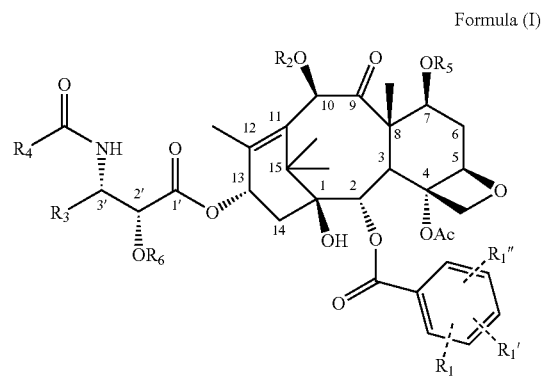

Formula (I)

wherein:
$R_1$ is H, an electron withdrawing group or an electron donating group;

$R_1'$ and $R_1''$ are the same or different and are H, an electron withdrawing group, or an electron donating group;

$R_2$ is a linking group;

$R_3$ is alkenyl having from 2 to 10 carbon atoms, cycloalkenyl having from 3 to 10 carbon atoms or heterocyclic;

$R_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl or heterocyclic and an oxygen atom;

$R_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms; and $R_6$ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, provided that when $R_3$ is —CH=C(CH$_3$)$_2$, $R_4$ is not an aryl or —OC(CH$_3$)$_3$.

47. A method of preparing the cytotoxic agent of claim 5 comprising reacting a compound of the following formula (I) with said cell-binding agent to thereby form a link from the oxygen atom at the C-2' position of the compound of formula (I) to the cell-binding agent:

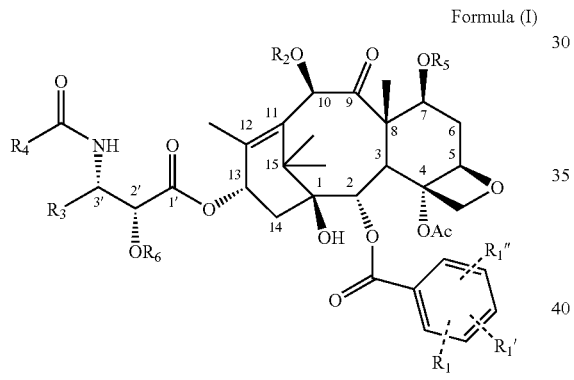

Formula (I)

wherein:

$R_1$ is H, an electron withdrawing group or an electron donating group;

$R_1'$ and $R_1''$ are the same or different and are H, an electron withdrawing group, or an electron donating group;

$R_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms;

$R_3$ is alkenyl having from 2 to 10 carbon atoms, cycloalkenyl having from 3 to 10 carbon atoms or heterocyclic;

$R_4$ is alkyl having from 1 to 10 carbon atoms, alkenyl having from 2 to 10 carbon atoms, cycloalkyl or cycloalkenyl having from 3 to 10 carbon atoms, aryl, heterocyclic, —OC(CH$_3$)$_3$, or together with the —CONH— group at the C-3' position, a carbamate formed from any of said alkyl, having from 1 to 10 carbon atoms, alkenyl having from 2 to 10 carbon atoms, cycloalkyl or cycloalkenyl having from 3 to 10 carbon atoms, aryl or heterocyclic and an oxygen atom;

$R_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms; and $R_6$ is a linking group provided that when $R_3$ is —CH=C(CH$_3$)$_2$, $R_4$ is not an aryl or —OC(CH$_3$)$_3$.

48. The method of claim 47 wherein $R_2$ is H.

49. A method of preparing the cytotoxic agent of claim 7 comprising reacting a compound of the following formula (I) with said cell-binding agent to thereby form a link from the C-3' carbon atom of the compound of formula (I) to the cell-binding agent:

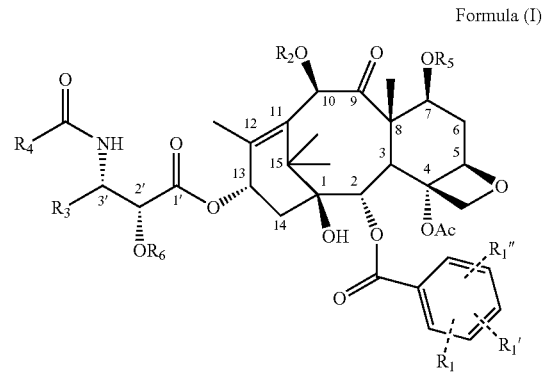

Formula (I)

wherein:

$R_1$ is H, an electron withdrawing group or an electron donating group;

$R_1'$ and $R_1''$ are the same or different and are H, an electron withdrawing group, or an electron donating group;

$R_3$ is a linking group;

$R_4$ is alkyl having from 1 to 10 carbon atoms, alkenyl having from 2 to 10 carbon atoms, cycloalkyl or cycloalkenyl having from 3 to 10 carbon atoms, aryl, or heterocyclic, —OC(CH$_3$)$_3$, or together with the —CONH— group at the C-3' position, a carbamate formed from any of said alkyl having from 1 to 10 carbon atoms, alkenyl having from 2 to 10 carbon atoms, cycloalkyl or cycloalkenyl having from 3 to 10 carbon atoms, aryl or heterocyclic and an oxygen atom; and R$_2$, R$_5$ and R$_6$ are the same or different and are H, or together with the oxygen atoms at the C-10, C-7 and C-2' positions, respectively, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms.

50. A method of preparing the cytotoxic agent of claim 8 comprising reacting a compound of the following formula (I) with said cell-binding agent to thereby form a link from the carbon atom at the C-3'N position of the compound of formula (I) to the cell-binding agent:

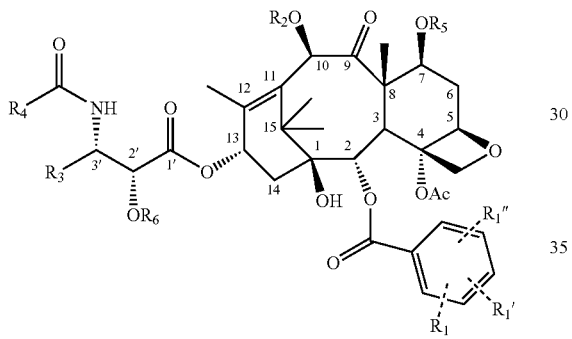

Formula (I)

wherein:
R$_1$ is H, an electron withdrawing group or an electron donating group;
R$_1$' and R$_1$" are the same or different and are H, an electron withdrawing group, or an electron donating group;
R$_3$ is alkyl having from 1 to 10 carbon atoms, alkenyl having from 2 to 10 carbon atoms, cycloalkyl or cycloalkenyl having from 3 to 10 carbon atoms, aryl or heterocyclic;
R$_4$ is a linking group; and
R$_2$, R$_5$ and R$_6$ are the same or different and are H, or together with the oxygen atoms at the C-10, C-7 and C-2' positions, respectively, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms.

51. A method of preparing the cytotoxic agent of claim 9 comprising reacting a compound of the following formula (I) with said cell-binding agent to thereby form a link from the oxygen atom at the C-2' position of the compound of formula (I) to the cell-binding agent:

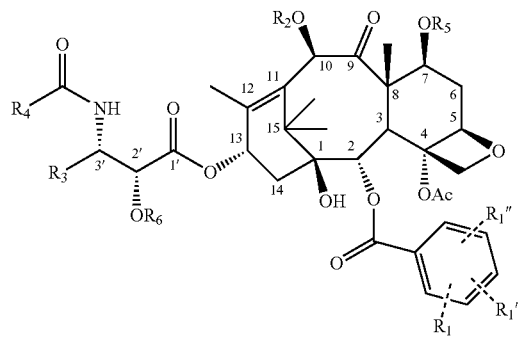

Formula (I)

wherein:
R$_1$ is H, an electron withdrawing group or an electron donating group;
R$_1$' and R$_1$" are the same or different and are H, an electron withdrawing group, or an electron donating group;
R$_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms;
R$_3$ is alkyl having from 1 to 10 carbon atoms, alkenyl having from 2 to 10 carbon atoms, cycloalkyl or cycloalkenyl having from 3 to 10 carbon atoms, aryl or heterocyclic;
R$_4$ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl, having from 1 to 10 carbon atoms, alkenyl having from 2 to 10 carbon atoms, cycloalkyl or cycloalkenyl having from 3 to 10 carbon atoms, aryl or heterocyclic and an oxygen atom; and
R$_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 1 to 10 carbon atoms, and R$_6$ is a linking group.

52. The method of claim 51, wherein R$_2$ is H.

53. A method of preparing the cytotoxic agent of claim 11 comprising reacting a compound of the following formula (I) with said cell-binding agent to thereby form a link from the oxygen atom at the C-10 position of the compound of formula (I) to the cell-binding agent:

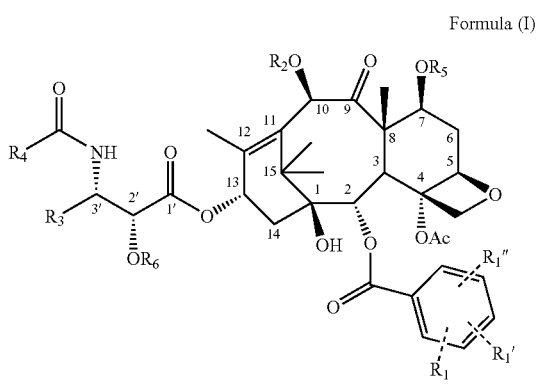

Formula (I)

wherein:
R$_1$ is H, an electron withdrawing group or an electron-donating group;
R$_1$' and R$_1$" are the same or different and are H, an electron withdrawing group, or an electron donating group;
R$_2$ is a linking group;
R$_3$ is alkyl or alkenyl having from 1 to 10 carbon atoms, cycloalkyl or cycloalkenyl having from 3 to 10 carbon atoms, aryl, or heterocyclic;
R$_4$ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl having from 1 to 10 carbon atoms, alkenyl having from 2 to 10 carbon atoms, cycloalkyl or cycloalkenyl having from 3 to 10 carbon atoms, aryl, or heterocyclic and an oxygen atom;
R$_5$ is H, or together with the oxygen atom at the C-7 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms; and
R$_6$ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbarnate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms.

54. A method of preparing the cytotoxic agent of claim 12 comprising reacting a compound of the following formula (I) with said cell-binding agent to thereby form a link from the C-7 position of the compound of formula (I) to the cell-binding agent:

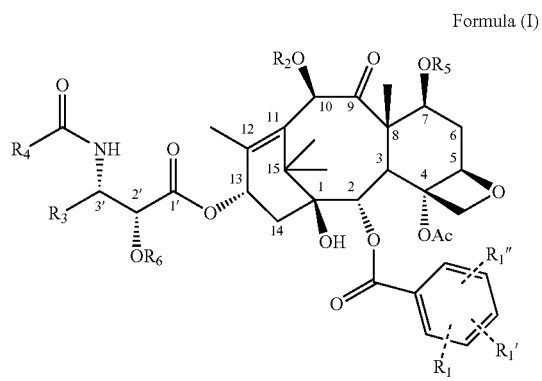

Formula (I)

wherein:
R$_1$ is H, an electron withdrawing group or an electron donating group;
R$_1$' and R$_1$" are the same or different and are H, an electron withdrawing group, or an electron donating group;
R$_2$ is H, or together with the oxygen atom at the C-10 position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate of the formula —OCONR$_{10}$R$_{11}$, wherein R$_{10}$ and R$_{11}$ are the same or different and are H, linear, branched or cyclic alkyl having from 1 to 10 carbon atoms, or simple or substituted aryl having from 6 to 10 carbon atoms;
R$_3$ is alkyl or alkenyl having from 1 to 10 carbon atoms, cycloalkyl or cycloalkenyl having from 3 to 10 carbon atoms, aryl, or heterocyclic;
R$_4$ is alkyl having from 1 to 10 carbon atoms, alkenyl having from 2 to 10 carbon atoms, cycloalkyl or cycloalkenyl having from 3 to 10 carbon atoms, heterocyclic, or together with the —CONH— group at the C-3' position, a carbamate formed from any of an alkyl having from 1 to 10 carbon atoms, alkenyl having from 2 to 10 carbon atoms, cycloalkyl or cycloalkenyl having from 3 to 10 carbon atoms, aryl, or heterocyclic and an oxygen atom;

$R_5$ is a linking group; and $R_6$ is H, or together with the oxygen atom at the C-2' position, a heterocyclic or aryl ether group, a heterocyclic or aryl ester group, a heterocyclic or aryl carbamate group, a linear, branched or cyclic alkyl ester group having from 1 to 10 carbon atoms in the alkyl, a linear, branched or cyclic alkenyl ester group having from 2 to 10 carbon atoms in the alkenyl, a linear, branched or cyclic alkyl ether group having from 1 to 10 carbon atoms, a linear, branched or cyclic alkenyl ether group having from 2 to 10 carbon atoms, a carbamate group of the formula —OCOX, wherein X is a nitrogen-containing heterocyclic group, or a carbamate group of the formula —OCONR$_{10}$R$_{11}$, wherein $R_{10}$ and $R_{11}$ are the same or different and are H, linear, branched or cyclic alkyl having from 1 to 10 carbon atoms, or simple or substituted aryl having from 6 to 10 carbon atoms.

55. A method of treating malignancy, comprising administering to a patient in need of treatment an effective amount of the cytotoxic agent of any one of claims 1-12.

56. The method of claim 55 wherein said malignancy is cancer of the lung, breast, colon, prostate, kidney, pancreas, ovary or lymphatic organs.

57. The method of claim 55 wherein the cytotoxic agent is in the form of a solution or a lyophilized powder and administered in normal saline.

* * * * *